US009228013B2

(12) United States Patent
Gurney et al.

(10) Patent No.: US 9,228,013 B2
(45) Date of Patent: *Jan. 5, 2016

(54) METHODS OF USING THE FRI DOMAIN OF HUMAN FRIZZLED RECEPTOR FOR INHIBITING WNT SIGNALING IN A TUMOR OR TUMOR CELL

(71) Applicant: OncoMed Pharmaceuticals, Inc., Redwood City, CA (US)

(72) Inventors: Austin Gurney, San Francisco, CA (US); John Lewicki, Los Gatos, CA (US); Sanjeev Satyal, San Carlos, CA (US); Timothy Hoey, Hillsborough, CA (US)

(73) Assignee: OncoMed Pharmaceuticals, Redwood City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/266,998

(22) Filed: May 1, 2014

(65) Prior Publication Data

US 2014/0349399 A1    Nov. 27, 2014

Related U.S. Application Data

(60) Continuation of application No. 13/667,191, filed on Nov. 2, 2012, now Pat. No. 8,765,913, which is a continuation of application No. 12/724,169, filed on Mar. 15, 2010, now Pat. No. 8,324,361, which is a division of application No. 11/589,931, filed on Oct. 31, 2006, now Pat. No. 7,723,477.

(60) Provisional application No. 60/731,468, filed on Oct. 31, 2005, provisional application No. 60/812,966, filed on Jun. 13, 2006.

(51) Int. Cl.
| | |
|---|---|
| *C07K 16/28* | (2006.01) |
| *C07K 14/705* | (2006.01) |
| *A61K 38/00* | (2006.01) |
| *A61K 45/06* | (2006.01) |
| *A61K 47/48* | (2006.01) |
| *C07K 14/72* | (2006.01) |
| *C07K 16/00* | (2006.01) |
| *G01N 33/574* | (2006.01) |
| *C07K 16/18* | (2006.01) |
| *A61K 39/00* | (2006.01) |

(52) U.S. Cl.
CPC ............... *C07K 16/28* (2013.01); *A61K 45/06* (2013.01); *A61K 47/48276* (2013.01); *A61K 47/48369* (2013.01); *C07K 14/705* (2013.01); *C07K 14/723* (2013.01); *C07K 16/00* (2013.01); *C07K 16/18* (2013.01); *G01N 33/57423* (2013.01); *G01N 33/57492* (2013.01); *A61K 38/00* (2013.01); *A61K 2039/505* (2013.01); *C07K 2319/30* (2013.01); *C07K 2319/33* (2013.01)

(58) Field of Classification Search
CPC ............... A61K 38/177; C07K 14/705; C07K 2319/30; C07K 2319/33
See application file for complete search history.

(56) References Cited

U.S. PATENT DOCUMENTS

| | | | |
|---|---|---|---|
| 3,687,808 | A | 8/1972 | Merigan et al. |
| 4,109,496 | A | 8/1978 | Allemann et al. |
| 4,323,546 | A | 4/1982 | Crockford et al. |
| 4,411,990 | A | 10/1983 | Salmon et al. |
| 4,612,282 | A | 9/1986 | Schlom et al. |
| 4,670,393 | A | 6/1987 | Seeburg |
| 4,873,191 | A | 10/1989 | Wagner et al. |
| 4,968,103 | A | 11/1990 | McNab et al. |
| 4,981,785 | A | 1/1991 | Nayak |
| 5,019,497 | A | 5/1991 | Olsson |
| 5,034,506 | A | 7/1991 | Summerton et al. |
| 5,061,620 | A | 10/1991 | Tsukamoto et al. |
| 5,087,570 | A | 2/1992 | Weissman et al. |

(Continued)

FOREIGN PATENT DOCUMENTS

| | | |
|---|---|---|
| EP | 0662827 A1 | 7/1995 |
| EP | 1 004 669 | 5/1998 |

(Continued)

OTHER PUBLICATIONS

Austin, T.W., et al.,"A role for the Wnt gene family in hematopoiesis: expansion of multilineage progenitor cells," *Blood* 89:3624-3635, the American Society of Hematology, Washington, DC, U.S.A. (1997).

(Continued)

*Primary Examiner* — Robert Landsman
(74) *Attorney, Agent, or Firm* — Sterne, Kessler, Goldstein & Fox PLLC

(57) ABSTRACT

The present invention relates to compositions and methods for characterizing, diagnosing, and treating cancer. In particular the invention provides the means and methods for the diagnosis, characterization, prognosis and treatment of cancer and specifically targeting cancer stem cells. The present invention provides a soluble FZD receptor comprising an extracellular domain of a human FZD receptor that inhibits growth of tumor cells. The present invention still further provides a soluble receptor comprising a Fri domain of a human FZD receptor that binds a ligand of a human FZD receptor and said soluble receptor is capable of inhibiting tumor growth. The present invention still further provides a method of treating cancer comprising administering a soluble FZD receptor comprising for example, either an extracellular domain of a human FZD receptor or a Fri domain of a human FZD receptor, in an amount effective to inhibit tumor growth.

12 Claims, 7 Drawing Sheets

(56) References Cited

U.S. PATENT DOCUMENTS

Figure 1:
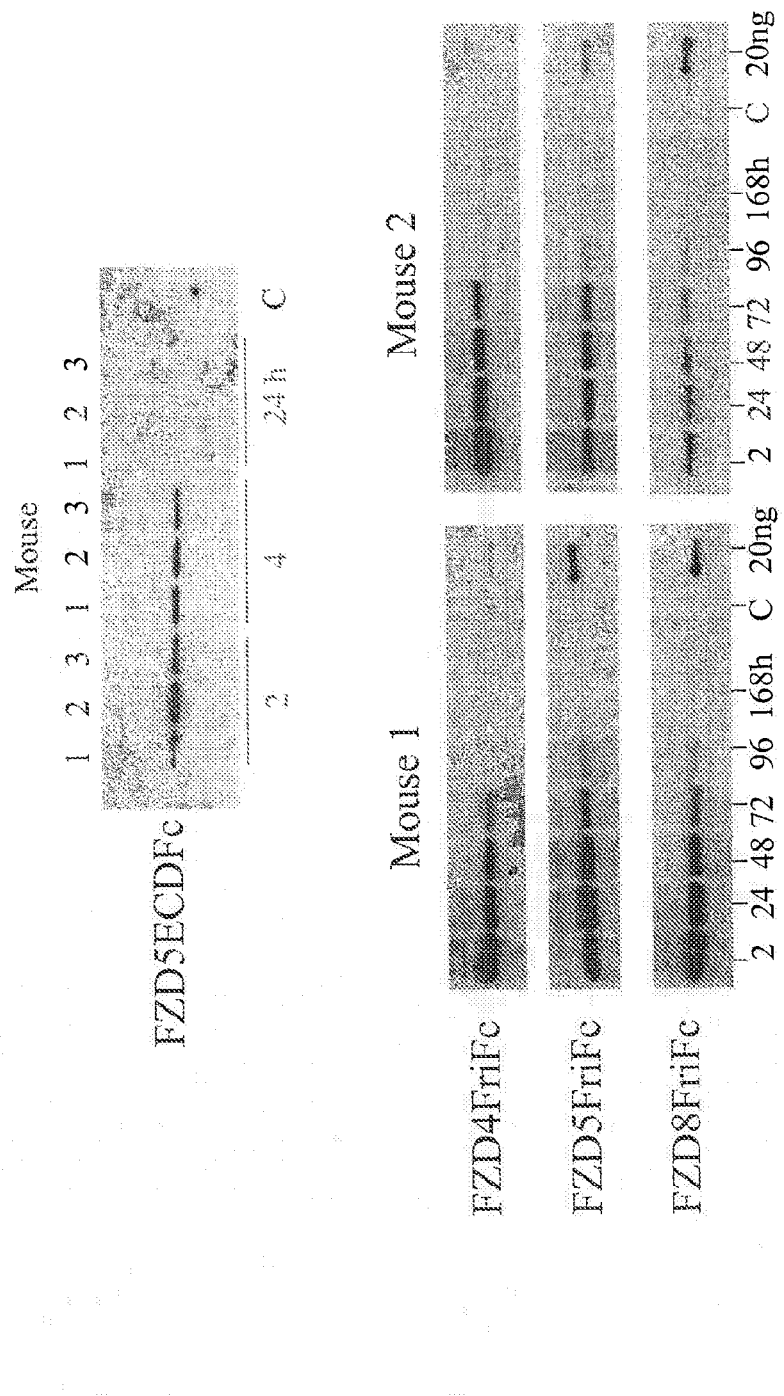

| | | |
|---|---|---|
| 5,223,409 A | 6/1993 | Ladner et al. |
| 5,225,539 A | 7/1993 | Winter |
| 5,283,317 A | 2/1994 | Saifer et al. |
| 5,358,691 A | 10/1994 | Clark et al. |
| 5,489,677 A | 2/1996 | Sanghvi et al. |
| 5,534,617 A | 7/1996 | Cunningham et al. |
| 5,538,848 A | 7/1996 | Livak et al. |
| 5,539,082 A | 7/1996 | Nielsen et al. |
| 5,565,332 A | 10/1996 | Hoogenboom et al. |
| 5,585,089 A | 12/1996 | Queen et al. |
| 5,589,376 A | 12/1996 | Anderson et al. |
| 5,599,677 A | 2/1997 | Dowell et al. |
| 5,602,240 A | 2/1997 | De Mesmaeker et al. |
| 5,614,396 A | 3/1997 | Bradley et al. |
| 5,631,169 A | 5/1997 | Lakowicz et al. |
| 5,639,606 A | 6/1997 | Willey |
| 5,643,741 A | 7/1997 | Tsukamoto et al. |
| 5,643,765 A | 7/1997 | Willey |
| 5,648,464 A | 7/1997 | Artavanis-Tsakonas et al. |
| 5,650,317 A | 7/1997 | Chang et al. |
| 5,654,183 A | 8/1997 | Anderson et al. |
| 5,672,499 A | 9/1997 | Anderson et al. |
| 5,674,739 A | 10/1997 | Shyjan |
| 5,688,666 A | 11/1997 | Bass et al. |
| 5,693,482 A | 12/1997 | Anderson et al. |
| 5,705,188 A | 1/1998 | Junichi et al. |
| 5,714,331 A | 2/1998 | Buchardt et al. |
| 5,719,262 A | 2/1998 | Buchardt et al. |
| 5,739,277 A | 4/1998 | Presta et al. |
| 5,750,373 A | 5/1998 | Garrard et al. |
| 5,750,376 A | 5/1998 | Weiss et al. |
| 5,753,229 A | 5/1998 | Mordoh et al. |
| 5,753,506 A | 5/1998 | Johe |
| 5,780,300 A | 7/1998 | Artavanis-Tsakonas et al. |
| 5,786,158 A | 7/1998 | Artavanis-Tsakonas et al. |
| 5,789,195 A | 8/1998 | Artavanis-Tsakonas et al. |
| 5,814,511 A | 9/1998 | Chang et al. |
| 5,821,108 A | 10/1998 | Akashi et al. |
| 5,824,489 A | 10/1998 | Anderson et al. |
| 5,824,544 A | 10/1998 | Armentano et al. |
| 5,830,730 A | 11/1998 | German et al. |
| 5,834,598 A | 11/1998 | Lowman et al. |
| 5,849,535 A | 12/1998 | Cunningham et al. |
| 5,849,553 A | 12/1998 | Anderson et al. |
| 5,849,869 A | 12/1998 | Artavanis-Tsakonas et al. |
| 5,854,026 A | 12/1998 | Cunningham et al. |
| 5,856,441 A | 1/1999 | Artavanis-Tsakonas et al. |
| 5,859,535 A | 1/1999 | Liu |
| 5,861,832 A | 1/1999 | Nagaraj |
| 5,869,282 A | 2/1999 | Ish-Horowicz et al. |
| 5,872,154 A | 2/1999 | Wilson et al. |
| 5,876,978 A | 3/1999 | Willey et al. |
| 5,885,530 A | 3/1999 | Babson et al. |
| 5,885,808 A | 3/1999 | Spooner et al. |
| 5,914,108 A | 6/1999 | Tsukamoto et al. |
| 5,935,792 A | 8/1999 | Rubin et al. |
| 5,942,225 A | 8/1999 | Bruder et al. |
| 5,981,225 A | 11/1999 | Kochanek et al. |
| 5,986,170 A | 11/1999 | Subjeck |
| 5,994,106 A | 11/1999 | Kovesdi et al. |
| 5,994,128 A | 11/1999 | Fallaux et al. |
| 5,994,132 A | 11/1999 | Chamberlain et al. |
| 5,994,617 A | 11/1999 | Dick et al. |
| 6,001,557 A | 12/1999 | Wilson et al. |
| 6,004,528 A | 12/1999 | Bergstein |
| 6,004,924 A | 12/1999 | Ish-Horowicz et al. |
| 6,019,978 A | 2/2000 | Ertl et al. |
| 6,022,711 A | 2/2000 | Cunningham et al. |
| 6,033,908 A | 3/2000 | Bout et al. |
| 6,054,297 A | 4/2000 | Carter et al. |
| 6,080,912 A | 6/2000 | Bremel et al. |
| 6,083,904 A | 7/2000 | Artavanis-Tsakonas |
| 6,090,922 A | 7/2000 | Artavanis-Tsakonas et al. |
| 6,117,985 A | 9/2000 | Thomas et al. |
| 6,121,045 A | 9/2000 | McCarthy et al. |
| 6,127,526 A | 10/2000 | Blank |
| 6,135,653 A | 10/2000 | Aichi |
| 6,136,952 A | 10/2000 | Li et al. |
| 6,143,523 A | 11/2000 | Cunningham et al. |
| 6,149,902 A | 11/2000 | Artavanis-Tsakonas et al. |
| 6,156,305 A | 12/2000 | Brauker et al. |
| 6,159,750 A | 12/2000 | Edmonds |
| 6,180,370 B1 | 1/2001 | Queen et al. |
| 6,190,876 B1 | 2/2001 | Rubin et al. |
| 6,197,523 B1 | 3/2001 | Rimm et al. |
| 6,198,107 B1 | 3/2001 | Seville |
| 6,207,147 B1 | 3/2001 | Hiserodt et al. |
| 6,218,166 B1 | 4/2001 | Ravindranath et al. |
| 6,252,050 B1 | 6/2001 | Ashkenazi et al. |
| 6,262,025 B1 | 7/2001 | Ish-Horowicz et al. |
| 6,353,150 B1 | 3/2002 | Dick et al. |
| 6,379,925 B1 | 4/2002 | Kitajewski et al. |
| 6,380,362 B1 | 4/2002 | Watson et al. |
| 6,429,186 B1 | 8/2002 | Fuh et al. |
| 6,433,138 B1 | 8/2002 | Zimrin et al. |
| 6,433,155 B1 | 8/2002 | Umansky et al. |
| 6,448,229 B2 | 9/2002 | Teall et al. |
| 6,506,559 B1 | 1/2003 | Driver et al. |
| 6,537,775 B1 | 3/2003 | Tournier-Lasserve et al. |
| 6,583,115 B1 | 6/2003 | Kopchick et al. |
| 6,632,620 B1 | 10/2003 | Makarovskiy |
| 6,660,843 B1 | 12/2003 | Feige et al. |
| 6,664,098 B1 | 12/2003 | Sakano |
| 6,683,091 B2 | 1/2004 | Asberom et al. |
| 6,689,744 B2 | 2/2004 | Gao et al. |
| 6,703,221 B1 | 3/2004 | Chan et al. |
| 6,703,489 B1 | 3/2004 | Lewis et al. |
| 6,713,206 B2 | 3/2004 | Markoski et al. |
| 6,716,974 B1 | 4/2004 | Maciag et al. |
| 6,756,511 B2 | 6/2004 | Castro Pineiro et al. |
| 6,894,522 B2 | 5/2005 | Averill et al. |
| 6,984,522 B2 | 1/2006 | Clarke et al. |
| 7,091,321 B2 | 8/2006 | Gillies et al. |
| 7,091,323 B2 | 8/2006 | Pan et al. |
| 7,115,360 B2 | 10/2006 | Clarke et al. |
| 7,115,653 B2 | 10/2006 | Baxter et al. |
| 7,118,853 B2 | 10/2006 | Botstein et al. |
| 7,138,370 B2 | 11/2006 | Oliner et al. |
| 7,211,404 B2 | 5/2007 | Lagasse et |
| 7,361,336 B1 | 4/2008 | Bergstein |
| 7,381,408 B2 | 6/2008 | Mezo et al. |
| 7,404,956 B2 | 7/2008 | Peters et al. |
| 7,413,873 B2 | 8/2008 | Waterman et al. |
| 7,442,778 B2 | 10/2008 | Gegg et al. |
| 7,507,406 B2 | 3/2009 | Gillies et al. |
| 7,608,453 B2 | 10/2009 | Cattaneo et al. |
| 7,635,530 B2 | 12/2009 | Kenis et al. |
| 7,659,116 B2 | 2/2010 | Buehring et al. |
| 7,662,931 B2 | 2/2010 | Gegg et al. |
| 7,682,607 B2 | 3/2010 | Rhee et al. |
| 7,713,526 B2 | 5/2010 | Rhee et al. |
| 7,723,477 B2 | 5/2010 | Gurney et al. |
| 7,803,370 B2 | 9/2010 | Nakamura et al. |
| 7,803,783 B2 | 9/2010 | Lee et al. |
| 7,803,913 B2 | 9/2010 | Dimitrov et al. |
| 7,867,705 B2 | 1/2011 | Wands et al. |
| 7,879,322 B2 | 2/2011 | Kneissel et al. |
| 7,947,277 B2 | 5/2011 | Ernst et al. |
| 7,982,013 B2 | 7/2011 | Gurney et al. |
| 8,017,559 B2 | 9/2011 | Etzerodt et al. |
| 8,158,761 B2 | 4/2012 | Wands et al. |
| 8,410,061 B2 | 4/2013 | Williams et al. |
| 8,431,532 B2 | 4/2013 | Brennan et al. |
| 8,507,442 B2 | 8/2013 | Gurney et al. |
| 8,551,789 B2 | 10/2013 | Gurney |
| 8,809,287 B2 | 8/2014 | Bafico et al. |
| 2002/0119565 A1 | 8/2002 | Clarke et al. |
| 2002/0137129 A1 | 9/2002 | Barnes et al. |
| 2002/0151487 A1 | 10/2002 | Nickoloff et al. |
| 2002/0169300 A1 | 11/2002 | Waterman et al. |
| 2002/0187502 A1 | 12/2002 | Waterman et al. |
| 2003/0032184 A1 | 2/2003 | Lagasse et al. |
| 2003/0044409 A1 | 3/2003 | Carson et al. |
| 2003/0064384 A1 | 4/2003 | Hung et al. |

(56) References Cited

U.S. PATENT DOCUMENTS

| | | | |
|---|---|---|---|
| 2003/0086934 A1 | 5/2003 | Botstein et al. |
| 2003/0114387 A1 | 6/2003 | Castro et al. |
| 2003/0119029 A1 | 6/2003 | Glick et al. |
| 2003/0135044 A1 | 7/2003 | Asberom et al. |
| 2003/0139457 A1 | 7/2003 | Baxter et al. |
| 2003/0162709 A1 | 8/2003 | Rossi et al. |
| 2003/0165500 A1 | 9/2003 | Rhee et al. |
| 2003/0166543 A1 | 9/2003 | Williams et al. |
| 2003/0175877 A1 | 9/2003 | Baker et al. |
| 2003/0180784 A1 | 9/2003 | McCarthy et al. |
| 2003/0185829 A1 | 10/2003 | Koller et al. |
| 2003/0229023 A1 | 12/2003 | Oliner et al. |
| 2004/0023244 A1 | 2/2004 | Griffin et al. |
| 2004/0037815 A1 | 2/2004 | Clarke et al. |
| 2004/0038876 A1 | 2/2004 | Pepinsky et al. |
| 2004/0048249 A1 | 3/2004 | Tang et al. |
| 2004/0058217 A1 | 3/2004 | Ohlsen et al. |
| 2004/0058443 A1 | 3/2004 | Artavanis-Tsakonas et al. |
| 2004/0105862 A1 | 6/2004 | Pan et al. |
| 2004/0127474 A1 | 7/2004 | Dudek et al. |
| 2004/0171559 A1 | 9/2004 | Weissman et al. |
| 2004/0203003 A1 | 10/2004 | Rhee et al. |
| 2004/0214186 A1 | 10/2004 | Engelberg et al. |
| 2004/0219579 A1 | 11/2004 | Aziz et al. |
| 2004/0247593 A1 | 12/2004 | He et al. |
| 2005/0123900 A1 | 6/2005 | Dimitrov et al. |
| 2005/0130199 A1 | 6/2005 | Carson et al. |
| 2005/0272063 A1 | 12/2005 | Nakamura et al. |
| 2005/0288864 A1 | 12/2005 | Cattaneo et al. |
| 2006/0019256 A1 | 1/2006 | Clarke et al. |
| 2006/0019320 A1 | 1/2006 | Civenni et al. |
| 2006/0040883 A1 | 2/2006 | You et al. |
| 2006/0210867 A1 | 9/2006 | Kenis et al. |
| 2007/0072238 A1 | 3/2007 | Bhat |
| 2007/0116701 A1 | 5/2007 | Gurney et al. |
| 2007/0117751 A1 | 5/2007 | Gurney et al. |
| 2007/0237770 A1 | 10/2007 | Lai et al. |
| 2007/0238658 A1 | 10/2007 | Levin et al. |
| 2008/0038272 A1 | 2/2008 | Buehring et al. |
| 2008/0044423 A1 | 2/2008 | Cochrane et al. |
| 2008/0075714 A1 | 3/2008 | Lee et al. |
| 2008/0118432 A1 | 5/2008 | Bergstein et al. |
| 2008/0194457 A1 | 8/2008 | Wands et al. |
| 2008/0299136 A1 | 12/2008 | Ernst et al. |
| 2009/0023905 A1 | 1/2009 | Askew et al. |
| 2009/0074777 A1 | 3/2009 | Wands et al. |
| 2009/0130113 A1 | 5/2009 | Kneissel et al. |
| 2009/0163407 A1 | 6/2009 | Bafico et al. |
| 2009/0186010 A1 | 7/2009 | Li et al. |
| 2009/0234104 A1 | 9/2009 | Gegg et al. |
| 2009/0263400 A1 | 10/2009 | Urdea et al. |
| 2009/0304695 A1 | 12/2009 | He et al. |
| 2010/0104574 A1 | 4/2010 | Gurney et al. |
| 2010/0169025 A1 | 7/2010 | Arthur et al. |
| 2011/0020368 A1 | 1/2011 | Hynes |
| 2011/0224243 A1 | 9/2011 | Rethore |
| 2011/0237514 A1 | 9/2011 | Kakitani et al. |
| 2011/0318341 A1 | 12/2011 | Gurney et al. |
| 2012/0003222 A1 | 1/2012 | Brennan et al. |
| 2012/0027778 A1 | 2/2012 | Gurney |
| 2013/0252326 A1 | 9/2013 | Gurney et al. |
| 2013/0295105 A1 | 11/2013 | Gurney et al. |
| 2013/0295106 A1 | 11/2013 | Gurney et al. |
| 2014/0105917 A1 | 4/2014 | Gurney |
| 2014/0134159 A1 | 5/2014 | Stagg et al. |

FOREIGN PATENT DOCUMENTS

| | | |
|---|---|---|
| EP | 0 861 894 | 9/1998 |
| EP | 0 662 827 | 4/2002 |
| EP | 1 576 119 A | 9/2005 |
| EP | 1 805 221 A | 4/2006 |
| EP | 1 805 519 | 7/2007 |
| WO | WO 90/08832 | 8/1990 |
| WO | WO 92/19734 | 11/1992 |
| WO | WO 94/07474 | 4/1994 |
| WO | WO 94/10300 | 5/1994 |
| WO | WO 97/01571 | 1/1997 |
| WO | WO 97/30731 | 8/1997 |
| WO | WO 97/37004 | 10/1997 |
| WO | WO 98/05775 | 2/1998 |
| WO | WO 98/45434 | 10/1998 |
| WO | WO 98/51799 | 11/1998 |
| WO | WO 98/57621 | 12/1998 |
| WO | WO 99/02685 | 1/1999 |
| WO | WO 00/06726 | 2/2000 |
| WO | WO 00/09675 | 2/2000 |
| WO | WO 00/12738 | 3/2000 |
| WO | WO 00/52143 | 9/2000 |
| WO | WO-0102568 A2 | 1/2001 |
| WO | WO 01/26643 A1 | 4/2001 |
| WO | WO 01/98354 | 12/2001 |
| WO | WO 01/98537 | 12/2001 |
| WO | WO 02/00576 A1 | 1/2002 |
| WO | WO 02/12447 A2 | 2/2002 |
| WO | WO 02/18544 | 3/2002 |
| WO | WO 02/078703 A1 | 10/2002 |
| WO | WO 02/088081 A | 11/2002 |
| WO | WO 02/092635 A2 | 11/2002 |
| WO | WO 02/102978 A2 | 12/2002 |
| WO | WO 03/000893 A2 | 1/2003 |
| WO | WO 03/004045 A2 | 1/2003 |
| WO | WO 03/042246 A2 | 5/2003 |
| WO | WO 03/047316 | 6/2003 |
| WO | WO 03/050502 A2 | 6/2003 |
| WO | WO 03/062273 | 7/2003 |
| WO | WO 03/088964 A1 | 10/2003 |
| WO | WO 04/001004 | 12/2003 |
| WO | WO 2004/020668 A2 | 3/2004 |
| WO | WO 2004/032838 A2 | 4/2004 |
| WO | WO 2004/042028 A2 | 5/2004 |
| WO | WO 2004/053069 A2 | 6/2004 |
| WO | WO 2004/065545 A2 | 8/2004 |
| WO | WO 2004/073657 A2 | 9/2004 |
| WO | WO 2004/101739 A2 | 11/2004 |
| WO | WO 2005/001025 A2 | 1/2005 |
| WO | WO 2005/004912 A1 | 1/2005 |
| WO | WO 2005/005601 A2 | 1/2005 |
| WO | WO 2006/034328 A2 | 3/2006 |
| WO | WO 2006/036173 A2 | 4/2006 |
| WO | WO 2006/036175 A2 | 4/2006 |
| WO | WO 2006/040163 A1 | 4/2006 |
| WO | WO 2006/055635 A2 | 5/2006 |
| WO | WO 2006/056340 A2 | 6/2006 |
| WO | WO 2006/130076 A1 | 12/2006 |
| WO | WO 2007/053577 A2 | 5/2007 |
| WO | WO 2007/096149 A1 | 8/2007 |
| WO | WO 2007/133250 A2 | 11/2007 |
| WO | WO 2007/134876 A2 | 11/2007 |
| WO | WO 2007/142711 A2 | 12/2007 |
| WO | WO 2007/148417 A1 | 12/2007 |
| WO | WO 2008/031009 A2 | 3/2008 |
| WO | WO-2008039071 A2 | 4/2008 |
| WO | WO 2008/057459 A2 | 5/2008 |
| WO | WO 2008/061020 A2 | 5/2008 |
| WO | WO 2009/042971 A2 | 4/2009 |
| WO | WO 2009/118300 A1 | 10/2009 |
| WO | WO 2010/031979 A1 | 3/2010 |
| WO | WO 2010/037041 A2 | 4/2010 |
| WO | WO 2010/038756 A1 | 8/2010 |
| WO | WO-2011088123 A2 | 7/2011 |
| WO | WO-2011101409 A1 | 8/2011 |
| WO | WO-2011112678 A1 | 9/2011 |
| WO | WO 2011/123785 A3 | 10/2011 |
| WO | WO-2011123785 A3 | 12/2011 |
| WO | WO 2012/003189 A1 | 1/2012 |
| WO | WO 2012/006027 A1 | 1/2012 |
| WO | WO-2012058393 A2 | 5/2012 |
| WO | WO-2014121196 A1 | 8/2014 |

(56) References Cited

OTHER PUBLICATIONS

Ayyanan, A., et al., "Increased Wnt signaling triggers oncogenic conversion of human breast epithelial cells by a Notch-dependent mechanism," *PNAS* 103:3799-3804, the National Academy of Sciences, Washington, DC, U.S.A. (2006).

Bafico, A., et al., "An autocrine mechanism for constitutive Wnt pathway activation in human cancer cells," *Cancer Cell* 6:497-506, Cambridge, Mass. : Cell Press, U.S.A. Nov. (2004).

Bafico, A., et al., "Interaction of Frizzled Related Protein (FRP) with Wnt Ligands and the Frizzled Receptor Suggests Alternative Mechanisms for FRP Inhibition of Wnt Signalling," *J Biol. Chem.* 274:16180-16187, The American Society for Biochemistry and Molecular Biology, Inc., Bethesda, MD, U.S.A. (1999).

Barker, N. and Clevers, H., "Mining the Wnt pathway for cancer therapeutics," *Nature Reviews/Drug Discovery* 5:997-1014, Nature Publishing Group, New York, NY, U.S.A. (2006).

Battula, V.L., et al., "Prospective isolation and characterization of mesenchymal stem cells from human placenta using a frizzled-9-specific monoclonal antibody," *Differentiation* 76:326-336, International Society of Differentiation, Higgannum, CT, U.S.A. (2008).

Benhamouche, S., et al.,"*Apc* Tumor Suppressor Gene Is the "Zonation-Keeper" of Mouse Liver," *Developmental Cell* 10:759-770, Elsevier Inc., Amsterdam, The Netherlands (2006).

Bhanot, P., et al.,"A new member of the *frizzled* family from *Drosophila* functions as a Wingless receptor," *Nature* 382:225-230, Nature Publishing Group, New York, NY, U.S.A. (1996).

Bienz, M., "β-Catenin: A Pivot between Cell Adhesion and Wnt Signalling," *Current Biology* 15:R64-R67, Cell Press, St. Louis, MO, U.S.A. Jan. (2005).

Booy, E.P., et al., "Monoclonal and bispecific antibodies as novel therapeutics," *Arch. Immunol. Ther. Exp.* 54:85-101, Birkhäuser publications, Basel, Switzerland (2006).

Brabletz, T., et al., "Variable β-catenin expression in colorectal cancers indicates tumor progression driven by the tumor environment," *PNAS* 98(18):10356-10361, National Academy of Sciences, Washington, DC, U.S.A. (2001).

Brennan, K.R. and Brown, A.M.C., "Wnt Proteins in Mammary Development and Cancer," *J. Mammary Gland Biol. Neoplasia* 9(2):119-131, Kluwer Academic/Plenum Publishers Apr. (2004).

Burgess, W.H., et al., "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue," *J. Cell Bio.* 111:2129-2138, The Rockefeller University Press, New York, NY, U.S.A. (1990).

Cadigan, K.M. and Nusse, R., "Wnt signaling: a common theme in animal development," *Genes & Development* 11:3286-3305, Cold Spring Harbor Laboratory Press (1997).

Caldwell, G.M., et al., "The Wnt Antagonist *sFRP1* in Colorectal Tumorigenesis," *Cancer Res* 64:883-888, American Association for Cancer Research, Philadelphia, PA, U.S.A. Feb. (2004).

Chan, E. F., et al., "A common human skin tumour is caused by activating mutations in β-catenin, " *Nature Genetics* 27(4): 410-413 (1999).

Chen, Y., et al., "Selection and Analysis of an Optimized Anti-VEGF Antibody: Crystal Structure of an Affinity-matured Fab in Complex with Antigen," *Journal of Molecular Biology* 293(4): 865-881, Academic Press, England (1999).

Clevers, H., "Axin and hepatocellular carcinomas," *Nature Genetics* 24:206-208, Nature Publishing Group, New York, NY, U.S.A. (2000).

Daniel, C., et al., "Mapping of Linear Antigenic Sites on the S Glycoprotein of a Neurotropic Murine Coronavirus with Synthetic Peptides: A Combination of Nine Prediction Algorithms Fails to Identify Relevant Episodes and Peptide Immunogenicity Is Drastically Influenced by the Nature of the Protein Carrier," *Virology* 202(2):540-549, Elsevier Inc., The Netherlands (1994).

Dann, C.E., et al., "Insights into Wnt binding and signalling from the structures of two Frizzled cysteine-rich domains," *Nature* 412:86-90, Nature Publishing Group, New York, NY, U.S.A. (2001).

Datta, D.V., "Viral Hepatitis," *Jr. Asso. Phys. Ind.* 25(5):325-330, Association of Physicians of India, Mumbai, India (1977).

Davidson, G., et al., "Casein kinase Iγ couples Wnt receptor activation to cytoplasmic signal transduction," *Nature* 438:867-872, Nature Publishing Group, U.S.A. Dec. (2005).

De Lau, W. and Clevers, H., "LEF1 turns over a new leaf," *Nature Genetics* 28:3-4, Nature Publishing Group, NY, U.S.A. (2001).

De Pascalis, R., et al., "Grafting of Abbreviated Complementarity-Determining Regions Containing Specificity-Determining Residues Essential for Ligand Contact to Engineer a Less Immunogenic Humanized Monoclonal Antibody," *Journal of Immunology* 169:3076-3084, Williams & Wilkins, Baltimore, MD U.S.A. (2002).

Dealmeida, V.I., et al., "The Soluble Wnt Receptor Frizzled8CRD-hFc Inhibits the Growth of Teratocarcinomas In vivo," *Cancer Res* 67(01):5371-5379, American Association for Cancer Research (Jun. 1, 2007).

Dorvillius, Mylene et al., "Targeting of Human Brest Cancer by a Bispecific Antibody Directed against Two Tumour-Associated Antigens: ErbB-2 and Carcinoembryonic Antigen," *Tumor Biology*, S. Karger Medical and Scientific Publishers, Basel. 23(6): 337-347 (2002).

Fillmore et al., "Human breast cancer cell lines contain stem-like cells that self-renew, give rise to phenotypically diverse progeny and survive chemotherapy" *Breast Cancer Res*, voi10R25: 1-13, Current Science, London, UK (2008).

Finch, P.W., et al., "Purification and molecular cloning of a secreted, Frizzled-related antagonist of Wnt action," *PNAS* 94:6770-6775, the National Academy of Sciences, Washington, DC, U.S.A. (1997).

Fogel, M. at al., "L1 expression as a predictor of progression and survival in patients with uterine and ovarian carcinomas," *The Lancet* 362:869-875, Elsevier Inc., Amsterdam, The Netherlands (2003).

Fukukawa, C., et al., "Radioimmunotherapy of human synovial sarcoma using a monoclonal antibody against FZD10," *Cancer Sci.* 99:432-440, Wiley-Blackwell, Hoboken, NJ, U.S.A. (2008).

Gavert, N. et al., "L1, a novel target of β-catenin signaling, transforms cells and is expressed at the invasive front of colon cancers," *Journal of Cell Biology* 168(4):633-642, The Rockefeller University Press (Feb. 14, 2005).

Gazit A. et al., "Human frizzles 1 interacts with transforming Wnts to transducer a TCF dependent transcriptional response," *Oncogene* 18:5959-5966, Stockton Press, Scientific & Medical Division, MacMillan Press, Basingstoke, Hampshire, UK (1999).

Golan, T., et al., "The Human Frizzled 6 (IIFz6) Acts as a Negative Regulator of the Canonical Wnt. β-Catenin Signaling Cascade," *J. Biol. Chem.* 279:14879-14888, American Society for Biochemistry and Molecular Biology (Apr. 2004).

Greenspan, N. S. and Di Cera, E., "Defining epitopes: It's not as easy as it seems," *Nature Biotechnology* 17:936-937, Nature Publishing Group, United States (1999).

Gregorieff, A., et al ., "Expression Pattern of Wnt Signaling Components in the Adult Intestine," *Gastroenterology* 129:626-638, American Gastroenterological Association (Aug. 2005).

Greiner, D.L., et al., "SCID Mouse Models of Human Stem Cell Engraftment," *Stem Cells* 16:166-177, AlphaMed Press (1998).

Guo, H.H., et al., "Protein tolerance to random amino acid change," *PNAS*, 101:9205-9210, the National Academy of Sciences, Washington, DC, U.S.A. Jun. (2004).

Harada, N., et al., "Intestinal polyposis in mice with a dominant stable mutation of the β-catenin gene," *EMBO J.* 18:5931-5942, Oxford University Press, New York, NY U.S.A. (1999).

He, X. and Axelrod, J.D., "A WNTer wonderland in Snowbird," *Development* 133:2597-2603, The Company of Biologists, Cambridge, UK, U.S.A. (2006).

Hering H et al., "Direct interaction of Frizzled-1, -2, -4 and -7 with PDZ domains of PSD-95" *FEBS Letters* 521:185-189, Elsevier, Netherlands (2002).

Hicks, et al., "Fringe differentially modulates Jagged 1 and Delta 1 signalling through Notch1 and Notch2" *Nat Cell Bioi.* (8):515-520, Macmillan Magazines Ltd., London, UK (2000).

Hill, R. P., "Identifying cancer stern cells in solid tumors: case not proven" *Cancer Research* 66:1891-1896, American Association for Cancer Research (2006).

(56) References Cited

OTHER PUBLICATIONS

Holcombe, R.F., et al., "Expression of Wnt ligands and Frizzled receptors in colonic mucosa and in colon carcinoma," J. Clin. Pathol: Mol. Pathol. 55:220-226, BMJ Publishing Group (2002).

Holmes, E.H., "PSMA specific antibodies and their diagnostic and therapeutic use," *Exp. Opin. Invest. Drugs* 70:511-519, Informa Pharmaceutical Science, London, UK (2001).

Hsieh, A.C. and Moasser, M.M., "Targeting HER proteins in cancer therapy and the role of the non-target HER3," *British J. Cancer* 97:453-457, Cancer Research UK, England (2007).

Hsieh, J-C., et al, "Biochemical characterization of Wnt-Frizzled interactions using a soluble, biologically active vertebrate Wnt protein," *Proc. Natl. Acad. Sci. U.S.A.* 96(7):3546-3551, National Academy of Sciences, United States (Mar. 1999).

Huang, H-C. and Kletn, P.S., "The Frizzled family: receptors for multiple signal transduction pathways," *Genome Biol.* 5:234.1-234.7, BioMed Central Ltd. (Jun. 2004).

Ilyas, M., Wnt signalling and the mechanistic basis of tumour development, *J Pathology* 205:130-144, Oliver & Boyd., London, UK (2005).

International Search Report for International Patent Application No. PCT/US11/30950, ISA/US, Alexandria, Virginia 22313-1450, mailed on Oct. 18, 2011.

Ishikawa, T., et al., "Mouse Wnt receptor gene *Fzd 5* is essential for yolk sac and placental angiogenesis," *Development* 128:25-33, Company of Biologists Limited (2001).

Ishitani, T., et al., "The TAK1-NLK Mitogen-Activated Protein Kinase Cascade Functions in the Wnt-5a/Ca$^{2+}$ Pathway to Antagonize Wnt/β-Catenin Signaling," *Mol. Cell. Biol.* 23:131-139, American Society for Microbiology (2003).

Jamieson, C.H.M., et al., "Granulocyte-Macrophage Progenitors as Candidate Leukemic Stem Cells in Blast-Crisis CML" *N. Engl. J. Med.* 351:657-667, Massachusetts Medical Society, Waltham, MA, U.S.A. Aug. (2004).

Janssens, N., et al., "Alteration of Frizzled Expression in Renal Cell Carcinoma," *Tumor Biol.* 25:161-171, Karger (Jul. 2004).

Jiang, B., et al., "A Novel Peptide Isolated from a Phage Display Peptide Library with Trastuzumab Can Mimic Antigen Epitope of HER-2," *J. Biol. Chem.* 280:4656-4662, The American Society for Biochemistry and Molecular Biology, Inc., Bethesda, MD, U.S.A. Feb. (2005).

Joesting, M.S., et al., "Identification of SFRP1 as a Candidate Mediator of Stromal-to-Epithelial Signaling in Prostate Cancer," *Cancer Res.* 65:10423-10430, the American Association for Cancer Research, Philadelphia, PA, U.S.A. Nov. (2005).

Johnson, M.L., et al., "LRP5 and Wnt Signaling: A Union Made for Bone," *J. Bone Mineral Res.* 19:1749-1757, American Society for Bone and Mineral Research, Washington DC, U.S.A. Aug. (2004).

Jones, D.T., "Critically assessing the state-of-the-art in protein structure prediction," *Pharmacogenomics Journal* 1:126-134, Nature Publishing Group, New York, NY, U.S.A. (2001).

Jonsson, M., et al., "Involvement of adenomatous polyposis coli (APC)/β-catenin signalling in human breast cancer," *Eur. J. Cancer* 36: 242-248, : Pergamon Press, Oxford, England (2000).

Katoh, M. and Katoh, M., "WNT Signaling Pathway and Stem Cell Signaling Network," *Clin. Cancer Res.* 73:4042-4045, the American Association for Cancer Research, Philadelphia, PA, U.S.A. (2007).

Katoh, M. and Katoh, M., "STAT3-induced WNT5A signaling loop in embryonic stem cells, adult normal tissues, chronic persistent inflammation, rheumatoid arthritis and cancer (Review)," *Int. J. Mol. Med.* 19:273-278, D.A. Spandidos (Feb. 2007).

Katoh, M., "Molecular Cloning and Characterization of *MFRP*, a Novel Gene Encoding a Membrane-Type Frizzled-Related Protein," *Biochemical and Biophysical Research Communications* 282:116-123, Academic Press, United States (2001).

Kawakami, Y., et al., "Involvement of Frizzled-10 in Wnt-7a signaling during chick limb development," *Dev. Growth Differ.* 42:561-569, Blackwell Publishing (2000).

Kawano, Y. and Kypta, R., "Secreted antagonists of the Wnt signaling pathway," *Journal of Cell Science* 116:2627-2634, The Company of Biologists Ltd, London, UK (2003).

Kirikoshi et al., "Expression of *WNT10A* in human cancer," *Int J Oncology* 19:997-1001 (2001).

Kirikoshi, H., et al., "Expression profiles of 10 members of *Frizzled* gene family in human gastric cancer," *Int. J. Oncol.* 19:767-771, D.A. Spandidos (2001).

Kirikoshi, H., et al., "Molecular Cloning and Characterization of Human *Frizzled-4* on Chromosome 11q14-q21," *Biochem. Biophys. Res. Commun.* 264:955-961, Acadetnie Press (1999).

Kirikoshi, H., at al., "Up-regulation of *Frizzled-7 (FZD7)* in human gastric cancer," *Int. J. Oncol.* 19:111-115, D.A. Spandidos (2001).

Kirikoshi, H., et al., "Molecular Cloning and Genomic Structure of Human *Frizzled-3* at Chromosome 8p21," *Biochemical and Biophysical Research Communications* 271:8-14, Academic Press, United States (2000).

Kirkin, A.F., et al., "Melanoma-associated antigens recognized by cytotoxic T lymphocytes," *APMIS* 106:665-679, AMPIS, Denmark (1998).

Klaus, A. and Birchmeier, W., "Wnt signaling and its impact on development and cancer," *Nature Reviews/Cancer* 8:387-398, Nature Publishing Group, New York, NY, U.S.A. (May 2008).

Kobielak, A. and Fuchs, E., "α-Catenin: at the junction of intercelullar adhesion and actin dynamics," Nat Rev Mol Cell Bioi. 5:614-25, Nature Pub. Group, London, UK Aug. (2004).

Koike, J., et al., "Molecular Cloning of *Frizzled-10*, a Novel Member of the *Frizzled* Gene Family," *Biochem. Biophys. Res. Commun.* 262:39-43, Academic Press (1999).

Korinek, V., et al., "Two Members of the Tcf Family Implicated in Wnt/β-catenin Signaling during Embryogenesis in the Mouse," *Mol Cell Bioi* 18: 1248-1256, American Society for Microbiology, United States (1998).

Kuhnert, F., et al., "Essential requirement for Wnt signaling in proliferation of adult small intestine and colon revealed by adenoviral expression of Dickkopf-1," *PNAS* 101:266-271, the National Academy of Sciences, Washington, DC, U.S.A. Jan. (2004).

Lazer, E., et al., "Transforming Growth Factor α: Mutation of Aspartic Acid 47 and Leucine 48 Results in Different Biological Activities," *Mol. Cell. Bio.* 8:1247-1252, American Society for Microbiology, Washington, DC, U.S.A. (1988).

Lee, H.X., et al., "Embryonic Dorsal-Ventral Signaling: Secreted Frizzled-related Proteins as Inhibitors of Tolloid Proteinases," *Cell* 124:147-159, Elsevier Inc., Amsterdam, The Netherlands (Jan. 13, 2006).

Li, Y., et al., "LRP6 expression promotes cancer cell proliferation and tumorigenesis by altering β-catenin subcellular distribution," *Oncogene* 23:9129-9135, Nature Publishing Group, New York, NY, U.S.A. Oct. (2004).

Li, Y., et al., "The Gene for Autosomal Dominant Familial Exudative Vitreoretinopathy (Criswick-Schepens) on the Long Arm of Chromosome 1 1," *Am. J. Opthcanol.* 113:712-713, Elsevier Inc., Amsterdam, The Netherlands (1992).

Lin, S.Y., et al., "β-catenin, a novel prognostic marker for breast cancer: its roles in cyclin D1 expression and cancer progression," *Proc. Natl. Acad. Sci. USA* 97:4262-4266, National Academy of Sciences, Washington, DC, U.S.A. (2000).

Liu, S., at al., "Interaction of hedgehog and notch pathways, and Bmi-1 in the regulation of human breast stem cell self-renewal" American Association for Cancer Research, 96th Annual Meeting, Abstract No. 2043, Apr. (2005).

Li, Y., et al., "Evidence that transgenes encoding components of the Wnt signaling pathway preferentially induce mammary cancers from progenitor cells." Proc. Nat. Acad. Sci. USA, 100:15853-8, the National Academy of Sciences, Washington, DC, U.S.A. (2003).

Lo, P.-K., et al., "Epigenetic Suppression of Secreted Frizzled Related Protein 1 (SFRP1) Expression in Human Breast Cancer," *Cancer Biology & Therapy* 5:e1-e6, Landes Bioscience, Austin, TX, U.S.A. (2006).

Lodygin, D., et al., "Functional Epigenomics Identifies Genes Frequently Silenced in Prostate Cancer," *Cancer Res.* 65:4218-4227, the American Association for Cancer Research, Philadelphia, PA, U.S. A. May (2005).

(56) References Cited

OTHER PUBLICATIONS

Lu, D., et al., "Repression of β-catenin function in malignant cells by nonsteroidal antiinflammatory drugs," *PNAS* 102:18567-18571, the National Academy of Sciences, Washington, DC, U.S.A. (Dec. 20, 2005).

Lyons, J.P., et al., "Wnt-4 activates the canonical β-catenin-mediated Wnt pathway and binds Frizzled-6 CRD: functional implications of Wnt/β-catenin activity in kidney epithelial cells," *Exp. Cell Res.* 298:369-387, Elsevier Inc., United States, Aug. (2004).

Mazieres, J., et al., "Wnt signaling in lung cancer," *Cancer Letters* 222:1-10, Elsevier Inc., Amsterdam, The Netherlands, May (2005).

Miller, J.R., et al., "Mechanism and function of signal transduction by the Wnt/β-catenin and Wnt/$Ca^{2+}$ pathways," *Oncogene* 18:7860-7872, Nature Publishing Group (1999).

Milovanovic, T., et al., "Expression of Wnt genes and frizzled 1 and 2 receptors in normal breast epithelium and infiltrating breast carcinoma," *Int. J. Oncol.* 25:1337-1342, D.A. Spandidos (Nov. 2004).

Moon, R.T., "Wnt/β-Catenin Pathway," *Sci. STKE* 271:1-3, American Association for the Advancement of Science, Washington, DC, Feb. (2005).

Morreli N.T., et al., "Liposomal Packaging Generates Wnt protein with In Vivo Biological Activity," *PLoS One* 3:1-9, e2930, Public Library of Science (PLoS), San Francisco, CA, U.S.A. (Aug. 2008).

Murdoch, B., et al., "Wnt-5A augments repopulating capacity and primitive hemaropoietic development of human blood stem cells in vivo," *PNAS* 100:3422-3427, the National Academy of Sciences, Washington, DC, U.S.A. (2003).

Nagayama, S., et al., "Therapeutic potential of antibodies against FZD10, a cell-surface protein, for synovial sarcomas," *Oncogene* 24:6201-6212, Nature Publishing Group (Sep. 2005).

Nunnally, A.P. and Parr, B.A., "Analysis of *Fz 10* expression in mouse embryos," *Dev. Genes Evol.* 214:144-148, Springer-Verlag (Mar. 2004).

Nusse, R., et al., A new nomenclature for int-1 and related genes: the Wnt gene family. Cell 64, 231, MIT Press. Cambridge U.S.A. (1991).

Nusse, R., "The Wnt gene family in tumorigenesis and in normal development," *Journal of Steroid Biochemistry & Molecular Biology* 43: 9-12, New York : Pergamon, Oxford, England (1992).

Olson, D.J. and Gibo, D.M., "Antisense *wnt*-5a Mimics *wnt*-1-Mediated C57MG Mammary Epithelial Cell Transformation," *Exp. Cell Res.* 241:134-141, Elsevier Inc., Amsterdam, The Netherlands (1998).

Oshima, H., et al., Morphological and Molecular Processes of Polyp Formation in $Apc^{\Delta716}$ Knockout Mice, *Cancer Res.* 57:1644-1649, The American Association for Cancer Research, Philadelphia, PA, U.S.A. (1997).

Patel, S., et al., "Glycogen synthase kinase-3 in insulin and Wnt signalling: a double-edged sword?" *Biochemical Society Transactions* 32:803-808, Portland Press Ltd., London, UK, Aug. (2004).

Pinto, D. and Clevers, H., "Wnt control of stem cells and differentiation in the intestinal epithelium," *Experimental Cell Research* 306:357-363, Elsevier Inc., Amsterdam, The Netherlands Jun. (2005).

Polakis, P., "Wnt signaling and cancer," *Genes & Development* 14:1837-1851, Cold Spring Harbor Laboratory Press, Woodbury NY, U.S.A. (2000).

Radtke, F. and Clevers, H., "Self-Renewal and Cancer of the Gut: Two Sides of a Coin," *Science* 307:1904-1909, The Company of Biologists Ltd, London, UK, Mar. (2005).

Reya, T., et al., "Wnt Signaling Regulates B Lymphocyte Proliferation through a LEF-1 Dependent Mechanism," *Immunity* 13:15-24 (2000).

Reya T., et al., "Stem cells, cancer, and cancer stem cells." *Nature* 414(6859):105-111, Nature Publishing Group, England (2001).

Reya, T. and Clevers, H., "Wnt signalling in stem cells and cancer," *Nature* 434:843-850, Nature Publishing Group, New York, NY, U.S. A. Apr. (2005).

Reya, T., et al., "A role for Wnt signalling in self-renewal of haematopoietic stem cells," *Nature* 423:409-414, Nature Publishing Group, New York, NY, U.S.A. (2003).

Rhee, C.S., et al., "Wnt and frizzled receptors as potential targets for immunotherapy in head and neck squamous cell carcinomas," *Oncogene* 21:6598-6605, Nature Publishing Group (2002).

Sagara, N., et al., "Molecular Cloning, Differential Expression, and Chromosomal Localization of Human *Frizzled-1*, *Frizzled-2*, and *Frizzled-7*," Biochem. Biophys. Res. Commnun. 252:117-122, Academic Press (1998).

Saitoh, T., et al., "Frequent up-regulation of WNT5A mRNA in primary gastric cancer" *Intl J Mol Med* 9:515-519 (2002).

Saitoh, T., et al., "Molecular cloning and characterization of human *Frizzled-8* gene on chromosome 10p11.2," *Int. J. Oncol.* 18:991-996, D.A. Spandidos (2001).

Saitoh, T., et al., "Up-regulation of *Frizzled-10* (FZD10) by β-estradiol in MCF-7 cells and by retinoic acid in NT2 cells," *Int. J Oncol.* 20:117-120, D.A. Spandidos (2002).

Sala, C.F., et al., "Identification, Gene Structure, and Expression of Human Frizzled-3 (*FZD3*)," *Biochem. Biophys. Res. Commun.* 273:27-34, Academic Press (2000).

Saldanha, J., et al., "Identification of a Frizzled-like cysteine rich domain in the extracellular region of developmental receptor tyrosine kinases," *Protein Science* 7:1632-1635, The Protein Society, United States (1998).

Saneyoshi, T., et al., "The Wnt/calcium pathway activates NF-AT and promotes ventral cell fate in Xenopus embryos," Nature 417:295-299, *Nature* Publishing Group, New York, NY, U.S.A. (2002).

Sagara, N., et al., "*FZD4S*, a Splicing Variant of *Frizzled-4*, Encodes a Soluble-Type Positive Regulator of the WNT Signaling Pathway," *Biochem. Biophys. Res. Commun.* 282:750-756, Academic Press, United States (2001).

Schweizer, L. and Varmus, H., "Wnt/Wingless signaling through β-catenin requires the function of both LRP/Arrow and frizzled classes of receptors," *BMC Cell Biology* 4, 11 pages, BioMed Central Ltd., London, UK (2003).

Semënov, M., et al., "SOST Is a Ligand for LRP5/LRP6 and a Wnt Signaling Inhibitor," *The Journal of Biological Chemistry* 280:26770-26775, American Society for Biochemistry and Molecular Biology, Bethesda, MD, U.S.A. May (2005).

Sen, M., et al., "Blockade of Wnt-5A/Frizzled 5 Signaling Inhibits Rheumatoid Synoviocyte Activation," *Arthritis Rheum.* 44:772-781, Wiley-Liss, Inc. (2001).

Shalary, M.R., et al., "Bispecific HER X CD3 Antibodies Enhance T-Cell Cytotoxicity in Vitro and Localize to HER2-Overexpressing Xenografts in Nude Mice," *Clin. Imm and Immunopath*, 74:185-192, Elsevier Inc., Amsterdam, The Netherlands (1995).

Skolnick, J. and Fetrow, J.S., "From genes to protein structure and function: novel applications of computational approaches in the genomic era," *Trends in Biotechnology* 18:34-39, Elsevier Inc., Amsterdam, The Netherlands (2000).

Sperger, J.M., et al., "Gene expression patterns in human embryonic stem cells and human pluripotent germ cell tumors," *PNAS* 23:13350-13355, The National Academy of Sciences of the USA, United States (2003).

Suresh, M.R. et al., "Advantages of bispecific hybridomas in one-step immunocytochemistry and immunoassays," *Neurobiology, Proceedings of the National Academy of Sciences of the United States of America*, 83:7989-7993, the National Academy of Sciences, Washington DC, USA (1986).

Suzuki, H., et al., "A genomic screen for genes unregulated by demethylation and histone deacetylase inhibition in human colorectal cancer," *Nature Genetics* 31:141-149, Nature Publishing Group, New York, NY, U.S.A. (Jun. 2002).

Suzuki, H., et al., "Epigenetic inactivation or SFRP genes allows constitutive WNT signaling in colorectal cancer," *Nature Genetics* 36:417-422, Nature Publishing Group, New York, NY, U.S.A. (Apr. 2004).

Suzuki, H., et al., "Frequent epigenetic inactivation of Wnt antagonist genes in breast cancer," *British Journal of Cancer* 98:1147-1156, Nature Publishing Group, New York, NY, U.S.A. (2008).

Tanaka, S., et al., "A novel frizzled gene identified in human esophageal carcinoma mediates APC/β-catenin signals," *Proc. Natl. Acad. Sci. U.S.A.* 95:10164-10169, National Academy of Sciences (1998).

(56) References Cited

OTHER PUBLICATIONS

Terasaki, H., et al., "*Frizzled-10*, up-regulated in primary colorectal cancer, is a positive regulator of the WNT—β-catenin—TCF signaling pathway," *Int. J Mol. Med.* 9:107-112, D.A. Spandidos (2002).

Tokuhara, M., et al., "Molecular Cloning of Human *Frizzled-6*," *Biochem. Biophys. Res. Commun.* 243:622-627, Academic Press (1998).

Topol, L., et al., "Wnt-5a inhibits the canonical Wnt pathway by promoting GSK-3-independent β-catenin degradation," *J. Cell Biol.* 162:899-908, The Rockefeller University Press, New York, NY, U.S.A. (2003).

Tosatto, S.C.E. and Toppo, S., Large-Scale Prediction of Protein Structure and Function from Sequence, *Current Pharmaceutical Design* 12:2067-2086, Bentham Science Publishers, Oak Park, IL, U.S.A. (2006).

Townsend, A. and Trowsdale, J., "The transporters associates with antigen presentation" *Seminars in Cell Biology* 4:53-61, Academic Press Limited, United States (1993).

Toyofuku, T., et al., "Wnt/frizzled-2 Signaling Induces Aggregation and Adhesion among Cardiac Myocytes by Increased Cadherin-β-Catenin Complex," *J. Cell. Biol.* 150:225-241, Rockefeller University Press (2000).

Bourhis, E., et al., "Reconstitution of a Frizzled8.Wnt3a.LRP6 Signaling Complex Reveals Multiple Wnt andDkk1 Binding Sites on LRP6," *J. Biol. Chem.* 285(12):9172-9179, American Society for Biochemistry and Molecular Biology, United States (2010).

Umbhauer, M., et al., "The C-terminal cytoplasmic Lys-thr-X-X-X-Trp motif in frizzled receptors mediates Wnt/β-catenin signalling," *The EMBO Journal* 19:4944-4954, Oxford University Press, New York, NY, U.S.A. (2000).

Unkeless, J.C., "Characterization of a Monoclonal Antibody Directed Against Mouse Macrophage and Lymphocyte Fc Receptors," *J. Exp. Med.* 150:580-596, The Rockefeller University Press, New York, NY, U.S.A. (Sep. 1979).

Unknown Author, "Purified Rat Anti-Mouse CD16/CD32 (Mouse BD Fe BlockTM)," Technical Data Sheet 553142 Rev. 16, 2 pages, BD Biosciences (date unknown), URL:http://www.bdbiosciences.com/external_files/pm/doc/tds/mouse/live/web_enabled/01241D 553142.pdf.

Üren, A., et al., "Secreted Frizzled-related Protein-1 Binds Directly to Wingless and Is a Biphasic Modulator of Wnt Signaling," *The Journal of Biological Chemistry* 275:4374-4382, American Society for Biochemistry and Molecular Biology, Bethesda, MD, U.S.A. (2000).

Uyttendaele, H., et al., "Notch4 and Wnt-1 Proteins Function to Regulate Branching Morphogeneses of Mammary Epithelial Cells in an Opposing Fashion" *Dev. Biol.* 196:204-217, Elsevier Inc., The Netherlands (1998).

Van De Vijver, M., et al., "A gene-expression signature as a predictor of survival in breast cancer" *N Eng. J Med* 347:1999-2009, Massachusetts Medical Society, Boston, MA, U.S.A. (2002).

Van De Wetering, M., et al., "The β-catenin/TCF-4 complex imposes a crypt progenitor phenotype on colorectal cancer cells," *Cell* 111:241-259, Cell Press, United States (2002).

Van Den Berg, D.J., et al., "Role of Members of the *Wnt* Gene Family in Human Hematopoiesis," *Blood* 92:3189-3202, The American Society of Hematology, Washington, DC, U.S.A. (1998).

Van Es, J.H. and Clevers, H., "Notch and Wnt inhibitors as potential new drugs for intestinal neoplastic disease," *Trends Mol. Med.* 11:496-502, Elsevier Inc., The Netherlands, Nov. (2005).

Van't Veer, L.J., et al., "Gene expression profiling predicts clinical outcome of breast cancer" *Nature* 415:530-6, the Nature Publishing Group, Basingstoke, England (2002).

Veeman, M.T., et al., "A Second Canon: Functions and Mechanisms of β-Catenin-Independent Wnt Signaling," *Dev. Cell* 5:367-377, Elsevier Inc., Amsterdam, The Netherlands (2003).

Vincan, E., et al., "Frizzled-7 receptor ectodomain expression in a colon cancer cell line induces morphological change and attenuates tumor growth," *Differentiation* 73:142-153, Blackwell (Apr. 2005).

Voronkov, A., et al., "Molecular Model of the Wnt Protein Binding Site on the Surface of Dimeric CRD Domain of the hFzd8 Receptor," *Doklady Biochemistry and Biophysics* 419:75-78, Pleiades Publishing Ltd., Russia (2008).

Wang, Y., et al., "A Large Family of Putative Transmembrane Receptors Homologous to the Product of the *Drosophila* Tissue Polarity Gene *frizzled*," J. Biol. Chem. 271:4468-4476, American Society for Biochemistry and Molecular Biology (1996).

Wang, Y-K., et al., "Characterization and Expression Pattern of the *frizzled* Gene *Fzd9*, the Mouse Homolog of *FZD9* which Is Deleted in Williams-Beuren Syndrome," *Genomics* 57:235-248, Academic Press (1999).

Wang, Z., et al., "Wnt7b Activates Canonical Signaling in Epithelial and Vascular Smooth Muscle Cells through Interactions with Fzd1, Fzd10, and LRP5," *Mol. Cell. Biol.* 25:5022-5030, American Society for Microbiology Jun. (2005).

Webb, T., "Work on Breast Cancer Stem Cells Raises Questions About Treatment Strategies," *Journal of the National Cancer Institute.* 95(11): 774-775, Jun. 4, 2003, printed online, pp. 1-5.

Weeraratna, A.T., et al., "Wnt5a signaling directly affects cell motility and invasion of metastatic melanoma," *Cancer Cell* 1:279-288, Cell Press (2002).

Willert, K. and Jones, K.A., "Wnt signaling: is the party in the nucleus?" *Genes & Development* 20:1394-1404, Cold Spring Harbor Laboratory Press, Cold Spring Harbor, NY, U.S.A. (2006).

Willert, K., et al., "Wnt proteins are lipid-modified and can act as stem cell growth factors," *Nature* 423:448-452, Nature Publishing Group, New York, NY, U.S.A. (2003).

Wnt-3a COPE, (Online 2010), accessed on Oct. 1, 2010, accessed from http://www.copewithcytokines.de/cope.cgi?key=Wnt-3a.paras 2 and 5.

Wong, N.A.C.S. and Pignatelli, M., "β-catenin—A Linchpin in Colorectal Carcinogenesis?," *Am. J. Pathol.* 160:389-401, American Society for Investigative Pathology (2002).

Wong, S.C.C., et al., "Expression of frizzled-related protein and Wnt-signalling molecules in invasive human breast tumours," *J. Pathol.* 196:145-253, Oliver & Boyd. London, UK (2002).

Woodward, W.A., et al., "WNT/β-catenin mediates radiation resistance of mouse mammary progenitor cells," *PNAS* 104:618-623, the National Academy of Sciences, Washington, DC, U.S.A. (2007).

Wu, C-H. and Nusse, R., "Ligand Receptor Interactions in the Wnt Signaling Pathway in *Drosophila*," *J. Biol. Chem.* 277:41762-41769, American Society for Biochemistry and Molecular Biology (2002).

Yamashita, J.K., et al., Prospective identification of cardiac progenitors by a novel single cell-based cardiomyocyte induction, *The FASEB Journal*, 29 pages. (Published online Jul. 20, 2005).

Yang, P., at al., "Study design considerations in clinical outcome research of lung cancer using microarray analysis" *Lung Cancer* 46:215-226, Elsevier, Amsterdam, The Netherlands, Nov. (2004).

Yang-Snyder, J., et al., "A *frizzled* homolog functions in a vertebrate *Wnt* signaling pathway," *Curr. Biol.* 6:1302-1306, Cell Press (1996).

Zeng, X., et al., "A dual-kinase mechanism for Wnt co-receptor phosphorylation and activation," *Nature* 438:873-877, Nature Publishing Group, Basingstoke, UK (Dec. 8, 2005).

Zhao, Z., et al., "A Human Homologue of the *Drosophila* Polarity Gene *frizzled* Has Been Identified and Mapped to 17q21.1," *Genomics* 27:370-373, Academic Press (1995).

Zhu, A.J.Z., et al., "β-Catenin signaling modulates proliferative potential of human epidermal keratinocytes independently of intracellular adhesion," *Development* 126: 2285-2298, The Company of Biologists Limited, Great Britain (1999).

English language Abstract of German Patent Publication No. WO 02/00576 A1, European Patent Office, espacenet database (2002).

Lepourcelet, M., et al., "Small-molecule antagonists of the oncogenic Tcf/β-catenin protein complex," *Cancer Cell* 5:91-102, Cell Press, U.S.A. Jan. (2004).

International Search Report for International Application No. PCT/US09/58635, ISA/US, Alexandria, VA, mailed on Nov. 19, 2010.

Written Opinion for International Application No. PCT/US09/58635, ISA/US, Alexandria, VA, mailed on Nov. 19, 2010.

Lu, C., et al., "The Binding Sites for Competitive Antagonistic, Allosteric Antagonistic, and Agonistic Antibodies to the I Domain of

(56) References Cited

OTHER PUBLICATIONS

Integrin LFA-1," *J. Immunol.* 173:3972-3978, American Society of Immunologists, Inc., United States Sep. (2004).

Wood, V., et al., "The genome sequence of *Schizosaccharomyces pombe*," *Nature* 415:871-880, Nature Publishing Group, United Kingdom (2002).

Decypher ClustalW Multiple Alignment, Stanford University (online, Sep. 2006), accessed on Sep. 30, 2010, accessed from http://web.archive.org/web/20060912071608/http://www2.stanford.edu/~rnusse/genealigns/mhfzalign.html>.

Polakis, P., "Evidence for Wnt Signaling in Cancers lacking Genetic Defects," PowerPoint NYAS Presentation and transcript, presented on Oct. 25, 2005, 71 pages.

International Search Report of the International Searching Authority for International Application No. PCT/US07/005443, mailed on Oct. 30, 2008, United States Patent and Trademark Office, United States, 4 pages.

Written Opinion for the International Searching Authority for International Application No. PC/US07/05443, mailed on Oct. 30, 2008, The International Bureau of WIPO, Switzerland, 4 pages.

Guyre, P.M., et al., "Increased potency of Fc-receptor-targeted antigens," *Cancer Immunol. Immunother.* 45:146-148, Springer International, New York, NY, U.S.A. (1997).

Fredriksson, R., el al., "The G-Protein-Coupled Receptors in the Human Genome Form Five Main Families. Phylogenetic Analysis, Paralogon Groups, and Fingerprints" *Mol. Pharmacol* 63.-1256-1272, The American Society for Pharmacology and Experimental Therapeutics, United States (2003).

De Gruijl, T. and Curiel, D.T., "Cancer vaccine strategies get bigger and better," *Nat. Med.* 5(10).-1124-1125, Nature Publishing Company, United States (1999).

Vajdos, F.F., et al., "Comprehensive functional maps of the antigen binding site of an anti-ErbB2 antibody obtained with shotgun scanning mutagenesis," *J. Mol. Biol.* 320:415-428, Elsevier, England (2002).

Lee, K-H., et al., "Increased vaccine specific T cell frequency after peptide based vaccination correlates with increased susceptibility to in vitro stimulation but does not lead to tumor regression," *J. Immunol.* 163(11):6292-6300, Williams & Wilkins, United States (1999).

Bodey, B., et al., "Failure of cancer vaccines: the significant limitations of this approach to immunotherapy," *Anticancer Res.* 20(4):2665-2676, International Institute of Anticancer Research, Greece (2000).

MacCallum, R.M., et al., "Antibody antigen interactions: contact analysis and binding site topography," *J. Mol. Biol.* 262(5):732-745, Elsevier, England (1996).

Casset, F., el al., "A peptide mimetic of an anti-CD4 monoclonal antibody by rational design," *Biochem. Biophys. Res. Comm.* 37:198-205, Academic Press, United States (2003).

Holm, P., et al., "Functional mapping and single chain construction of the anti-cytokeratin 8 monoclonal antibody TS1," *Mol. Immunol.* 44:1075-1084, Pergamon Press, England (2007).

Donnelly, J., "Cancer vaccine targets leukemia," *Nat. Med.* 9(11):1354-6, Nature Publishing Company, United States (2003).

Wu, H., et al., "Humanization of a murine monoclonal antibody by simultaneous optimization of framework and CDR residues," *J. Mol. Biol.* 294:151-162, Elsevier, England (1999).

Ezzel, C., "Cancer 'Vaccines': An Idea Whose Time Has Come?" *Journal of NIH Research* 7:46-49, National Institutes of Health, United States (1995).

Forni, G., el al., "Immunoprevention of Cancer: Is the Time Ripe?" *Cancer Res* 60(10):2571-2575, American Association for Cancer Research, United States (2000).

Chatterjee, M.B., et al., "Idiotypic antibody immunotherapy of cancer," *Cancer Immunol. Immunother.* 38(2):75-82, Springer International, Germany (1994).

Rudikoff, S., et al., "Single amino acid substitution altering antigen binding specificity," *Proc. Natl. Acad. Sci.* 79(6):1979-83, National Academy of Sciences, United States (1982).

International Search Report of the International Searching Authority for International Application No. PCT/US11/20994, mailed on Aug. 15, 2011, United States Patent and Trademark Office, United States, 4 pages.

Written Opinion for the International Searching Authority for International Application No. PCT/US11/20994, mailed on Aug. 15, 2011, International Searching Authority, United States, 6 pages.

Unknown Author, "Biotinylated Anti-mouse Fzd-2 Antibody," 1 page, R&D Systems, dated Feb. 11, 2004, URL:http://www.rndsystems.com/pdf/baf1307.pdf, downloaded Sep. 27, 2012.

Schulte, G. and Bryja, V., "The Frizzled family of unconventional G-protein-coupled receptors," *Trends Pharmacol Sci.* 28(10):518-25, Elsevier in Association With The International Union of Pharmacology, England (2007).

Aruffo, A., et al., "CD44 is the principal cell surface receptor for hyaluronate," *Cell* 61(7):1303-13, Cell Press, United States (1990).

"Frizzled 8 precursor (Frizled 8) (Fz-8) (hFz8)." [online], Sep. 2005, Accession Q91-1461, Retrieved on Feb. 1, 2013 from http://www.ncbi.nlm.nih.gov/protein/17433053?sat=34&satkey=5096022.

"Frizzled 4 precursor (Frizled-4) (Fz-4) (hFz4) (FzE4)." [online], Sep. 2005, Accession Q9ULV1, Retrieved on Feb. 1, 2013 from http://www.ncbi.nlm.nih.gov/protein/62298045?sat-34 &satkey=4861841.

Macleod, R.J., et al., "Wnt5a secretion stimulated by extracellular calcium-sensing receptor inhibits defective Wnt signaling in colon cancer cells," *Am. J. Physiol. Gastrointest. Liver. Physiol.* 293(1).:G403-G411, American Physiological Society, United States (2007).

Khan, N.I., et al., "Activation of Wnt/beta-catenin pathway mediates growth and survival in B-cell progenitor acute lymphoblastic leukaemia," *Br. J. Haematol.* 138(3):338-348, Wiley-Blackwell, England (2007).

You, L., et al., "Wnt-1 signal as a potential cancer therapeutic target," *Drug News Perspect.* 19(1):27-31, Thomson Reuters, United States (2006).

Katoh, Y. and Katoh, M., "Comparative genomics on Fzd8 orthologs," *Oncol. Rep.* 13(15):993-997, D.A. Spandidos, Greece Mar. (2005).

Merle, P., et al., "Functional consequences of frizzled-7 receptor overexpression in human hepatocellular carcinoma," *Gastroenterology* 127(4):1110-1122, W.B. Saunders, United States, Oct. (2004).

Gurney, A., et al., "Wnt pathway inhibition via the targeting of Frizzled receptors results in decreased growth and tumorigenicity of human tumors," *Proc. Natl. Acad. Sci. USA* 109(29):11717-22, National Academy of Sciences, United States (2012).

Luu, H.H., et al., "Wnt/β-Catenin Signaling Pathway as Novel Cancer Drug Targets," *Curr. Cancer Drug Targets* 4:653-671, Bentham Science Publishers, Netherlands, Dec. (2004).

Ueno, K., et al., "Frizzled homolog proteins, microRNAs and Wnt Signaling in cancer," *Int. J. Cancer* 132:1731-1740, Wiley-Liss, United States (2013).

Accession No. UNITPROT: A6CA06, EBI database (Jul. 24, 2007).

Accession No. GSP: AVA85292, EBI database (Apr. 2, 2009).

Accession No. GSP: ARJ99386, EBI database (May 15, 2008).

International Search Report of the International Searching Authority for International Application No. PCT/US13/66087 mailed on Jan. 16, 2014, United States Patent and Trademark Office, United States, 4 pages.

Written Opinion for the International Searching Authority for International Application No. PCT/US13/66087 mailed on Jan. 16, 2014 The International Bureau of WIPO, Switzerland, 4 pages.

Al-Hajj, M., et al., "Prospective Identification of Tumorigenic Breast Cancer Cells," Proceedings of the National Academy of Sciences 100(7):3983-3988, The National Academy of Sciences, United States (2003).

Caricasole, A., et al., "Functional Characterization of WNT7A Signaling in PC12 Cells," The Journal of Biological Chemistry 278(39):37024-37031, The American Society for Biochemistry and Molecular Biology, United States (2003).

Cong, F., et al., "Wnt Signals across the Plasma Membrane to Activate the Beta-catenin Pathway by Forming Oligomers Containing its Receptors, Frizzled and LRP," Development 131(20):5103-5115, Company of Biologists, England (2004).

(56) References Cited

OTHER PUBLICATIONS

"frizzled Antibody (H-300): sc-9169" accessed at http://scbt.com/datasheet-9169-frizzled-h-300-antibody.html, accessed on Mar. 20, 2015, 6 pages.

Gaudio, A., et al., "Increased Sclerostin Serum Levels Associated with Bone Formation and Resorption Markers in Patients with Immobilization-Induced Bone Loss," The Journal of Clinical Endocrinology and Metabolism 95(5):2248-2253, The Endocrine Society, United States (2010).

Gore, L., et al., "Safety, pharmacokinetics, and pharmacodynamics results from a phase I trial of BAY 86/9766 (RDEA119), a MEK inhibitor, in patients with advanced cancer," J Clin Oncol 29:2 pages, presented at the 2011 ASCO Annual Meeting, American Society of Clinical Oncology, United States (2011) (Abstract 3007).

International Search Report for International Application No. PCT/US14/68097, United States Patent and Trademark Office, United States, mailed on Apr. 30, 2015, 10 pages.

International Search Report for International Application No. PCT/US2012/068351, US Patent Office, Virginia, mailed on May 24, 2013, 7 pages.

International Search Report for International Application No. PCT/US2014/014443, United States Patent and Trademark Office, United States, mailed on Apr. 15, 2014, 4 pages.

Jimeno, A., et al., "A first-in-human phase 1 study of anticancer stem cell agent OMP-54F28 (FZD-Fc), decoy receptor for WNT ligands, in patient with advanced solid tumors," 2014 ASCO Annual Meeting, Abstract 2505, 2 pages (2014).

Kabacik, S., et al., "Gene Expression Following Ionising Radiation: Identification of Biomarkers for Dose Estimation and Prediction of Individual Response," International Journal of Radiation Biology 67(2):115-129, Informa Healthcare, England (2011).

Lin, S.Y. et al., "β-catenin, a novel prognostic marker for breast cancer: its roles in cyclin D1 expression and cancer progression," Proceedings of the National Academy of Sciences of the United States of America 97(8):4262-4266, National Academy of Sciences, United States (2000).

Miele, L. and Osborne, B., "Arbiter of Differentiation and Death: Notch Signaling Meets Apoptosis," Journal of Cellular Physiology 181(3):393-409, Wiley-Liss, Inc., United States (1999).

OncoMed Pharmaceuticals Press Release, "OncoMed Announces Abstracts Accepted at the 2014 ASCO Annual Meeting, " Apr. 23, 2014, 2 pages.

OncoMed Pharmaceuticals Press Release, "OncoMed Pharmaceuticals Announces FDA Clearance to Commerce Phase 1 Testing of Anti-Cancer Stem Cell Therapeutic OMP-18R5," Apr. 28, 2011, 2 pages.

OncoMed Pharmaceuticals Press Release, "OncoMed Pharmaceuticals Commences Third Phase 1b Clinical Trial for OMP-54F28 (Fzd8-fc) With Carboplatin and Paclitaxel in Ovarian Cancer," Feb. 20, 2014, 3 pages.

OncoMed Pharmaceuticals Press Release, "OnoMed Pharmaceticals Initates First Phase 1b Clinical Trial of First-in-Class WNT-Pathway-Targeting Antibody Vantictumab (OMP-18R5) With Paclitaxel in Breast Cancer," Oct. 29, 2013, 3 pages.

OncoMed Pharmaceuticals Press Release, "OncoMed Pharmaceuticals Initiates First Phase 1b Clinical Trial of OMP-54F28 (Fzd8-FC) With Nab-Paclitaxel (Abraxane(R)) and Gemcitabine in Pancreatic Center," Jan. 13, 2014, 3 pages.

OncoMed Pharmaceuticals Press Release, "OncoMed Pharmaceuticals Initiates First Phase Ib Clinical Trial of Anti-Cancer Stem Cell Therapeutic OMP-54F28 (Fzd8-FC)," Jul. 12, 2012, 2 pages.

OncoMed Pharmaceuticals Press Release, "OncoMed Pharmaceuticals Initiates Second Phase 1b Clinical Trial for OMP-54F28 (Fzd8-Fc) With Sorafenib (Nexavar(R)) in Hepatocellular Cancer," Feb. 18, 2014, 3 pages.

OncoMed Pharmaceuticals Press Release, "OncoMed Pharmaceuticals Initiates Second Phase 1b Clinical Trial of First-in-Class WNTPathway-Targeting Antibody Vantictumab (OMP-18R5) With Docetaxel in Non-Small Cell Lung Center (NSCLC)," Nov. 15, 2013, 3 pages.

OncoMed Pharmaceuticals Press Release, "OncoMed Pharmaceuticals Initiates Third Phase 1b Clinical Trial of First-in-Class WNTPathway-Targeting Antibody Vantictumab (OMP-18R5) With Nab-Paclitaxel (Abraxane®) and Gemcitabine in Stage IV Pancreatic Cancer," Dec. 4, 2013, 3 pages.

OncoMed Pharmaceuticals Press Release, "OncoMed Pharmaceuticals Presents Data From Clinical Trials of Four Novel Anti-Cancer Stem Cell (Anti-CSC) Therapeutics at the AACR-NCI-EORTC International Conference on Molecular Targets and Cancer Therapeutics in Boston, Oct. 19-23, 2013," Oct. 21, 2013, 4 pages.

OncoMed Pharmaceuticals Press Release, "OncoMed Pharmaceuticals Presents Phase 1 Data in Solid Tumor Patients for the First-in-Class Wnt Pathway Targeting Antibody Vantictumab (OMP-18R5) at ASCO," Jun. 3, 2013, 2 pages.

OncoMed Pharmaceuticals Press Release, "OncoMed Pharmaceuticals Presents Updated Phase 1a in Advanced Solid Tumor Patients for the First-in-Class WNT-Pathway-Targeting Antibody Vantictumab (OMP-18R5) at the European Cancer Congress 2013," Sep. 29, 2013, 3 pages.

OncoMed Pharmaceuticals Press Release, "OncoMed Pharmaceuticals Recaps New Data Presented at AACR," Apr. 3, 2012, 2 pages.

OncoMed Pharmaceuticals Press Release, "OncoMed Pharmaceuticals to Present Data From Clinical Trials of Four Novel Anti-Cancer Stem Cell (Anti-CSC) Therapeutics in Five Posters at the AACR-NCI-EORTC International Conference Molecular Targets and Cancer Therapeutics in Boston, Oct. 19-23, 2013," Oct. 14, 2013, 4 pages.

OncoMed Pharmaceuticals Press Release, "OncoMed Pharmaceuticals to Present Phase 1a Data in Advanced Solid Tumor Patientts for the First-in-Class WNT-Pathway-Targeting Antibody Vantictumab (OMP-18R5) at the European Cancer Congress 2013 (ECC 2013)," Sep. 23, 2013, 2 pages.

OncoMed Pharmaceuticals, Press Release, "OncoMed Presents Data on Multiple Anti-Cancer Stem Cell Programs at American Association for Cancer Research Annual Meeting," Apr. 8, 2014, 4 pages.

OncoMed Pharmaceuticals Press Release, "OncoMed Presents New Data in Six Anti-Cancer Stem Cell Programs at AACR," Apr. 9, 2013, 3 pages.

OncoMed Pharmaceuticals Prese Relase, "OncoMed Provides Update on FZD8-Fc (OMP-54F28) Phase I Clinical Trials," Jun. 18, 2014, 2 pages.

OncoMed Pharmaceuticals Press Release, "OncoMed to Present Data From Three Clinical Studies at the 2014 ASCO Annual Meeting," May 14, 2014, 4 pages.

OncoMed Pharmaceuticals Press Release, "OncoMed To Present New Data in Six Anti-Cancer Stem Cell Programs at AACR," Apr. 2, 2013, 2 pages.

OncoMed Pharmaceuticals Press Release, "PNAS Publishes OncoMed Data Demostrating Potent Anti-Cancer Activity for Novel Wnt Pathway Antibody OPM-18R5," Jul. 3, 2012, 2 pages.

Smith, D.C., et al., "A first-in-human Phase 1 study of anti-center stem cell (CSC) agent OMP-54F28 (FZD8-Fc) targeting the WNT pathway in patients with advanced solid tumors," AACR-NCI-EORTC International Conference on Molecular Targets and Cancer Therapeutics, Oct. 19-23, 2013, Abstract B79, 1 page (2013).

Smith, D.C., et al., "Biomarker analysis in the first-in-human Phase 1a study for vantictumab (OMP-18R5; anti-Frizzled) demostrates pharmacodynamics (PD) modulation of the Wnt pathway in patients with advanced solid tumors," AACR-NCI-EORTC International Conference on Molecular Targets and Cancer Therapeutics in Boston, Oct. 19-23, 2013, Poster 823, 1 page (2013).

Wheater, G., et al., "The clinical utility of bone marker measurements in osteoporosis," Journal of Translational Medicine 11(201): 11 pages, BioMed Central Ltd, England (2013).

Written Opinion for International Application No. PCT/US14/68097, United States Patent and Trademark Office, United States, mailed on Apr. 30, 2015, 25 pages.

Yen, W-C., et al., "Enhanced anti-tumor effect WNT pathway antagonists in comination with taxanes," AACR Annual Meeting 2014, Apr. 5-9, Abstract 4547, 1 page (2014).

(56) References Cited

OTHER PUBLICATIONS

Yeung, P. et al., "Wnt pathway antagonist OMP-54F28 (FZD8-Fc) inhibits tumor growth and reduces tumor-initiating cell frequency in patient-derived hepatocelluar carcinoma and ovarian cancer xenograft models," AACR Annual Meeting 2014, Apr. 5-9, Abstract 1907, 1 page (2014).

Zhang, C., et al., "Predictive biomarker identification for response to vantictumab (OMP-18R5; anti-Frizzled) by mining gene expression data of human breast cancer xenografts," AACR Annual Meeting, Apr. 5-9, Abstract 2830, 1 page (2014).

Office Action mailed Nov. 19, 2013, in U.S. Appl. No. 13/667,191, Gurney, A.L, et al., filed Nov. 2, 2012.

Office Action mailed Feb. 25, 2014, in U.S. Appl. No. 13/667,191, Gurney, A.L., et al., filed Nov. 2, 2012.

US 5,962,233, 10/1999, Livak et al. (withdrawn)

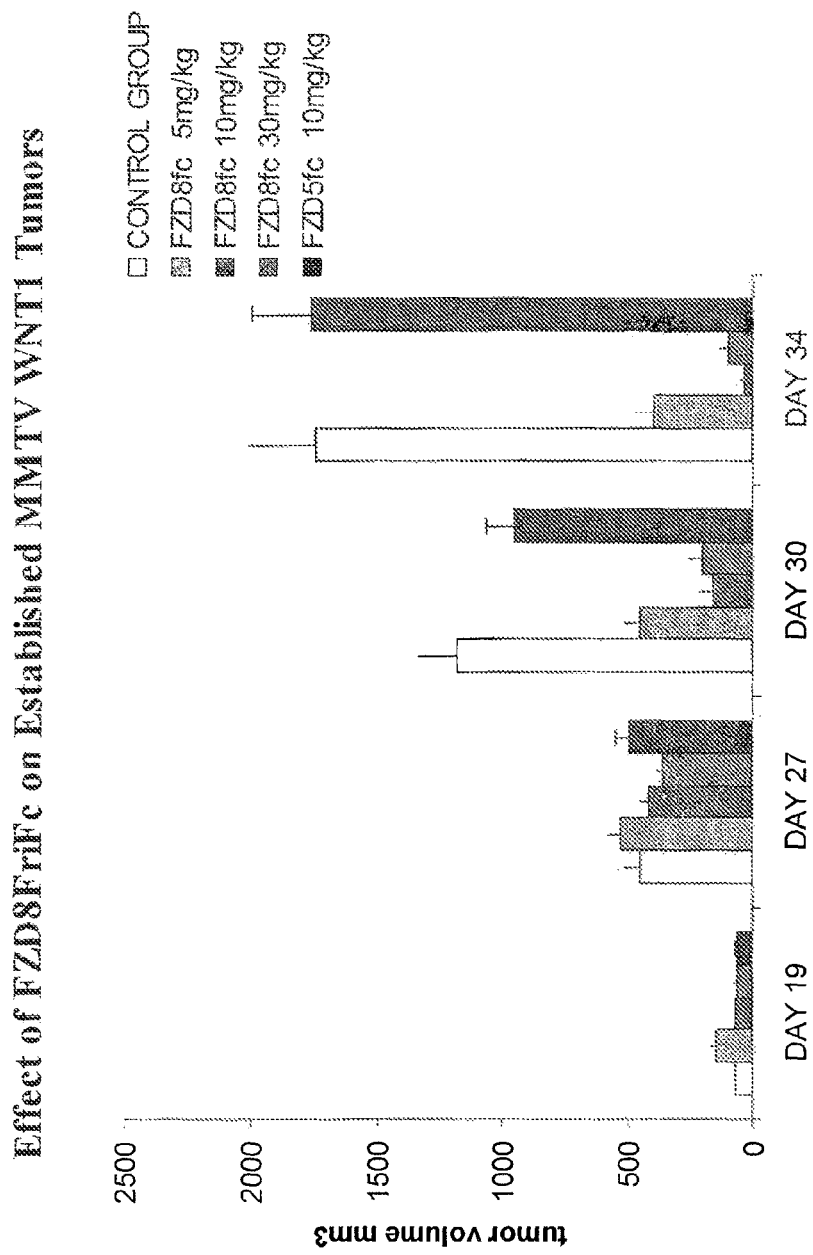

SEQUENCE LISTING

<160> NUMBER OF SEQ ID NOS: 9

<210> SEQ ID NO 1
<211> LENGTH: 227
<212> TYPE: PRT
<213> ORGANISM: Artificial Sequence

```
<220> FEATURE:
<223> OTHER INFORMATION: recombinant human FZD10 N-terminal
      extracellular domain

<400> SEQUENCE: 1

Met Gln Arg Pro Gly Pro Arg Leu Trp Leu Val Leu Gln Val Met Gly
1               5                   10                  15

Ser Cys Ala Ala Ile Ser Ser Met Asp Met Glu Arg Pro Gly Asp Gly
            20                  25                  30

Lys Cys Gln Pro Ile Glu Ile Pro Met Cys Lys Asp Ile Gly Tyr Asn
        35                  40                  45

Met Thr Arg Met Pro Asn Leu Met Gly His Glu Asn Gln Arg Glu Ala
50                  55                  60

Ala Ile Gln Leu His Glu Phe Ala Pro Leu Val Glu Tyr Gly Cys His
65                  70                  75                  80

Gly His Leu Arg Phe Phe Leu Cys Ser Leu Tyr Ala Pro Met Cys Thr
                85                  90                  95

Glu Gln Val Ser Thr Pro Ile Pro Ala Cys Arg Val Met Cys Glu Gln
            100                 105                 110

Ala Arg Leu Lys Cys Ser Pro Ile Met Glu Gln Phe Asn Phe Lys Trp
        115                 120                 125

Pro Asp Ser Leu Asp Cys Arg Lys Leu Pro Asn Lys Asn Asp Pro Asn
130                 135                 140

Tyr Leu Cys Met Glu Ala Pro Asn Asn Gly Ser Asp Glu Pro Thr Arg
145                 150                 155                 160

Gly Ser Gly Leu Phe Pro Pro Leu Phe Arg Pro Gln Arg Pro His Ser
                165                 170                 175

Ala Gln Glu His Pro Leu Lys Asp Gly Gly Pro Gly Arg Gly Gly Cys
            180                 185                 190

Asp Asn Pro Gly Lys Phe His His Val Glu Lys Ser Ala Ser Cys Ala
        195                 200                 205

Pro Leu Cys Thr Pro Gly Val Asp Val Tyr Trp Ser Arg Glu Asp Lys
210                 215                 220

Arg Phe Ala
225

<210> SEQ ID NO 2
<211> LENGTH: 255
<212> TYPE: PRT
<213> ORGANISM: Artificial Sequence
<220> FEATURE:
<223> OTHER INFORMATION: recombinant human FZD7 N-terminal extracellular
      domain

<400> SEQUENCE: 2

Met Arg Asp Pro Gly Ala Ala Ala Pro Leu Ser Ser Leu Gly Leu Cys
1               5                   10                  15

Ala Leu Val Leu Ala Leu Leu Gly Ala Leu Ser Ala Gly Ala Gly Ala
            20                  25                  30

Gln Pro Tyr His Gly Glu Lys Gly Ile Ser Val Pro Asp His Gly Phe
        35                  40                  45

Cys Gln Pro Ile Ser Ile Pro Leu Cys Thr Asp Ile Ala Tyr Asn Gln
50                  55                  60

Thr Ile Leu Pro Asn Leu Leu Gly His Thr Asn Gln Glu Asp Ala Gly
65                  70                  75                  80

Leu Glu Val His Gln Phe Tyr Pro Leu Val Lys Val Gln Cys Ser Pro
                85                  90                  95
```

```
Glu Leu Arg Phe Phe Leu Cys Ser Met Tyr Ala Pro Val Cys Thr Val
                100                 105                 110

Leu Asp Gln Ala Ile Pro Pro Cys Arg Ser Leu Cys Glu Arg Ala Arg
            115                 120                 125

Gln Gly Cys Glu Ala Leu Met Asn Lys Phe Gly Phe Gln Trp Pro Glu
130                 135                 140

Arg Leu Arg Cys Glu Asn Phe Pro Val His Gly Ala Gly Glu Ile Cys
145                 150                 155                 160

Val Gly Gln Asn Thr Ser Asp Gly Ser Gly Gly Pro Gly Gly Gly Pro
                165                 170                 175

Thr Ala Tyr Pro Thr Ala Pro Tyr Leu Pro Asp Leu Pro Phe Thr Ala
                180                 185                 190

Leu Pro Pro Gly Ala Ser Asp Gly Arg Gly Arg Pro Ala Phe Pro Phe
            195                 200                 205

Ser Cys Pro Arg Gln Leu Lys Val Pro Pro Tyr Leu Gly Tyr Arg Phe
210                 215                 220

Leu Gly Glu Arg Asp Cys Gly Ala Pro Cys Glu Pro Gly Arg Ala Asn
225                 230                 235                 240

Gly Leu Met Tyr Phe Lys Glu Glu Arg Arg Phe Ala Arg Leu
                245                 250                 255

<210> SEQ ID NO 3
<211> LENGTH: 233
<212> TYPE: PRT
<213> ORGANISM: Artificial Sequence
<220> FEATURE:
<223> OTHER INFORMATION: recombinant human FZD5 N-terminal extracellular
      domain

<400> SEQUENCE: 3

Met Ala Arg Pro Asp Pro Ser Ala Pro Pro Ser Leu Leu Leu Leu Leu
1               5                   10                  15

Leu Ala Gln Leu Val Gly Arg Ala Ala Ala Ser Lys Ala Pro Val
            20                  25                  30

Cys Gln Glu Ile Thr Val Pro Met Cys Arg Gly Ile Gly Tyr Asn Leu
            35                  40                  45

Thr His Met Pro Asn Gln Phe Asn His Asp Thr Gln Asp Glu Ala Gly
50                  55                  60

Leu Glu Val His Gln Phe Trp Pro Leu Val Glu Ile Gln Cys Ser Pro
65                  70                  75                  80

Asp Leu Arg Phe Phe Leu Cys Ser Met Tyr Thr Pro Ile Cys Leu Pro
                85                  90                  95

Asp Tyr His Lys Pro Leu Pro Pro Cys Arg Ser Val Cys Glu Arg Ala
            100                 105                 110

Lys Ala Gly Cys Ser Pro Leu Met Arg Gln Tyr Gly Phe Ala Trp Pro
            115                 120                 125

Glu Arg Met Ser Cys Asp Arg Leu Pro Val Leu Gly Arg Asp Ala Glu
130                 135                 140

Val Leu Cys Met Asp Tyr Asn Arg Ser Glu Ala Thr Thr Ala Pro Pro
145                 150                 155                 160

Arg Pro Phe Pro Ala Lys Pro Thr Leu Pro Gly Pro Pro Gly Ala Pro
                165                 170                 175

Ala Ser Gly Gly Glu Cys Pro Ala Gly Gly Pro Phe Val Cys Lys Cys
            180                 185                 190

Arg Glu Pro Phe Val Pro Ile Leu Lys Glu Ser His Pro Leu Tyr Asn
```

```
                195                 200                 205
Lys Val Arg Thr Gly Gln Val Pro Asn Cys Ala Val Pro Cys Tyr Gln
            210                 215                 220

Pro Ser Phe Ser Ala Asp Glu Arg Thr
225                 230

<210> SEQ ID NO 4
<211> LENGTH: 227
<212> TYPE: PRT
<213> ORGANISM: Homo sapiens

<400> SEQUENCE: 4

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 5
<211> LENGTH: 207
<212> TYPE: PRT
<213> ORGANISM: Artificial Sequence
<220> FEATURE:
<223> OTHER INFORMATION: recombinant human FZD6 N-terminal extracellular
      domain

<400> SEQUENCE: 5

Met Glu Met Phe Thr Phe Leu Leu Thr Cys Ile Phe Leu Pro Leu Leu
1               5                   10                  15

Arg Gly His Ser Leu Phe Thr Cys Glu Pro Ile Thr Val Pro Arg Cys
            20                  25                  30

Met Lys Met Ala Tyr Asn Met Thr Phe Phe Pro Asn Leu Met Gly His
```

```
            35                  40                  45
Tyr Asp Gln Ser Ile Ala Ala Val Glu Met Glu His Phe Leu Pro Leu
 50                  55                  60

Ala Asn Leu Glu Cys Ser Pro Asn Ile Glu Thr Phe Leu Cys Lys Ala
 65                  70                  75                  80

Phe Val Pro Thr Cys Ile Glu Gln Ile His Val Val Pro Pro Cys Arg
                 85                  90                  95

Lys Leu Cys Glu Lys Val Tyr Ser Asp Cys Lys Lys Leu Ile Asp Thr
                100                 105                 110

Phe Gly Ile Arg Trp Pro Glu Glu Leu Glu Cys Asp Arg Leu Gln Tyr
            115                 120                 125

Cys Asp Glu Thr Val Pro Val Thr Phe Asp Pro His Thr Glu Phe Leu
130                 135                 140

Gly Pro Gln Lys Lys Thr Glu Gln Val Gln Arg Asp Ile Gly Phe Trp
145                 150                 155                 160

Cys Pro Arg His Leu Lys Thr Ser Gly Gly Gln Gly Tyr Lys Phe Leu
                165                 170                 175

Gly Ile Asp Gln Cys Ala Pro Pro Cys Pro Asn Met Tyr Phe Lys Ser
                180                 185                 190

Asp Glu Leu Glu Phe Ala Lys Ser Phe Ile Gly Thr Val Ser Ile
            195                 200                 205

<210> SEQ ID NO 6
<211> LENGTH: 224
<212> TYPE: PRT
<213> ORGANISM: Artificial Sequence
<220> FEATURE:
<223> OTHER INFORMATION: recombinant human FZD N-terminal extracellular
      domain

<400> SEQUENCE: 6

Met Leu Ala Met Ala Trp Arg Gly Ala Gly Pro Ser Val Pro Gly Ala
  1               5                  10                  15

Pro Gly Gly Val Gly Leu Ser Leu Gly Leu Leu Leu Gln Leu Leu Leu
                 20                  25                  30

Leu Leu Gly Pro Ala Arg Gly Phe Gly Asp Glu Glu Arg Arg Cys
             35                  40                  45

Asp Pro Ile Arg Ile Ser Met Cys Gln Asn Leu Gly Tyr Asn Val Thr
 50                  55                  60

Lys Met Pro Asn Leu Val Gly His Glu Leu Gln Thr Asp Ala Glu Leu
 65                  70                  75                  80

Gln Leu Thr Thr Phe Thr Pro Leu Ile Gln Tyr Gly Cys Ser Ser Gln
                 85                  90                  95

Leu Gln Phe Phe Leu Cys Ser Val Tyr Val Pro Met Cys Thr Glu Lys
                100                 105                 110

Ile Asn Ile Pro Ile Gly Pro Cys Gly Gly Met Cys Leu Ser Val Lys
            115                 120                 125

Arg Arg Cys Glu Pro Val Leu Lys Glu Phe Gly Phe Ala Trp Pro Glu
130                 135                 140

Ser Leu Asn Cys Ser Lys Phe Pro Pro Gln Asn Asp His Asn His Met
145                 150                 155                 160

Cys Met Glu Gly Pro Gly Asp Glu Glu Val Pro Leu Pro His Lys Thr
                165                 170                 175

Pro Ile Gln Pro Gly Glu Glu Cys His Ser Val Gly Thr Asn Ser Asp
                180                 185                 190
```

```
Gln Tyr Ile Trp Val Lys Arg Ser Leu Asn Cys Val Leu Lys Cys Gly
            195                 200                 205

Tyr Asp Ala Gly Leu Tyr Ser Arg Ser Ala Lys Glu Phe Thr Asp Ile
210                 215                 220

<210> SEQ ID NO 7
<211> LENGTH: 158
<212> TYPE: PRT
<213> ORGANISM: Artificial Sequence
<220> FEATURE:
<223> OTHER INFORMATION: recombinant human FZD8 Fri domain

<400> SEQUENCE: 7

Met Glu Trp Gly Tyr Leu Leu Glu Val Thr Ser Leu Leu Ala Ala Leu
1               5                   10                  15

Ala Leu Leu Gln Arg Ser Ser Gly Ala Ala Ala Ser Ala Lys Glu
            20                  25                  30

Leu Ala Cys Gln Glu Ile Thr Val Pro Leu Cys Lys Gly Ile Gly Tyr
            35                  40                  45

Asn Tyr Thr Tyr Met Pro Asn Gln Phe Asn His Asp Thr Gln Asp Glu
        50                  55                  60

Ala Gly Leu Glu Val His Gln Phe Trp Pro Leu Val Glu Ile Gln Cys
65                  70                  75                  80

Ser Pro Asp Leu Lys Phe Phe Leu Cys Ser Met Tyr Thr Pro Ile Cys
                85                  90                  95

Leu Glu Asp Tyr Lys Lys Pro Leu Pro Pro Cys Arg Ser Val Cys Glu
            100                 105                 110

Arg Ala Lys Ala Gly Cys Ala Pro Leu Met Arg Gln Tyr Gly Phe Ala
        115                 120                 125

Trp Pro Asp Arg Met Arg Cys Asp Arg Leu Pro Glu Gln Gly Asn Pro
    130                 135                 140

Asp Thr Leu Cys Met Asp Tyr Asn Arg Thr Asp Leu Thr Thr
145                 150                 155

<210> SEQ ID NO 8
<211> LENGTH: 170
<212> TYPE: PRT
<213> ORGANISM: Artificial Sequence
<220> FEATURE:
<223> OTHER INFORMATION: recombinant human FZD4 Fri domain

<400> SEQUENCE: 8

Met Leu Ala Met Ala Trp Arg Gly Ala Gly Pro Ser Val Pro Gly Ala
1               5                   10                  15

Pro Gly Gly Val Gly Leu Ser Leu Gly Leu Leu Leu Gln Leu Leu Leu
            20                  25                  30

Leu Leu Gly Pro Ala Arg Gly Phe Gly Asp Glu Glu Arg Arg Cys
            35                  40                  45

Asp Pro Ile Arg Ile Ser Met Cys Gln Asn Leu Gly Tyr Asn Val Thr
        50                  55                  60

Lys Met Pro Asn Leu Val Gly His Glu Leu Gln Thr Asp Ala Glu Leu
65                  70                  75                  80

Gln Leu Thr Thr Phe Thr Pro Leu Ile Gln Tyr Gly Cys Ser Ser Gln
                85                  90                  95

Leu Gln Phe Phe Leu Cys Ser Val Tyr Val Pro Met Cys Thr Glu Lys
            100                 105                 110

Ile Asn Ile Pro Ile Gly Pro Cys Gly Gly Met Cys Leu Ser Val Lys
        115                 120                 125
```

```
Arg Arg Cys Glu Pro Val Leu Lys Glu Phe Gly Phe Ala Trp Pro Glu
        130                 135                 140

Ser Leu Asn Cys Ser Lys Phe Pro Pro Gln Asn Asp His Asn His Met
145                 150                 155                 160

Cys Met Glu Gly Pro Gly Asp Glu Glu Val
                165                 170

<210> SEQ ID NO 9
<211> LENGTH: 157
<212> TYPE: PRT
<213> ORGANISM: Artificial Sequence
<220> FEATURE:
<223> OTHER INFORMATION: recombinant human FZD5 Fri domain

<400> SEQUENCE: 9

Met Ala Arg Pro Asp Pro Ser Ala Pro Pro Ser Leu Leu Leu Leu Leu
1                   5                   10                  15

Leu Ala Gln Leu Val Gly Arg Ala Ala Ala Ser Lys Ala Pro Val
            20                  25                  30

Cys Gln Glu Ile Thr Val Pro Met Cys Arg Gly Ile Gly Tyr Asn Leu
            35                  40                  45

Thr His Met Pro Asn Gln Phe Asn His Asp Thr Gln Asp Glu Ala Gly
        50                  55                  60

Leu Glu Val His Gln Phe Trp Pro Leu Val Glu Ile Gln Cys Ser Pro
65                  70                  75                  80

Asp Leu Arg Phe Phe Leu Cys Ser Met Tyr Thr Pro Ile Cys Leu Pro
                85                  90                  95

Asp Tyr His Lys Pro Leu Pro Pro Cys Arg Ser Val Cys Glu Arg Ala
            100                 105                 110

Lys Ala Gly Cys Ser Pro Leu Met Arg Gln Tyr Gly Phe Ala Trp Pro
            115                 120                 125

Glu Arg Met Ser Cys Asp Arg Leu Pro Val Leu Gly Arg Asp Ala Glu
        130                 135                 140

Val Leu Cys Met Asp Tyr Asn Arg Ser Glu Ala Thr Thr
145                 150                 155
```

METHODS OF USING THE FRI DOMAIN OF HUMAN FRIZZLED RECEPTOR FOR INHIBITING WNT SIGNALING IN A TUMOR OR TUMOR CELL

CROSS REFERENCE TO RELATED APPLICATIONS

This application is a continuation of U.S. application Ser. No. 13/667,191, filed Nov. 2, 2012, now U.S. Pat. No. 8,765,913, which is a continuation of U.S. application Ser. No. 12/724,169, filed Mar. 15, 2010, now U.S. Pat. No. 8,324,361, which is a division of U.S. application Ser. No. 11/589,931, filed Oct. 31, 2006, now U.S. Pat. No. 7,723,477, which claims the benefit of U.S. Prov. Appl. No. 60/731,468, filed Oct. 31, 2005 and U.S. Prov. Appl. No. 60/812,966, filed Jun. 13, 2006, each of which is herein incorporated by reference.

REFERENCE TO SEQUENCE LISTING SUBMITTED ELECTRONICALLY

The content of the electronically submitted sequence listing (Name: 2159_0160007_SequenceListing.txt; Size: 17,595 bytes; and Date of Creation: May 1, 2014) filed on May 1, 2014, is incorporated herein by reference in its entirety.

BACKGROUND OF THE INVENTION

1. Field of the Invention

The present invention relates to the field of oncology and provides novel compositions and methods for diagnosing and treating cancer. In particular, the present invention provides antagonists against cancer and in particular against cancer stem cell markers including receptor fusion proteins useful for the study, diagnosis, and treatment of solid tumors.

2. Background Art

Cancer is one of the leading causes of death in the developed world, resulting in over 500,000 deaths per year in the United States alone. Over one million people are diagnosed with cancer in the U.S. each year, and overall it is estimated that more than 1 in 3 people will develop some form of cancer during their lifetime. Though there are more than 200 different types of cancer, four of them—breast, lung, colorectal, and prostate—account for over half of all new cases (Jemal et al., *Cancer J. Clin*, 53:5-26 (2003)).

Breast cancer is the most common cancer in women, with an estimate 12% of women at risk of developing the disease during their lifetime. Although mortality rates have decreased due to earlier detection and improved treatments, breast cancer remains a leading cause of death in middle-aged women. Furthermore, metastatic breast cancer is still an incurable disease. On presentation, most patients with metastatic breast cancer have only one or two organ systems affected, but as the disease progresses, multiple sites usually become involved. The most common sites of metastatic involvement are locoregional recurrences in the skin and soft tissues of the chest wall, as well as in axilla and supraclavicular areas. The most common site for distant metastasis is the bone (30-40% of distant metastasis), followed by the lungs and liver. And although only approximately 1-5% of women with newly diagnosed breast cancer have distant metastasis at the time of diagnosis, approximately 50% of patients with local disease eventually relapse with metastasis within five years. At present the median survival from the manifestation of distant metastases is about three years.

Current methods of diagnosing and staging breast cancer include the tumor-node-metastasis (TNM) system that relies on tumor size, tumor presence in lymph nodes, and the presence of distant metastases as described in the American Joint Committee on Cancer, *AJCC Cancer Staging Manual*, Philadelphia, Pa., Lippincott-Raven Publishers, 5th ed. (1997), pp 171-180, and in Harris, J R: "Staging of breast carcinoma" in Harris, J. R., et al., eds., *Breast Diseases*, Philadelphia, Lippincott (1991). These parameters are used to provide a prognosis and select an appropriate therapy. The morphologic appearance of the tumor can also be assessed but because tumors with similar histopathologic appearance can exhibit significant clinical variability, this approach has serious limitations. Finally assays for cell surface markers can be used to divide certain tumors types into subclasses. For example, one factor considered in the prognosis and treatment of breast cancer is the presence of the estrogen receptor (ER) as ER-positive breast cancers typically respond more readily to hormonal therapies such as tamoxifen or aromatase inhibitors than ER-negative tumors. Yet these analyses, though useful, are only partially predictive of the clinical behavior of breast tumors, and there is much phenotypic diversity present in breast cancers that current diagnostic tools fail to detect and current therapies fail to treat.

Prostate cancer is the most common cancer in men in the developed world, representing an estimated 33% of all new cancer cases in the U.S., and is the second most frequent cause of death (Jemal et al., *CA Cancer J. Clin*. 53:5-26 (2003)). Since the introduction of the prostate specific antigen (PSA) blood test, early detection of prostate cancer has dramatically improved survival rates, and the five year survival rate for patients with local and regional stage prostate cancers at the time of diagnosis is nearing 100%. Yet more than 50% of patients will eventually develop locally advanced or metastatic disease (Muthuramalingam et al., *Clin. Oncol*. 16:505-516 (2004)).

Currently radical prostatectomy and radiation therapy provide curative treatment for the majority of localized prostate tumors. However, therapeutic options are very limited for advanced cases. For metastatic disease, androgen ablation with luteinising hormone-releasing hormone (LHRH) agonist alone or in combination with anti-androgens is the standard treatment. Yet despite maximal androgen blockage, the disease nearly always progresses with the majority developing androgen-independent disease. At present there is no uniformly accepted treatment for hormone refractory prostate cancer, and chemotherapeutic regimes are commonly used (Muthuramalingam et al., *Clin. On col.* 16:505-516 (2004); Trojan et al., *Anticancer Res*. 25:551-561 (2005)).

Colorectal cancer is the third most common cancer and the fourth most frequent cause of cancer deaths worldwide (Weitz et al., 2005, Lancet 365:153-65). Approximately 5-10% of all colorectal cancers are hereditary with one of the main forms being familial adenomatous polyposis (PAP), an autosomal dominant disease in which about 80% of affected individuals contain a germline mutation in the adenomatous polyposis coli (APC) gene. Colorectal carcinoma has a tendency to invade locally by circumferential growth and elsewhere by lymphatic, hematogenous, transperitoneal, and perineural spread. The most common site of extralymphatic involvement is the liver, with the lungs the most frequently affected extra-abdominal organ. Other sites of hematogenous spread include the bones, kidneys, adrenal glands, and brain.

The current staging system for colorectal cancer is based on the degree of tumor penetration through the bowel wall and the presence or absence of nodal involvement. This staging system is defined by three major Duke's classifications:

Duke's A disease is confined to submucosa layers of colon or rectum; Duke's B disease has tumors that invade through the muscularis propria and may penetrate the wall of the colon or rectum; and Duke's C disease includes any degree of bowel wall invasion with regional lymph node metastasis. While surgical resection is highly effective for early stage colorectal cancers, providing cure rates of 95% in Duke's A patients, the rate is reduced to 75% in Duke's B patients and the presence of positive lymph node in Duke's C disease predicts a 60% likelihood of recurrence within five years. Treatment of Duke's C patients with a post surgical course of chemotherapy reduces the recurrence rate to 40%-50%, and is now the standard of care for these patients.

Lung cancer is the most common cancer worldwide, the third most commonly diagnosed cancer in the United States, and by far the most frequent cause of cancer deaths (Spiro et al., *Am. J. Respir. Crit. Care Med.* 166:1166-1196 (2002); Jemal et al., *CA Cancer J. Clin.* 53:5-26 (2003)). Cigarette smoking is believed responsible for an estimated 87% of all lung cancers making it the most deadly preventable disease. Lung cancer is divided into two major types that account for over 90% of all lung cancers: small cell lung cancer (SCLC) and non-small cell lung cancer (NSCLC). SCLC accounts for 15-20% of cases and is characterized by its origin in large central airways and histological composition of sheets of small cells with little cytoplasm. SCLC is more aggressive than NSCLC, growing rapidly and metastasizing early and often. NSCLC accounts for 80-85% of all cases and is further divided into three major subtypes based on histology: adenocarcinoma, squamous cell carcinoma (epidermoid carcinoma), and large cell undifferentiated carcinoma.

Lung cancer typically presents late in its course, and thus has a median survival of only 6-12 months after diagnosis and an overall 5 year survival rate of only 5-10%. Although surgery offers the best chance of a cure, only a small fraction of lung cancer patients are eligible with the majority relying on chemotherapy and radiotherapy. Despite attempts to manipulate the timing and dose intensity of these therapies, survival rates have increased little over the last 15 years (Spiro et al., *Am. J. Respir. Crit. Care Med.* 166:1166-1196 (2002)).

Cancer arises from dysregulation of the mechanisms that control normal tissue development and maintenance, and increasingly stem cells are thought to play a central role (Beachy et al., *Nature* 432:324 (2004)). During normal animal development, cells of most or all tissues are derived from normal precursors, called stem cells (Morrison et al., *Cell* 88:287-298 (1997); Morrison et al., *Curr. Opin. Immunol.* 9:216-221 (1997); Morrison et al., *Annu. Rev. Cell. Dev. Biol.* 11:35-71 (1995)). Stem cells are cell that: (1) have extensive proliferative capacity; (2) are capable of asymmetric cell division to generate one or more kinds of progeny with reduced proliferative and/or developmental potential; and (3) are capable of symmetric cell divisions for self-renewal or self-maintenance. The best-known example of adult cell renewal by the differentiation of stem cells is the hematopoietic system where developmentally immature precursors (hematopoietic stem and progenitor cells) respond to molecular signals to form the varied blood and lymphoid cell types. Other cells, including cells of the gut, breast ductal system, and skin are constantly replenished from a small population of stem cells in each tissue, and recent studies suggest that most other adult tissues also harbor stem cells, including the brain.

Solid tumors are composed of heterogeneous cell populations. For example, breast cancers are a mixture of cancer cells and normal cells, including mesenchymal (stromal) cells, inflammatory cells, and endothelial cells. Classic models of cancer hold that phenotypically distinct cancer cell populations all have the capacity to proliferate and give rise to a new tumor. In the classical model, tumor cell heterogeneity results from environmental factors as well as ongoing mutations within cancer cells resulting in a diverse population of tumorigenic cells. This model rests on the idea that all populations of tumor cells would have some degree of tumorigenic potential. (Pandis et al., *Genes, Chromosomes & Cancer* 12:122-129 (1998); Kuukasjrvi et al., *Cancer Res.* 57.1597-1604 (1997); Bonsing et al., *Cancer* 71:382-391 (1993); Bonsing et al., *Genes Chromosomes & Cancer* 82:173-183 (2000); Beerman H. et al., *Cytometry.* 12:147-154 (1991); Aubele M & Werner M, *Analyt. Cell. Path.* 19:53 (1999); Shen L et al., *Cancer Res.* 60:3884 (2000)).

An alternative model for the observed solid tumor cell heterogeneity is that solid tumors result from a "solid tumor stem cell" (or "cancer stem cell" from a solid tumor) that subsequently undergoes chaotic development through both symmetric and asymmetric rounds of cell divisions. In this stem cell model, solid tumors contain a distinct and limited (possibly even rare) subset of cells that share the properties of normal "stem cells", in that they extensively proliferate and efficiently give rise both to additional solid tumor stem cells (self-renewal) and to the majority of tumor cells of a solid tumor that lack tumorigenic potential. Indeed, mutations within a long-lived stem cell population may initiate the formation of cancer stem cells that underlie the growth and maintenance of tumors and whose presence contributes to the failure of current therapeutic approaches.

The stem cell nature of cancer was first revealed in the blood cancer, acute myeloid leukemia (AML) (Lapidot et al., *Nature* 17:645-648 (1994)). More recently it has been demonstrated that malignant human breast tumors similarly harbor a small, distinct population of cancer stem cells enriched for the ability to form tumors in immunodeficient mice. An ESA+, CD44+, CD24-/low, Lin-cell population was found to be 50-fold enriched for tumorigenic cells compared to unfractionated tumor cells (Al-Hajj et al., *PNAS* 100:3983-3988 (2003)). The ability to prospectively isolate the tumorigenic cancer cells has permitted investigation of critical biological pathways that underlie tumorigenicity in these cells, and thus promises the development of better diagnostic assays and therapeutics for cancer patients. It is toward this purpose that this invention is directed.

BRIEF SUMMARY OF THE INVENTION

In certain embodiments, the present invention provides a soluble receptor comprising a cancer stem cell marker. In certain embodiments, the soluble receptor comprises a cancer stem cell marker that binds a ligand of the cancer stem cell marker. In certain embodiments, the soluble receptor comprises a cancer stem cell marker and inhibits growth of tumor cells. In certain embodiments, the soluble receptor comprises a Fri domain of a human FZD receptor. In certain embodiments, the soluble receptor comprises a Fri domain of a human FZD receptor that binds a ligand of a human FZD receptor. In certain embodiments, the soluble receptor comprises a Fri domain of a human FZD receptor and inhibits growth of tumor cells.

In certain embodiments, the present invention provides an isolated nucleic acid molecule that encodes a soluble receptor comprising a cancer stem cell marker. In certain embodiments, the isolated nucleic acid molecule encodes a soluble receptor comprising a cancer stem cell marker that binds a ligand of the cancer stem cell marker. In certain embodiments, the isolated nucleic acid molecule encodes a soluble receptor comprising a cancer stem cell marker that inhibits growth of tumor cells. In certain embodiments, the isolated nucleic acid molecule encodes a soluble receptor comprising a Fri domain of a human FZD receptor. In certain embodiments, the isolated nucleic acid molecule encodes a soluble receptor comprising a Fri domain of a human FZD receptor that binds a ligand of a human FZD receptor. In certain embodiments, the isolated nucleic acid molecule encodes a soluble receptor comprising a Fri domain of a human FZD receptor that inhibits growth of tumor cells.

In certain embodiments, the present invention provides a method of treating cancer, the method comprising administering a soluble receptor comprising a cancer stem cell marker in an amount effective to inhibit tumor cell growth. In certain embodiments the method of treating cancer comprises administering a soluble receptor comprising a cancer stem cell marker that binds a ligand of the cancer stem cell marker in an amount effective to inhibit tumor cell growth. In certain embodiments, the method of treating cancer comprises administering a soluble receptor comprising a Fri domain of a human FZD receptor in an amount effective to inhibit tumor cell growth. In certain embodiments, the method of treating cancer comprises administering a soluble receptor comprising a Fri domain of a human FZD receptor that binds a ligand of a human FZD receptor in an amount effective to inhibit tumor cell growth.

Examples of solid tumors that can be treated using a therapeutic composition of the instant invention, for example, an antibody that binds a Fzd receptor or a receptor fusion protein that blocks ligand activation of a Fzd receptor include, but are not limited to, sarcomas and carcinomas such as, but not limited to: fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, and retinoblastoma. The invention is applicable to sarcomas and epithelial cancers, such as ovarian cancers and breast cancers.

BRIEF DESCRIPTION OF THE DRAWINGS/FIGURES

FIG. 1: Half-life of FZD.Fc Soluble Receptors. Purified Fc fusion proteins were administered i.p. to 2 mice each and blood samples were obtained at various times post-administration. FZD4 Fri.Fc, FZD5 Fri.Fc, and FZD8 Fri.Fc proteins are still present in the blood serum 72 hours post-injection, and FZD5 Fri.Fc and FZD8 Fri.Fc proteins are present in the blood serum up to 96 hours post-administration. In contrast, FZD5 ECD.Fc is undetectable in blood serum after only 24 hours (top).

Figure 2:
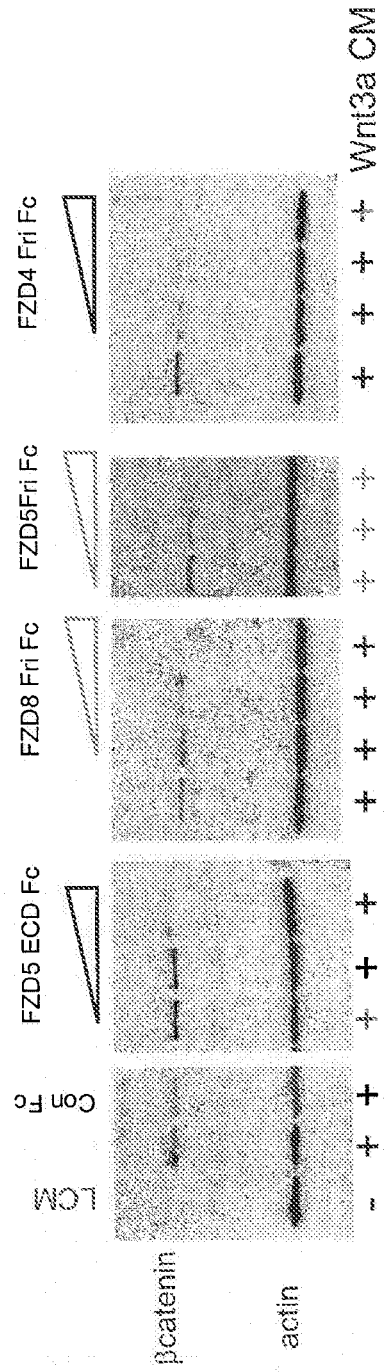

FIG. 2: FZD Fc Soluble Receptors Inhibit Wnt3a Signaling. Increasing concentrations (2 nM, 5 nM, and 60 nM) of FZD Fc fusion proteins including FZD4 Fri.Fc, FZD5 ECD.Fc, FZD5 Fri.Fc, and FZD8 Fri.Fc were incubated with L cells in the presence or absence of Wnt3a ligand and the stabilization of β-catenin was determined by immunoblotting. In the absence of Wnt3a ligand, β-catenin could not be detected (LCM). In the presence of Wnt3a β-catenin was stabilized, and this stabilization was blocked by increasing amounts of FZD5, FZD8, and FZD4 Fc soluble receptor protein but not a control Fc protein (Con Fc).

Figure 3:
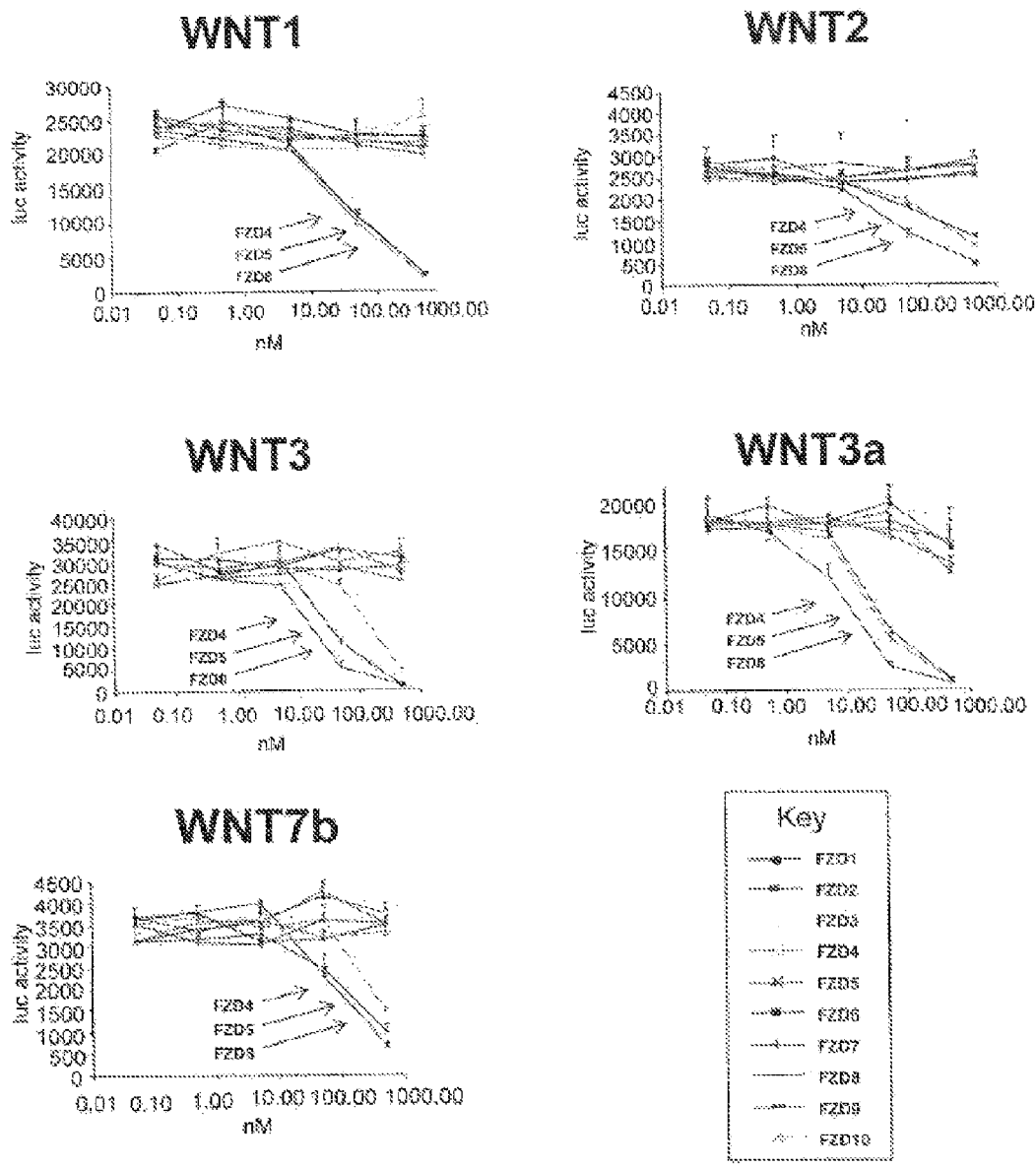

FIG. 3: FZD Fc Soluble Receptors Inhibit Wnt Signaling. Hek 293 cells stably transfected with 8×TCF-luciferase reporter were incubated with increasing concentrations of FZD:Fc soluble receptors in the presence of different Wnt ligands including Wnt1, Wnt2, Wnt3, Wnt3a and Wnt7b. FZD4 Fc, FZD5 Fc and FZD8 Fc fusion proteins inhibited Wnt signaling mediated by all five Wnt ligands as shown by loss of luciferase activity.

Figure 4:
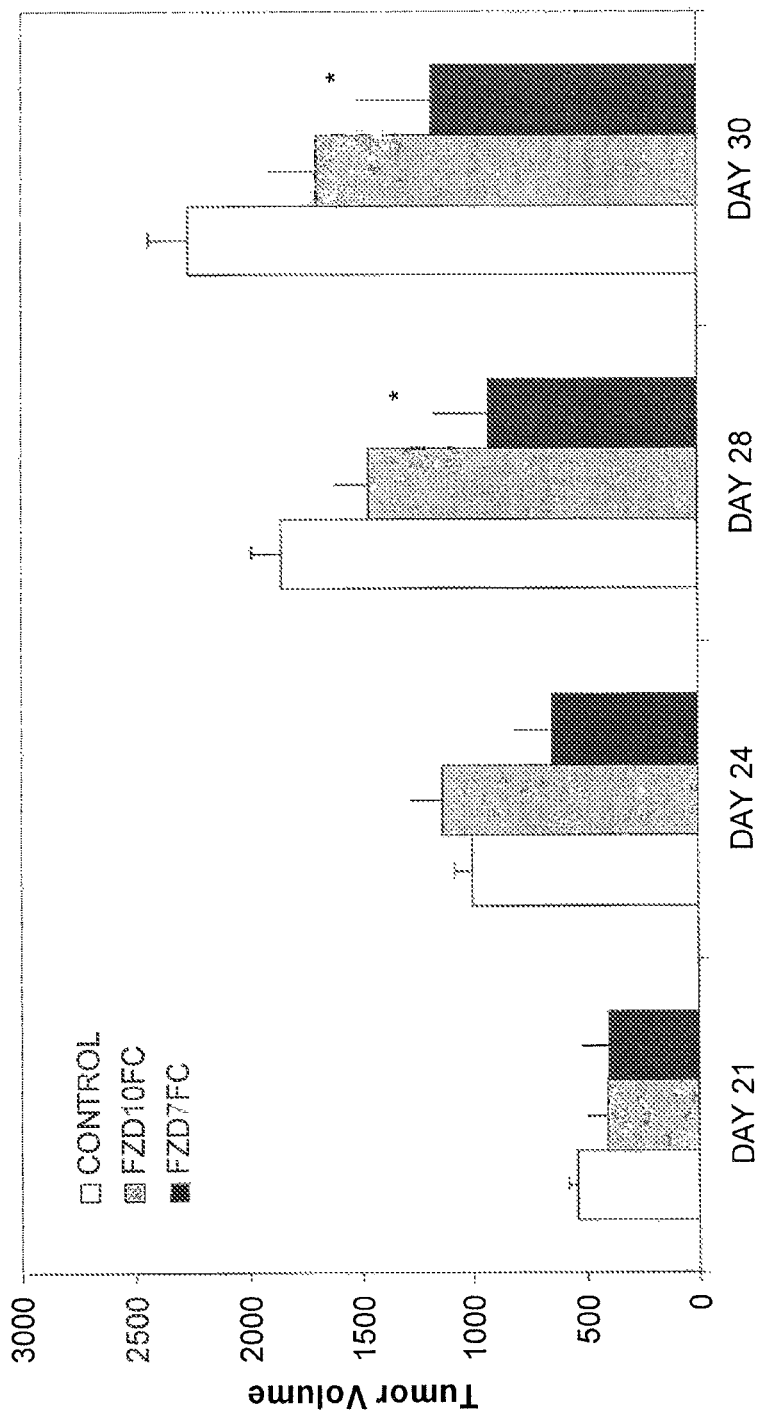

FIG. 4: Reduction of Tumor Growth by FZDFc Soluble Receptor Proteins. NOD/SOD mice injected subcutaneously with dissociated colon tumor cells (10,000 cells per animal; n=10) were treated two days later with FZD7ECD.Fc soluble receptor, FZD10ECD.Fc soluble receptor, or control injections. Total tumor volume is shown for days 21, 24, 28 and 30. The reduction of tumor volume by FZD7ECD.Fc was statistically significant on day 28 and day 30 (*).

Figure 5:
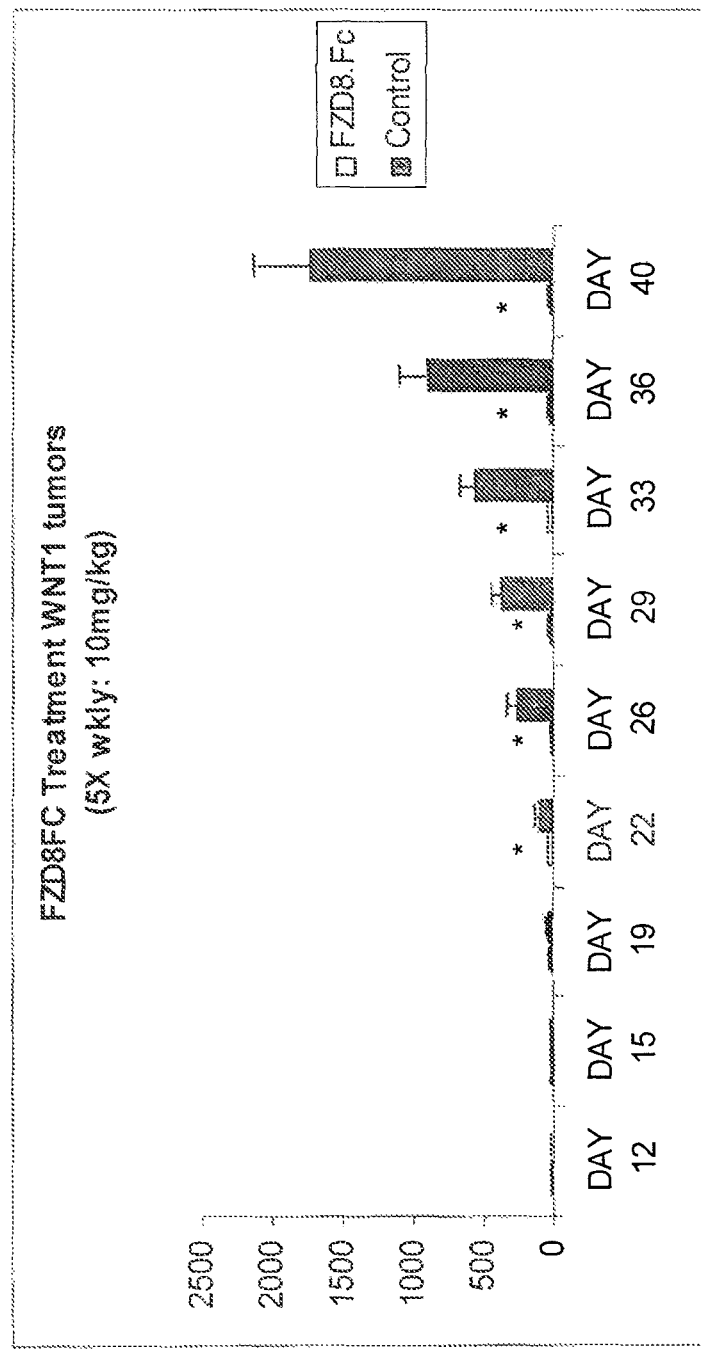

FIG. 5: Prevention of Wnt-dependent Tumor Growth by FZD8 Fri.Fc Soluble Receptor Protein. NOD/SOD mice injected with 50,000 MMTV WNT1 tumor derived cells (n=10) were the following day treated with FZD8 Fri.Fc soluble receptor or PBS as a control. Tumor growth was monitored weekly until growth was detected, then tumor growth was measured twice a week. Tumor growth in animals treated with FZD Fri.Fc (left bar) was virtually eliminated compared to that observed in control animals (right bar).

Figure 6:
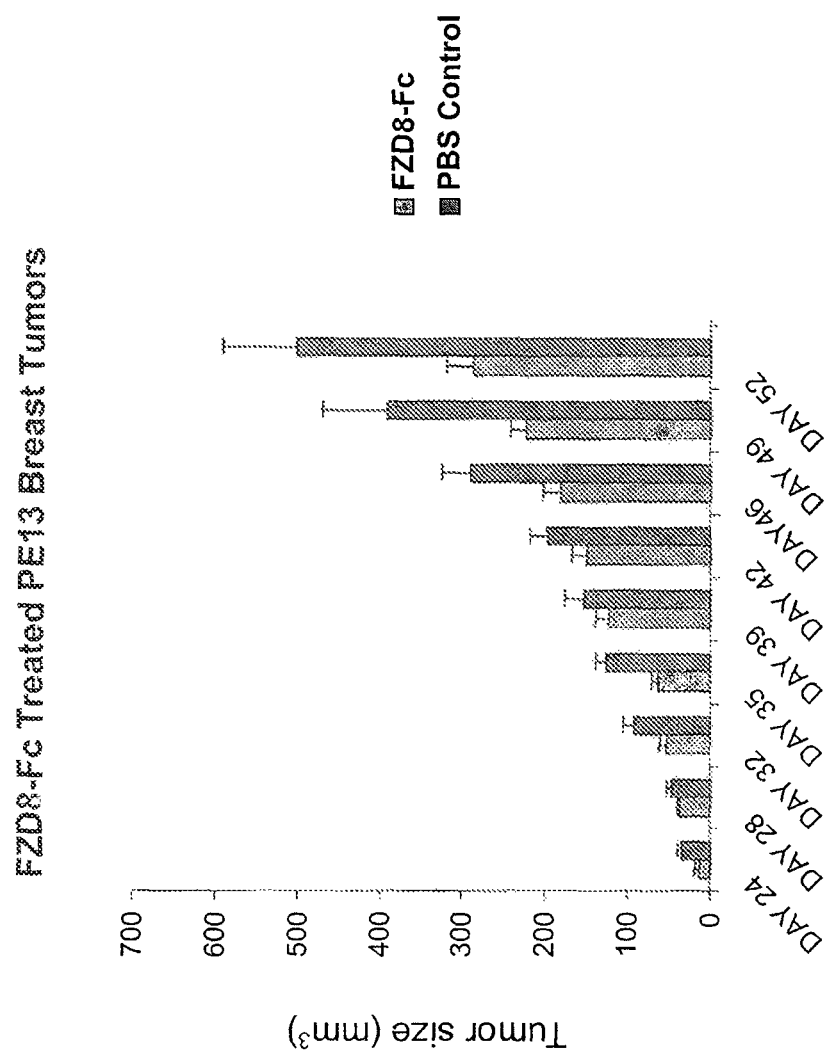

FIG. 6: Reduction of PE13 Xenograft Tumor Growth by FZD8 Fri.Fc Soluble Receptor Protein. NOD/SCID mice injected with 50,000 PE13 breast tumor cells (n=10) were the following day treated with FZD8 Fri.Fc soluble receptor or PBS as a control. Tumor growth was monitored weekly until growth was detected, then tumor growth was measured twice a week. Tumor growth in animals treated with FZD Fri.Fc (left bar) was significantly reduced compared to that observed in control animals (right bar).

FIG. 7: Treatment of Wnt-dependent Tumor Growth by FZD Fri.Fc Soluble Receptor Protein. Female rag-2/γ chain double knockout mice were implanted with 50,000 MMTV Wnt1 breast tumor derived cells. Treatment with 5 mg/kg FZD8 Fri.Fc reduced the growth of tumors, as measured by total tumor volume over time, relative to mice treated with PBS (white bars). Treatment with 10 mg/kg and 30 mg/kg FZD8 Fri.Fc was even more effective in reducing the size of the pre-established tumors. In contrast, FZD5 Fri.Fc did not display anti-tumor effects on established breast tumors that require wnt1 for growth.

DETAILED DESCRIPTION OF THE INVENTION

Definitions

The term "antagonist" is used herein to include any molecule that partially or fully blocks, inhibits, or neutralizes the expression of or the biological activity of a cancer stem cell marker disclosed herein and such biological activity includes, but is not limited to, inhibition of tumor growth. The term "antagonist" includes any molecule that partially or fully blocks, inhibits, or neutralizes a biological activity of the FZD pathway. Suitable antagonist molecules include, but are not limited to, fragments or amino acid sequence variants of native FZD receptors proteins including soluble FZD receptors.

The terms "isolated" and "purified" refer to material that is substantially or essentially free from components that normally accompany it in its native state. Purity and homogeneity are typically determined using analytical chemistry techniques such as polyacrylamide gel electrophoresis or high performance liquid chromatography. A protein (e.g. an soluble receptor) or nucleic acid that is the predominant species present in a preparation is substantially purified. In particular, an isolated nucleic acid is separated from open reading frames that naturally flank the gene and encode proteins other than protein encoded by the gene. An isolated antibody is separated from other non-immunoglobulin proteins and from other immunoglobulin proteins with different antigen binding specificity. It can also mean that the nucleic acid or protein is at least 85% pure, at least 95% pure, and in some embodiments at least 99% pure.

As used herein the terms "soluble receptor" and "FZD soluble receptor" refer to an N-terminal extracellular fragment of a human FZD receptor protein preceding the first transmembrane domain of the receptor that can be secreted from a cell in soluble form. Both FZD soluble receptors comprising the entire N-terminal extracellular domain (ECD) (referred to herein as "FZD ECD") as well as smaller fragments are envisioned. FZD soluble receptors comprising the Fri domain (referred to herein as "FZD Fri") are also disclosed. FZD Fri soluble receptors can demonstrate altered biological activity, (e.g. increased protein half-life) compared to soluble receptors comprising the entire FZD ECD. Protein half-life can be further increased by covalent modification with poly(ethylene glycol) or poly(ethylene oxide) (both referred to as PEG). FZD soluble receptors include FZD ECD or Fri domains fused in-frame to other functional and structural proteins including, but not limited to, a human Fc (e.g. human Fc derived from IgG1, IgG2, IgG3, IgG4, IgA1, IgA2, IgD, IgE, IgM); protein tags (e.g. myc, FLAG, GST); other endogenous proteins or protein fragments; or any other useful protein sequence including any linker region between a FZD ECD or Fri domain and a linked protein. In certain embodiments the Fri domain of a FZD receptor is linked to human IgG1 Fc (referred to herein as "FZD Fri.Fc"). FZD soluble receptors also include proteins with amino acid insertions, deletions, substitutions and conservative variations, etc.

As used herein, the terms "cancer" and "cancerous" refer to or describe the physiological condition in mammals in which a population of cells are characterized by unregulated cell growth. Examples of cancer include, but are not limited to, carcinoma, lymphoma, blastoma, sarcoma, and leukemia. More particular examples of such cancers include squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, vulval cancer, thyroid cancer, hepatic carcinoma and various types of head and neck cancer.

The terms "proliferative disorder" and "proliferative disease" refer to disorders associated with abnormal cell proliferation such as cancer.

"Tumor" and "neoplasm" as used herein refer to any mass of tissue that result from excessive cell growth or proliferation, either benign (noncancerous) or malignant (cancerous) including pre-cancerous lesions.

"Metastasis" as used herein refers to the process by which a cancer spreads or transfers from the site of origin to other regions of the body with the development of a similar cancerous lesion at the new location. A "metastatic" or "metastasizing" cell is one that loses adhesive contacts with neighboring cells and migrates via the bloodstream or lymph from the primary site of disease to invade neighboring body structures.

As used herein, the term "subject" refers to any animal (e.g., a mammal), including, but not limited to humans, non-human primates, rodents, and the like, which is to be the recipient of a particular treatment. Typically, the terms "subject" and "patient" are used interchangeably herein in reference to a human subject.

The terms "cancer stem cell", "tumor stem cell", or "solid tumor stem cell" are used interchangeably herein and refer to a population of cells from a solid tumor that: (1) have extensive proliferative capacity; (2) are capable of asymmetric cell division to generate one or more kinds of differentiated progeny with reduced proliferative or developmental potential; and (3) are capable of symmetric cell divisions for self-renewal or self-maintenance. These properties of "cancer stem cells", "tumor stem cells" or "solid tumor stem cells" confer on those cancer stem cells the ability to form palpable tumors upon serial transplantation into an immunocompromised mouse compared to the majority of tumor cells that fail to form tumors. Tumor cells, i.e. non-tumorigenic cells may form a tumor upon transplantation a limited number of times (e.g. one or two times) after obtaining the tumor cells from a solid tumor but will not retain the capacity to form palpable tumors on serial transplantation into an immunocompromised mouse. Cancer stem cells undergo self-renewal versus differentiation in a chaotic manner to form tumors with abnormal cell types that can change over time as mutations occur. The solid tumor stem cells of the present invention differ from the "cancer stem line" provided by U.S. Pat. No. 6,004,528. In that patent, the "cancer stem line" is defined as a slow growing progenitor cell type that itself has few mutations but which undergoes symmetric rather than asymmetric cell divisions as a result of tumorigenic changes that occur in the cell's environment. This "cancer stem line" hypothesis thus proposes that highly mutated, rapidly proliferating tumor cells arise largely as a result of an abnormal environment, which causes relatively normal stem cells to accumulate and then undergo mutations that cause them to become tumor cells. U.S. Pat. No. 6,004,528 proposes that such a model can be used to enhance the diagnosis of cancer. The solid tumor stem cell model is fundamentally different than the "cancer stem line" model and as a result exhibits utilities not offered by the "cancer stem line" model. First, solid tumor stem cells are not "mutationally spared". The "mutationally spared cancer stem line" described by U.S. Pat. No. 6,004,528 can be considered a pre-cancerous lesion, while the solid tumor stem cells described by this invention are cancer cells that themselves contain the mutations that are responsible for tumorigenesis. That is, the solid tumor stem cells ("cancer stem cells") of the invention would be included among the highly mutated cells that are distinguished from the "cancer stem line" in U.S. Pat. No. 6,004,528. Second, the genetic mutations that lead to cancer can be largely intrinsic within the solid tumor stem cells as well as being environmental. The solid tumor stem cell model predicts that isolated solid tumor stem cells can give rise to additional tumors upon transplantation (thus explaining metastasis) while the "cancer stem line" model would predict that transplanted "cancer stem line" cells would not be able to give rise to a new tumor, since it was their abnormal environment that was tumorigenic. Indeed, the ability to transplant dissociated, and phenotypically isolated human solid tumor stem cells to mice (into an environment that is very different from the normal tumor environment), where they still form new tumors, distinguishes the present invention from the "cancer stem line" model. Third, solid tumor stem cells likely divide both symmetrically and asymmetrically, such that symmetric cell division is not an obligate property. Fourth, solid tumor stem cells can divide rapidly or slowly, depending on many variables, such that a slow proliferation rate is not a defining characteristic.

The terms "cancer cell", "tumor cell" and grammatical equivalents refer to the total population of cells derived from a tumor including both non-tumorigenic cells, which comprise the bulk of the tumor cell population, and tumorigenic stem cells also referred to herein as cancer stem cells.

As used herein "tumorigenic" refers to the functional features of a solid tumor stem cell including the properties of self-renewal (giving rise to additional tumorigenic cancer stem cells) and proliferation to generate all other tumor cells (giving rise to differentiated and thus non-tumorigenic tumor cells) that allow solid tumor stem cells to form a tumor. These properties of self-renewal and proliferation to generate all other tumor cells confer on the cancer stem cells of this invention the ability to form palpable tumors upon serial transplantation into an immunocompromised mouse compared to the majority of tumor cells that are unable to form tumors upon the serial transplantation. Tumor cells, i.e. non-tumorigenic tumor cells, may form a tumor upon transplantation into an immunocompromised mouse a limited number of times (for example one or two times) after obtaining the tumor cells from a solid tumor.

As used herein, the terms "stem cell cancer marker(s)", "cancer stem cell marker(s)", "tumor stem cell marker(s)", or "solid tumor stem cell marker(s)" refer to a gene or genes or a protein, polypeptide, or peptide expressed by the gene or genes whose expression level, alone or in combination with other genes, is correlated with the presence of tumorigenic cancer cells compared to non-tumorigenic cells. The correlation can relate to either an increased or decreased expression of the gene (e.g. increased or decreased levels of mRNA or the peptide encoded by the gene).

As used herein, the terms "unfractionated tumor cells", "presorted tumor cells", "bulk tumor cells", and their grammatical equivalents are used interchangeably to refer to a tumor cell population isolated from a patient sample (e.g. a tumor biopsy or pleural effusion) that has not been segregated, or fractionated, based on cell surface marker expression.

As used herein, the terms "non-ESA+CD44+ tumor cells", "non-ESA+44+", "sorted non-tumorigenic tumor cells", "non-tumorigenic tumor cells," "non-stem cells," "tumor cells" and their grammatical equivalents are used interchangeably to refer to a tumor population from which the cancer stem cells of this invention have been segregated, or removed, based on cell surface marker expression.

As used herein, the terms "biopsy" and "biopsy tissue" refer to a sample of tissue or fluid that is removed from a subject for the purpose of determining if the sample contains cancerous tissue. In some embodiments, biopsy tissue or fluid is obtained because a subject is suspected of having cancer. The biopsy tissue or fluid is then examined for the presence or absence of cancer.

As used herein an "acceptable pharmaceutical carrier" refers to any material that, when combined with an active ingredient of a pharmaceutical composition such as an antibody, allows the antibody, for example, to retain its biological activity. In addition, an "acceptable pharmaceutical carrier" does not trigger an immune response in a recipient subject. Examples include, but are not limited to, any of the standard pharmaceutical carriers such as a phosphate buffered saline solution, water, and various oil/water emulsions. Examples of diluents for aerosol or parenteral administration are phosphate buffered saline or normal (0.9%) saline.

The term "therapeutically effective amount" refers to an amount of a soluble receptor, or other drug effective to "treat" a disease or disorder in a subject or mammal. In the case of cancer, the therapeutically effective amount of the drug can reduce the number of cancer cells; reduce the tumor size; inhibit or stop cancer cell infiltration into peripheral organs; inhibit or stop tumor metastasis; inhibit and stop tumor growth; and/or relieve to some extent one or more of the symptoms associated with the cancer. To the extent the drug prevents growth and/or kills existing cancer cells, it can be referred to as cytostatic and/or cytotoxic.

As used herein the term "inhibit tumor growth" refers to any mechanism by which tumor cell growth can be inhibited. In certain embodiments tumor cell growth is inhibited by slowing proliferation of tumor cells. In certain embodiments tumor cell growth is inhibited by halting proliferation of tumor cells. In certain embodiments tumor cell growth is inhibited by killing tumor cells. In certain embodiments tumor cell growth is inhibited by inducing apoptosis of tumor cells. In certain embodiments tumor cell growth is inhibited by depriving tumor cells of nutrients. In certain embodiments tumor cell growth is inhibited by preventing migration of tumor cells. In certain embodiments tumor cell growth is inhibited by preventing invasion of tumor cells.

As used herein, "providing a diagnosis" or "diagnostic information" refers to any information that is useful in determining whether a patient has a disease or condition and/or in classifying the disease or condition into a phenotypic category or any category having significance with regards to the prognosis of or likely response to treatment (either treatment in general or any particular treatment) of the disease or condition. Similarly, diagnosis refers to providing any type of diagnostic information, including, but not limited to, whether a subject is likely to have a condition (such as a tumor), information related to the nature or classification of a tumor as for example a high risk tumor or a low risk tumor, information related to prognosis and/or information useful in selecting an appropriate treatment. Selection of treatment can include the choice of a particular chemotherapeutic agent or other treatment modality such as surgery or radiation or a choice about whether to withhold or deliver therapy.

As used herein, the terms "providing a prognosis", "prognostic information", or "predictive information" refer to providing information regarding the impact of the presence of cancer (e.g., as determined by the diagnostic methods of the present invention) on a subject's future health (e.g., expected morbidity or mortality, the likelihood of getting cancer, and the risk of metastasis).

Terms such as "treating", "treatment", "to treat", "alleviating", and "to alleviate" refer to both 1) therapeutic measures that cure, slow down, lessen symptoms of and/or halt progression of a diagnosed pathologic condition or disorder and 2) prophylactic or preventative measures that prevent or slow the development of a targeted pathologic condition or disorder. Thus those in need of treatment include those already with the disorder; those prone to have the disorder; and those in whom the disorder is to be prevented. A subject is successfully "treated", according to the methods of the present invention if the patient shows one or more of the following: a reduction in the number of or complete absence of cancer cells; a reduction in the tumor size; inhibition of or an absence of cancer cell infiltration into peripheral organs including the spread of cancer into soft tissue and bone; inhibition of or an absence of tumor metastasis; inhibition or an absence of tumor growth; relief of one or more symptoms associated with the specific cancer; reduced morbidity and mortality; and improvement in quality of life.

As used herein, the terms "polynucleotide" and "nucleic acid" refer to a polymer composed of a multiplicity of nucleotide units (ribonucleotide or deoxyribonucleotide or related structural variants) linked via phosphodiester bonds, including but not limited to, DNA or RNA. The teen encompasses sequences that include any of the known base analogs of DNA and RNA including, but not limited to, 4 acetylcytosine, 8-hydroxy-N6-methyladenosine, aziridinylcytosine, pseudoisocytosine, 5 (carboxyhydroxyl-methyl) uracil, 5-fluorouracil, 5 bromouracil, 5-carboxymethylaminomethyl 2 thiouracil, 5 carboxymethyl-aminomethyluracil, dihydrouracil, inosine, N6 isopentenyladenine, 1 methyladenine, 1-methylpseudouracil, 1 methylguanine, 1 methyl inosine, 2,2-dimethyl-guanine, 2 methyladenine, 2 methylguanine, 3-methyl-cytosine, 5 methylcytosine, N6 methyladenine, 7 methylguanine, 5 methylaminomethyluracil, 5-methoxy-amino-methyl 2 thiouracil, beta D mannosylqueosine, 5' methoxycarbonylmethyluracil, 5 methoxyuracil, 2 methylthio N6 isopentenyladenine, uracil 5 oxyacetic acid methylester, uracil 5 oxyacetic acid, oxybutoxosine, pseudouracil, queosine, 2 thiocytosine, 5-methyl-2 thiouracil, 2-thiouracil, 4 thiouracil, 5-methyluracil, N-uracil 5 oxyacetic acid methylester, uracil 5 oxyacetic acid, pseudouracil, queosine, 2-thiocytosine, and 2,6 diaminopurine.

The term "gene" refers to a nucleic acid (e.g., DNA) molecule that comprises coding sequences necessary for the production of a polypeptide, precursor, or RNA (e.g., rRNA, tRNA). The polypeptide can be encoded by a full length coding sequence or by any portion of the coding sequence so long as the desired activity or functional properties (e.g., enzymatic activity, ligand binding, signal transduction, immunogenicity, etc.) of the full-length or fragment are retained. The term also encompasses the coding region of a structural gene and the sequences located adjacent to the coding region on both the 5' and 3' ends for a distance of about 1 kb or more on either end such that the gene corresponds to the length of the full-length mRNA. Sequences located 5' of the coding region and present on the mRNA are referred to as 5' non-translated sequences. Sequences located 3' or downstream of the coding region and present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (hnRNA); introns can contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide. In addition to containing introns, genomic forms of a gene can also include sequences located on both the 5' and 3' end of the sequences that are present on the RNA transcript. These sequences are referred to as "flanking" sequences or regions (these flanking sequences are located 5' or 3' to the non-translated sequences present on the mRNA transcript). The 5' flanking region can contain regulatory sequences such as promoters and enhancers that control or influence the transcription of the gene. The 3' flanking region can contain sequences that direct the termination of transcription, post transcriptional cleavage and polyadenylation.

The term "recombinant" when used with reference to a cell, nucleic acid, protein or vector indicates that the cell, nucleic acid, protein or vector has been modified by the introduction of a heterologous nucleic acid or protein, the alteration of a native nucleic acid or protein, or that the cell is derived from a cell so modified. Thus, e.g., recombinant cells express genes that are not found within the native (non-recombinant) form of the cell or express native genes that are overexpressed or otherwise abnormally expressed such as, for example, expressed as non-naturally occurring fragments or splice variants. By the term "recombinant nucleic acid" herein is meant nucleic acid, originally formed in vitro, in general, by the manipulation of nucleic acid, e.g., using polymerases and endonucleases, in a form not normally found in nature. In this manner, operably linkage of different sequences is achieved. Thus an isolated nucleic acid molecule, in a linear form, or an expression vector formed in vitro by ligating DNA molecules that are not normally joined, are both considered recombinant for the purposes of this invention. It is understood that once a recombinant nucleic acid molecule is made and introduced into a host cell or organism, it will replicate non-recombinantly, i.e., using the in vivo cellular machinery of the host cell rather than in vitro manipulations; however, such nucleic acids, once produced recombinantly, although subsequently replicated non-recombinantly, are still considered recombinant for the purposes of the invention. Similarly, a "recombinant protein" is a protein made using recombinant techniques, i.e., through the expression of a recombinant nucleic acid molecule as depicted above.

As used herein, the term "heterologous gene" refers to a gene that is not in its natural environment. For example, a heterologous gene includes a gene from one species introduced into another species. A heterologous gene also includes a gene native to an organism that has been altered in some way (e.g., mutated, added in multiple copies, linked to non-native regulatory sequences, etc). Heterologous genes are distinguished from endogenous genes in that the heterologous gene sequences are typically joined to DNA sequences that are not found naturally associated with the gene sequences in the chromosome or are associated with portions of the chromosome not found in nature (e.g., genes expressed in loci where the gene is not normally expressed).

As used herein, the term "vector" is used in reference to nucleic acid molecules that transfer DNA segment(s) from one cell to another. The term "vehicle" is sometimes used interchangeably with "vector." Vectors are often derived from plasmids, bacteriophages, or plant or animal viruses.

"Ligation" refers to the process of forming phosphodiester bonds between two double stranded nucleic acid fragments. Unless otherwise provided, ligation can be accomplished using known buffers and conditions with 10 units to T4 DNA ligase ("ligase") per 0.5 ug of approximately equimolar amounts of the DNA fragments to be ligated. Ligation of nucleic acid can serve to link two proteins together in-frame to produce a single protein, or fusion protein.

As used herein, the term "gene expression" refers to the process of converting genetic information encoded in a gene into RNA (e.g., mRNA, rRNA, tRNA, or snRNA) through "transcription" of the gene (e.g., via the enzymatic action of an RNA polymerase), and for protein encoding genes, into protein through "translation" of mRNA. Gene expression can be regulated at many stages in the process. "Up-regulation" or "activation" refers to regulation that increases the production of gene expression products (e.g., RNA or protein), while "down-regulation" or "repression" refers to regulation that decrease production. Molecules (e.g., transcription factors) that are involved in up-regulation or down-regulation are often called "activators" and "repressors," respectively.

The terms "polypeptide," "peptide," "protein", and "protein fragment" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers.

The term "amino acid" refers to naturally occurring and synthetic amino acids, as well as amino acid analogs and amino acid mimetics that function similarly to the naturally occurring amino acids. Naturally occurring amino acids are those encoded by the genetic code, as well as those amino acids that are later modified, e.g., hydroxyproline, gamma-carboxyglutamate, and O-phosphoserine. Amino acid analogs refers to compounds that have the same basic chemical structure as a naturally occurring amino acid, e.g., an alpha carbon that is bound to a hydrogen, a carboxyl group, an amino group, and an R group, e.g., homoserine, norleucine, methionine sulfoxide, methionine methyl sulfonium. Such analogs can have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions similarly to a naturally occurring amino acid.

"Conservatively modified variants" applies to both amino acid and nucleic acid sequences. "Amino acid variants" refers to amino acid sequences. With respect to particular nucleic acid sequences, conservatively modified variants refers to those nucleic acids which encode identical or essentially identical amino acid sequences, or where the nucleic acid does not encode an amino acid sequence, to essentially identical or associated (e.g., naturally contiguous) sequences. Because of the degeneracy of the genetic code, a large number of functionally identical nucleic acids encode most proteins. For instance, the codons GCA, GCC, GCG and GCU all encode the amino acid alanine. Thus, at every position where an alanine is specified by a codon, the codon can be altered to another of the corresponding codons described without altering the encoded polypeptide. Such nucleic acid variations are "silent variations," which are one species of conservatively modified variations. Every nucleic acid sequence herein which encodes a polypeptide also describes silent variations of the nucleic acid. One of ordinary skill will recognize that in certain contexts each codon in a nucleic acid (except AUG, which is ordinarily the only codon for methionine, and TGG, which is ordinarily the only codon for tryptophan) can be modified to yield a functionally identical molecule. Accordingly, silent variations of a nucleic acid which encodes a polypeptide is implicit in a described sequence with respect to the expression product, but not with respect to actual probe sequences. As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" including where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention. Typically conservative substitutions include: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)).

The term "epitope tagged" as used herein refers to a chimeric polypeptide comprising a cancer stem cell marker protein, or a domain sequence or portion thereof, fused to an "epitope tag". The epitope tag polypeptide comprises enough amino acid residues to provide an epitope for recognition by an antibody, yet is short enough such that it does not interfere with the activity of the cancer stem cell marker protein. Suitable epitope tags generally have at least six amino acid residues, usually between about 8 to about 50 amino acid residues, or about 10 to about 20 residues. Commonly used epitope tags include Fc, HA, His, and FLAG tags.

As used herein, "about" refers to plus or minus 10% of the indicated number. For example, "about 10%" indicates a range of 9% to 11%.

Detailed Description

The present invention provides compositions and methods for studying, diagnosing, characterizing, and treating cancer. In particular, the present invention provides antagonists against solid tumor stem cell markers and methods of using these antagonists to inhibit tumor growth and treat cancer in human patients. Antagonists include soluble receptor proteins comprising cancer stem cell markers. In certain embodiments, the present invention provides a soluble receptor comprising a Fri domain of a human FZD receptor that inhibits growth of tumor cells. In certain embodiments, the soluble receptor comprises the Fri domain of human FZD4. In certain embodiments, the soluble receptor comprises the Fri domain of human FZD4 comprising the amino acid sequence of SEQ ID NO: 8. In certain embodiments, the soluble receptor comprises the Fri domain of human FZD4 linked in-frame to a non-FZD receptor protein sequence. In certain embodiments, the soluble receptor comprises the Fri domain of human FZD4 linked in-frame to human Fe. In certain embodiments, the soluble receptor comprises the Fri domain of human FZD4 linked in-frame to human IgG$_1$ Fc. In certain embodiments, the soluble receptor comprises the Fri domain of human FZD4 linked in-frame to human IgG$_1$ Fc comprising an amino acid sequence shown in SEQ ID NO: 4.

In certain embodiments, the soluble receptor comprises the Fri domain of human FZD5. In certain embodiments, the soluble receptor comprises the Fri domain of human FZD5 comprising the amino acid sequence of SEQ ID NO: 9. In certain embodiments, the soluble receptor comprises the Fri domain of human FZD5 linked in-frame to a non-FZD receptor protein sequence. In certain embodiments, the soluble receptor comprises the Fri domain of human FZD5 linked in-frame to human Fc. In certain embodiments, the soluble receptor comprises the Fri domain of human FZD5 linked in-frame to human IgG$_1$ Fc. In certain embodiments, the soluble receptor comprises the Fri domain of human FZD5 linked in-frame to human IgG$_1$ Fc comprising an amino acid sequence shown in SEQ ID NO: 4.

In certain embodiments, the soluble receptor comprises the Fri domain of human FZD8. In certain embodiments, the soluble receptor comprises the Fri domain of human FZD8 comprising the amino acid sequence of SEQ ID NO: 7. In certain embodiments, the soluble receptor comprises the Fri domain of human FZD8 linked in-frame to a non-FZD receptor protein sequence. In certain embodiments, the soluble receptor comprises the Fri domain of human FZD8 linked in-frame to human Fc. In certain embodiments, the soluble receptor comprises the Fri domain of human FZD8 linked in-frame to human $IgG_1$ Fc. In certain embodiments, the soluble receptor comprises the Fri domain of human FZD8 linked in-frame to human $IgG_1$ Fc comprising an amino acid sequence shown in SEQ ID NO: 4.

In certain embodiments, the present invention provides an isolated nucleic acid encoding a soluble receptor comprising: a nucleic acid sequence encoding a Fri domain of human FZD4 comprising an amino acid sequence shown in SEQ ID NO: 8; and a nucleic acid sequence encoding human $IgG_1$ Fc comprising an amino acid sequence shown in SEQ ID NO: 4. In certain embodiment, the present invention provides a vector comprising the nucleic acid sequence encoding a Fri domain of human FZD4 comprising an amino acid sequence shown in SEQ ID NO: 8; and the nucleic acid sequence encoding human $IgG_1$ Fc comprising an amino acid sequence shown in SEQ ID NO: 4. In certain embodiments the vector is operably linked to control sequences recognized by a host cell transformed with the vector. In certain embodiments, the present invention provides an isolated host cell comprising the vector comprising the nucleic acid sequence encoding a Fri domain of human FZD4 comprising an amino acid sequence shown in SEQ ID NO: 8; and the nucleic acid sequence encoding human $IgG_1$ Fc comprising an amino acid sequence shown in SEQ ID NO: 4.

In certain embodiments, the present invention provides an isolated nucleic acid molecule encoding a soluble receptor comprising: a nucleic acid sequence encoding a Fri domain of human FZD5 comprising an amino acid sequence shown in SEQ ID NO: 9; and a nucleic acid sequence encoding human $IgG_1$ Fc comprising an amino acid sequence shown in SEQ ID NO: 4. In certain embodiments, the present invention provides a vector comprising the nucleic acid sequence encoding a Fri domain of human FZD5 comprising an amino acid sequence shown in SEQ ID NO: 9; and the nucleic acid sequence encoding human $IgG_1$ Fc comprising an amino acid sequence shown in SEQ ID NO: 4. In certain embodiments the vector is operably linked to control sequences recognized by a host cell transformed with the vector. In certain embodiments, the present invention provides an isolated host cell comprising the vector comprising the nucleic acid sequence encoding a Fri domain of human FZD5 comprising an amino acid sequence shown in SEQ ID NO: 9; and the nucleic acid sequence encoding human $IgG_1$ Fc comprising an amino acid sequence shown in SEQ ID NO: 4.

In certain embodiments, the present invention provides an isolated nucleic acid molecule encoding a soluble receptor comprising: a nucleic acid sequence encoding a Fri domain of human FZD8 comprising an amino acid sequence shown in SEQ ID NO: 7; and a nucleic acid sequence encoding human $IgG_1$ Fc comprising an amino acid sequence shown in SEQ ID NO: 4. In certain embodiment, the present invention provides a vector comprising the nucleic acid sequence encoding a Fri domain of human FZD8 comprising an amino acid sequence shown in SEQ ID NO: 7; and the nucleic acid sequence encoding human $IgG_1$ Fc comprising an amino acid sequence shown in SEQ ID NO: 4. In certain embodiments the vector is operably linked to control sequences recognized by a host cell transformed with the vector. In certain embodiments, the present invention provides an isolated host cell comprising the vector comprising the nucleic acid sequence encoding a Fri domain of human FZD8 comprising an amino acid sequence shown in SEQ ID NO: 7; and the nucleic acid sequence encoding human $IgG_1$ Fc comprising an amino acid sequence shown in SEQ ID NO: 4.

In certain embodiments, the present invention provides a pharmaceutical composition comprising a soluble receptor. In certain embodiments, the pharmaceutical composition comprises a soluble receptor comprising the Fri domain of a human FZD receptor. In certain embodiments the pharmaceutical composition comprises a soluble receptor comprising the Fri domain of human FZD4 receptor. In certain embodiments the pharmaceutical composition comprises a soluble receptor comprising the Fri domain of human FZD5 receptor. In certain embodiments, the pharmaceutical composition comprises a soluble receptor comprising the Fri domain of human FZD8 receptor.

In certain embodiments, the present invention provides a method of treating cancer comprising administering a soluble receptor comprising a Fri domain of a human FZD receptor in an amount effective to inhibit tumor cell growth. In certain embodiments a method of treating cancer comprises administering a soluble receptor comprising a Fri domain of human FZD4 receptor in an amount effective to inhibit tumor cell growth. In certain embodiments a method of treating cancer comprises administering a soluble receptor comprising a Fri domain of human FZD5 receptor in an amount effective to inhibit tumor cell growth. In certain embodiments a method of treating cancer comprises administering a soluble receptor comprising a Fri domain of human FZD8 receptor in an amount effective to inhibit tumor cell growth.

In certain embodiments the method of treating cancer comprises administering a soluble receptor comprising the Fri domain of a human FZD receptor linked in-frame to a non-FZD receptor protein sequence in an amount effective to inhibit tumor cell growth. In certain embodiments the method of treating cancer comprises administering a soluble receptor comprising the Fri domain of a human FZD receptor linked in-frame to a human Fc in an amount effective to inhibit tumor cell growth. In certain embodiments the method of treating cancer comprises administering a soluble receptor comprising the Fri domain of a human FZD receptor linked in-frame to human $IgG_1$ Fc in an amount effective to inhibit tumor cell growth. In certain embodiments the method of treating cancer comprises administering a soluble receptor comprising the Fri domain of a human FZD receptor linked in-frame to human $IgG_1$ Fc comprising as amino acid sequence shown in SEQ ID NO: 4 in an amount effective to inhibit tumor cell growth.

In certain embodiments, the present invention provides a method of treating cancer comprises administering a soluble receptor comprising the Fri domain of a human FZD receptor in an amount effective to inhibit tumor cell growth in combination with radiation therapy. In certain embodiments the method of treating cancer comprises administering a soluble receptor comprising the Fri domain of a human FZD receptor in an amount effective to inhibit tumor cell growth in combination with chemotherapy. In certain embodiments the method of treating cancer comprising administering a soluble receptor comprising the Fri domain of a human FZD receptor in an amount effective to inhibit tumor cell growth of tumor cells from a breast tumor, colorectal tumor, lung tumor, pancreatic tumor, prostate tumor, or a head and neck tumor.

Stem Cells and Solid Tumor Stem Cells

Common cancers arise in tissues that contain a subpopulation of proliferating cells that are responsible for replenishing the short-lived mature cells. In such organs, cell maturation is arranged in a hierarchy in which a rare population of stem cells give rise both to the more differentiated cells and perpetuate themselves through a process called self renewal (Akashi & Weissman, *Developmental Biology of Hematopoiesis*, Oxford Univ. Press, NY (2001); Spangrude et al., *Science* 241:58-61 (1988); Baum et al., *PNAS* 89:2804-2808 (1992); Morrison et al., *PNAS* 92:10302-20306 (1995); Morrison et al., *Immunity* 5:207-216 (1996); Morrison et al., *Annu. Rev. Cell Dev. Biol.* 11:35-71 (1995); Morrison et al., *Dev.* 124:1929-1939 (1997); Morrison & Weissman, *Immunity* 1:661 (1994); Morrison et al., *Cell* 88:287-298 (1997); Uchida et al., *PNAS* 97: 14720-14725 (2000); Morrison et al., *Cell* 101:499-510 (2000)). Although it is likely that most tissues contain stem cells, due to their rarity these cells have been rigorously identified and purified to study their biological, molecular, and biochemical properties in only a few tissues. The best characterized stem cells are those that give rise to the hematopoietic system, called hematopoietic stem cells (HSCs). The utility of HSCs has been demonstrated in cancer therapy with their extensive use for bone marrow transplantation to regenerate the hematolymphoid system following myeloablative protocols (Baum et al., *Bone Marrow Transplantation*, Blackwell Scientific Publications, Boston (1994)). Understanding the cellular biology of the tissues in which cancers arise, and specifically of the stem cells residing in those tissues, promises to provide new insights into cancer biology.

Like the tissues in which they originate, solid tumors consist of a heterogeneous population of cells. That the majority of these cells lack tumorigenicity suggested that the development and maintenance of solid tumors also relies on a small population of stem cells (i.e., tumorigenic cancer cells) with the capacity to proliferate and efficiently give rise both to additional tumor stem cells (self-renewal) and to the majority of more differentiated tumor cells that lack tumorigenic potential (i.e., non-tumorigenic cancer cells). The concept of cancer stem cells was first introduced soon after the discovery of HSC and was established experimentally in acute myelogenous leukemia (AML) (Park et al., *J. Natl. Cancer Inst.* 46:411-422 (1971); Lapidot et al., *Nature* 367:645-648 (1994); Bonnet & Dick, Nat. Med. 3:730-737 (1997); Hope et al., *Nat. Immunol.* 5:738-743 (2004)). Stem cells from solid tumors have more recently been isolated based on their expression of a unique pattern of cell-surface receptors and on the assessment of their properties of self-renewal and proliferation in culture and in xenograft animal models. An ESA+ CD44+ CD24−/low Lineage-population greater than 50-fold enriched for the ability to form tumors relative to unfractionated tumor cells was discovered (Al-Hajj et al., *PNAS* 100: 3983-3988 (2003)). The ability to isolate tumorigenic cancer stem cells from the bulk of non-tumorigenic tumor cells has led to the identification of cancer stem cell markers, genes with differential expression in cancer stem cells compared to non-tumorigenic tumor cells or normal breast epithelium, using microarray analysis. The present invention employs the knowledge of these identified cancer stem cell markers to study, characterize, diagnosis and treat cancer.

Cancer Stem Cell Marker Protein

Normal stem cells and cancer stem cells share the ability to proliferate and self-renew, thus is not surprising that a number of genes that regulate normal stem cell development contribute to tumorigenesis (reviewed in Reya et al., *Nature* 414: 105-111 (2001) and Taipale & Beachy, *Nature* 411:349-354 (2001)). The present invention identifies Fzd receptor, including for example, Fzd4, Fzd5, and Fzd8 as markers of cancer stem cells, implicating the Wnt signaling pathway in the maintenance of cancer stem cells and as a target for treating cancer via the elimination of these tumorigenic cells.

The Wnt signaling pathway is one of several critical regulators of embryonic pattern formation, post-embryonic tissue maintenance, and stem cell biology. More specifically, Wnt signaling plays an important role in the generation of cell polarity and cell fate specification including self-renewal by stem cell populations. Unregulated activation of the Wnt pathway is associated with numerous human cancers where it can alter the developmental fate of tumor cells to maintain them in an undifferentiated and proliferative state. Thus carcinogenesis can proceed by usurping homeostatic mechanisms controlling normal development and tissue repair by stem cells (reviewed in Reya & Clevers, *Nature* 434:843 (2005); Beachy et al., *Nature* 432:324 (2004)).

The Wnt signaling pathway was first elucidated in the *Drosophila* developmental mutant wingless (wg) and from the murine proto-oncogene int-1, now Wnt1 (Nusse & Varmus, *Cell* 31:99-109 (1982); Van Ooyen & Nusse, *Cell* 39:233-240 (1984); Cabrera et al., *Cell* 50:659-663 (1987); Rijsewijk et al., *Cell* 50:649-657 (1987)). Wnt genes encode secreted lipid-modified glycoproteins of which 19 have been identified in mammals. These secreted ligands activate a receptor complex consisting of a Frizzled (Fzd) receptor family member and low-density lipoprotein (LDL) receptor-related protein 5 or 6 (LPR5/6). The Fzd receptors are seven transmembrane domain proteins of the G-protein coupled receptor (GPCR) superfamily and contain a large extracellular N-terminal ligand binding domain with 10 conserved cysteines, known as a cysteine-rich domain (CRD) or Fri domain. There are ten human FZD receptors: FZD1-10. Different Fzd CRDs have different binding affinities for specific Wnts (Wu & Nusse, *J. Biol. Chem.* 277:41762-41769 (2002)), and Fzd receptors have been grouped into those that activate the canonical β-catenin pathway and those that activate non-canonical pathways described below (Miller et al., *Oncogene* 18:7860-7872 (1999)). LRP5/6 are single pass transmembrane proteins with four extracellular EGF-like domains separated by six YWTD amino acid repeats that contribute to Fzd and ligand binding (Johnson et al., *J Bone Mineral Res* 19:1749 (2004)).

The canonical Wnt signaling pathway activated upon receptor binding is mediated by the cytoplasmic protein Dishevelled (Dsh) interacting directly with the Fzd receptor and results in the cytoplasmic stabilization and accumulation of β-catenin. In the absence of a Wnt signal, β-catenin is localized to a cytoplasmic destruction complex that includes the tumor suppressor proteins adenomatous polyposis coli (APC) and auxin. These proteins function as critical scaffolds to allow glycogen synthase kinase (GSK)-3β to bind and phosphorylate β-catenin, marking it for degradation via the ubiquitin/proteasome pathway. Activation of Dsh results in phosphorylation of GSK3β and the dissociation of the destruction complex. Accumulated cytoplasmic β-catenin is then transported into the nucleus where it interacts with the DNA-binding proteins of the Tcf/Lef family to activate transcription.

In addition to the canonical signaling pathway, Wnt ligands also activate β-catenin-independent pathways (Veeman et al., *Dev. Cell* 5:367-377 (2003)). Non-canonical Wnt signaling has been implicated in numerous processes but most convincingly in gastrulation movements via a mechanism similar to the *Drosophila* planar cell polarity (PCP) pathway. Other potential mechanisms of non-canonical Wnt signaling include calcium flux, JNK, and both small and heterotrimeric G-proteins. Antagonism is often observed between the canonical and non-canonical pathways, and some evidence indicates that non-canonical signaling can suppress cancer formation (Olson & Gibo, *Exp. Cell Res.* 241:134 (1998); Topol et al., *J. Cell Biol.* 162:899-908 (2003)).

Hematopoietic stem cells (HSCs) are the best understood stem cells in the body, and Wnt signaling is implicated both in their normal maintenance as well as in leukemic transformation (Reya & Clevers, 2005, Nature 434:843). HSCs are a rare population of cells that reside in a stomal niche within the adult bone marrow. These cells are characterized both by a unique gene expression profile as well as an ability to continuously give rise to more differentiated progenitor cells to reconstitute the entire hematopoietic system. Both HSCs and the cells of their stromal microenvironment express Wnt ligands, and Wnt reporter activation is present in HSCs in vivo. Furthermore, both β-catenin and purified Wnt3A promote self-renewal of murine HSCs in vitro and enhance their ability to reconstitute the hematopoietic system in vivo while Wnt5A promotes expansion of human hematopoietic progenitors in vitro and re-population in a NOD-SCID xenotransplant model (Reya et al., *Nature* 423:409-414 (2003); Willert et al., *Nature* 423:448-452 (2003); Van Den Berg et al., *Blood* 92:3189-3202 (1998); Murdoch et al., *PNAS* 100:3422-3427 (2003)).

More recently Wnt signaling has been found to play a role in the oncogenic growth of both myeloid and lymphoid lineages. For example, granulocyte-macrophage progenitors (GMPs) from chronic myelogenous leukemias display activated Wnt signaling on which they are depended for growth and renewal (Jamieson et al., *N. Engl. J. Med.* 351:657-667 (2004)) And while leukemias do not appear to harbor mutations within the Wnt pathway, autocrine and/or paracrine Wnt signaling can sustain cancerous self-renewal (Reya & Clevers, *Nature* 434:843 (2005)).

The canonical Wnt signaling pathway also plays a central role in the maintenance of stem cell populations in the small intestine and colon, and the inappropriate activation of this pathway plays a prominent role in colorectal cancers (Reya & Clevers, *Nature* 434:843 (2005)). The absorptive epithelium of the intestines is arranged into villi and crypts. Stem cells reside in the crypts and slowly divide to produce rapidly proliferating cells which give rise to all the differentiated cell populations that move up out of the crypts to occupy the intestinal villi. The Wnt signaling cascade plays a dominant role in controlling cell fates along the crypt-villi axis and is essential for the maintenance of the stem cell population. Disruption of Wnt signaling either by genetic loss of Tcf7/2 by homologous recombination (Korinek et al., *Nat. Genet.* 19:379 (1998)) or overexpression of Dickkopf-1 (Dkk1), a potent secreted Wnt antagonist (Pinto et al., *Genes Dev.* 17:1709-1713 (2003); Kuhnert et al., *PNAS* 101:266-271 (2004)), results in depletion of intestinal stem cell populations.

Colorectal cancer is most commonly initiated by activating mutations in the Wnt signaling cascade. Approximately 5-10% of all colorectal cancers are hereditary with one of the main forms being familial adenomatous polyposis (FAP), an autosomal dominant disease in which about 80% of affected individuals contain a germline mutation in the adenomatous polyposis coli (APC) gene. Mutations have also been identified in other Wnt pathway components including auxin and β-catenin. Individual adenomas are clonal outgrowths of epithelial cell containing a second inactivated allele, and the large number of FAP adenomas inevitably results in the development of adenocarcinomas through addition mutations in oncogenes and/or tumor suppressor genes. Furthermore, activation of the Wnt signaling pathway, including gain-of-function mutations in APC and β-catenin, can induce hyperplastic development and tumor growth in mouse models (Oshima et al., *Cancer Res.* 57:1644-1649 (1997); Harada et al., *EMBO J.* 18:5931-5942 (1999)).

A role for Wnt signaling in cancer was first uncovered with the identification of Wnt1 (originally int1) as an oncogene in mammary tumors transformed by the nearby insertion of a murine virus (Nusse & Varmus, *Cell* 31:99-109 (1982)). Additional evidence for the role of Wnt signaling in breast cancer has since accumulated. For instance, transgenic overexpression of β-catenin in the mammary glands results in hyperplasias and adenocarcinomas (Imbert et al., *J. Cell Biol.* 153:555-568 (2001); Michaelson & Leder, *Oncogene* 20:5093-5099 (2001)) whereas loss of Wnt signaling disrupts normal mammary gland development (Tepera et al., *J. Cell Sc.* 116:1137-1140 (2003); Hatsell et al., *J. Mammary Gland Biol. Neoplasia* 8:145-158 (2003)). More recently mammary stem cells have been shown to be activated by Wnt signaling (Liu et al., *PNAS* 101:4158 (2004)). In human breast cancer, β-catenin accumulation implicates activated Wnt signaling in over 50% of carcinomas, and though specific mutations have not been identified, upregulation of Frizzled receptor expression has been observed (Brennan & Brown, *J. Mammary Gland Neoplasia* 9:119-131 (2004); Malovanovic et al., *Int. J. Oncol.* 25:1337-1342 (2004)).

FZD10, FZD8, FZD7, FZD4, and FZD5 are five of ten identified human Wnt receptors. In the mouse embryo Fzd10 is expressed with Wnt7a in the neural tube, limb buds, and Mullerian duct (Nunnally & Parr, *Dev. Genes Evol.* 214:144-148 (2004)) and can act as a receptor for Wnt-7a during limb bud development (Kawakami et al., *Dev. Growth Differ.* 42:561-569 (2000)). Fzd10 is co-expressed with Wnt7b in the lungs, and cell transfection studies have demonstrated that the Fzd10/LRP5 co-receptor activates the canonical Wnt signaling pathway in response to Wnt7b (Wang et al., *Mol. Cell Biol.* 25:5022-5030 (2005)). FZD10 mRNA is upregulated in numerous cancer cell lines, including cervical, gastric, and glioblastoma cell lines, and in primary cancers including approximately 40% of primary gastric cancers, colon cancers, and synovial sarcomas (Saitoh et al., *Int. J. Oncol.* 20:117-120 (2002); Terasaki et al., *Int. J. Mol, Med.* 9:107-112 (2002); Nagayama et al., *Oncogene* 1-12 (2005)). FZD8 is upregulated in several human cancer cell lines, primary gastric cancers, and renal carcinomas (Saitoh et al., *Int. J. Oncol.* 18:991-996 (2001); Kirikoshi et al., *Int. J. Oncol.* 19:111-115 (2001); Janssens et al., *Tumor Biol.* 25:161-171 (2004)). FZD7 is expressed throughout the gastrointestinal tract and is up-regulated in one out of six cases of human primary gastric cancer (Kirikoshi et al., *Int. J. Oncol.* 19:111-115 (2001)). Expression of the FZD7 ectodomain by a colon cancer cell line induced morphological changes and decreased tumor growth in a xenograft model (Vincan et al., *Differentiation* 73:142-153 (2005)). FZD5 plays an essential role in yolk sac and placental angiogenesis (Ishikawa et al., *Dev.* 128:25-33 (2001)) and is upregulated in renal carcinomas in association with activation of Wnt/β-catenin signaling (Janssens et al., *Tumor Biology* 25:161-171 (2004)). FZD4 is highly expressed in intestinal crypt epithelial cells and is one of several factors that display differential expression in normal versus neoplastic tissue (Gregorieff et al., *Gastroenterology* 129:626-638 (2005)). The identification of FZD4, 5, 7, 8, and 10 as markers of cancer stem cells thus makes these proteins ideal targets for cancer therapeutics.

Diagnostic Assays

The present invention provides a cancer stem cell marker the expression of which can be analyzed to detect, characterize, diagnosis or monitor a disease associated with expression of a cancer stem cell marker. In certain embodiments, expression of a cancer stem cell marker is determined by polynucleotide expression such as, for example, mRNA encoding the cancer stem cell marker. The polynucleotide can be detected and quantified by any of a number of means well known to those of skill in the art. In some embodiments, mRNA encoding a cancer stem cell marker is detected by in situ hybridization of tissue sections from, from example, a patient biopsy. Alternatively, RNA can be isolated from a tissue and detected by, for example, Northern blot, quantitative RT-PCR or microarrays. For example, total RNA can be extracted from a tissue sample and primers that specifically hybridize and amplify a cancer stem cell marker can be used to detect expression of a cancer stem cell marker polynucleotide using RT-PCR.

In certain embodiments, expression of a cancer stem cell marker can be determined by detection of the corresponding polypeptide. The polypeptide can be detected and quantified by any of a number of means well known to those of skill in the art. In some embodiments, a cancer stem cell marker polypeptide is detected using analytic biochemical methods such as, for example, electrophoresis, capillary electrophoresis, high performance liquid chromatography (HPLC) or thin layer chromatography (TLC). The isolated polypeptide can also be sequenced according to standard techniques. In some embodiments, a cancer stem cell marker protein is detected with antibodies raised against the protein using, for example, immunofluorescence or immunohistochemistry on tissue sections. Alternatively antibodies against a cancer stem cell marker can detect expression using, for example, ELISA, FACS, Western blot, immunoprecipitation or protein microarrays. For example, cancer stem cells can be isolated from a patient biopsy and expression of a cancer stem cell marker protein detected with fluorescently labeled antibodies using FACS. In another method, the cells expressing a cancer stem cell marker can be detected in vivo using labeled antibodies typical imaging system. For example, antibodies labeled with paramagnetic isotopes can be used for magnetic resonance imaging (MRI).

In some embodiments of the present invention, a diagnostic assay comprises determining the expression or not of a cancer stem cell marker in tumor cells using, for example, immunohistochemistry, in situ hybridization, or RT-PCR. In other embodiments, a diagnostic assay comprises determining expression levels of a cancer stem cell marker using, for example, quantitative RT-PCR. In some embodiments, a diagnostic assay further comprises determining expression levels of a cancer stem cell marker compared to a control tissue such as, for example, normal epithelium.

Detection of a cancer stem cell marker expression can then be used to provide a prognosis. A prognosis can be based on any known risk expression of a cancer stem cell marker can indicate. Furthermore, detection of a cancer stem cell marker can be used to select an appropriate therapy including, for example, treatment with an antagonist against the detected cancer stem cell marker. In some embodiments, the antagonist is an antibody that specifically binds to the extracellular domain of a cancer stem cell marker protein.

Cancer Stem Cell Marker Antagonists

In the context of the present invention, a suitable antagonist is an agent that can have one or more of the following effects, for example: interfere with the expression of a cancer stem cell marker; interfere with activation of a cancer stem cell signal transduction pathway by, for example, sterically inhibiting interactions between a cancer stem cell marker and its ligand, receptor or co-receptors; or bind to a cancer stem cell marker and trigger cell death or inhibit tumor cell proliferation.

In certain embodiments, the present invention provides antagonists against a cancer stem cell marker that act extracellularly to affect or inhibit the function of a cancer stem cell marker. In certain embodiments, an antagonist is a small molecule that binds to the extracellular domain of a cancer stem cell marker protein. In other embodiments, an antagonist of a cancer stem cell marker is proteinaceous. In some embodiments the proteinaceous antagonist is a fragment or amino acid sequence variant of a native cancer stem cell marker receptor or binding partner. In some embodiments the fragment or amino acid sequence variant can bind a cancer stem cell marker receptor to enhance or prevent binding of a signaling ligand. In other embodiments the fragment or amino acid sequence variant of a native cancer stem cell marker or binding partners can bind to the signaling ligand of a cancer stem cell marker to enhance or prevent binding of the signaling ligand. In some embodiments the antagonist is a soluble cancer stem cell protein receptor or soluble receptor protein. Extracellular binding of an antagonist against a cancer stem cell marker can inhibit the signaling of a cancer stem cell marker protein by inhibiting intrinsic activation (e.g. kinase activity) of a cancer stem cell marker and/or by sterically inhibiting the interaction, for example, of a cancer stem cell marker with its ligand, of a cancer stem cell marker with its receptor, of a cancer stem cell marker with a co-receptor, or of a cancer stem cell marker with the extracellular matrix. Furthermore, extracellular binding of an antagonist against a cancer stem cell marker can downregulate cell-surface expression of a cancer stem cell marker such as, for example, by internalization of a cancer stem cell marker protein and/or decreasing cell surface trafficking of a cancer stem cell marker.

In certain embodiments, antagonists of a cancer stem cell marker can trigger cell death indirectly by inhibiting angiogenesis. Angiogenesis is the process by which new blood vessels form from pre-existing vessels and is a fundamental process required for normal growth, for example, during embryonic development, wound healing and in response to ovulation. Solid tumor growth larger than 1-2 $mm^2$ also requires angiogenesis to supply nutrients and oxygen without which tumor cells die. Thus in certain embodiments, an antagonist of a cancer stem cell marker targets vascular cells that express the cancer stem cell marker including, for example, endothelial cells, smooth muscle cells or components of the extracellular matrix required for vascular assembly. In some embodiments, an antagonist of a cancer stem cell marker inhibits growth factor signaling required by vascular cell recruitment, assembly, maintenance or survival.

Polynucleotides

The invention is directed to isolated polynucleotides encoding the polypeptides comprising SEQ ID NOS: 1-9. The polynucleotides of the invention can be in the form of RNA or in the form of DNA with DNA including cDNA, genomic DNA, and synthetic DNA. The DNA can be double-stranded or single-stranded, and if single stranded can be the coding strand or non-coding (anti-sense) strand. Thus, the term "polynucleotide encoding a polypeptide" encompasses a polynucleotide that includes only coding sequences for the polypeptide as well as a polynucleotide which includes additional coding and/or non-coding sequences.

The present invention further relates to variants of the hereinabove described polynucleotides that encode, for example, fragments, analogs, and derivatives. The variant of the polynucleotide can be a naturally occurring allelic variant of the polynucleotide or a non-naturally occurring variant of the polynucleotide. As hereinabove indicated, the polynucleotide can have a coding sequence which is a naturally occurring allelic variant of the coding sequence of a disclosed polypeptide. As known in the art, an allelic variant is an alternate form of a polynucleotide sequence which has a substitution, deletion, or addition of one or more nucleotides, and which does not substantially alter the function of the encoded polypeptide.

The present invention also includes polynucleotides wherein the coding sequence for the mature polypeptide can be fused in the same reading frame to a polynucleotide which aids in, for example, expression, secretion, protein stability of a polypeptide from a host cell including, for example, a leader sequence which functions as a secretory sequence for controlling transport of a polypeptide from the cell. The polypeptide having a leader sequence is a preprotein and can have the leader sequence cleaved by the host cell to form the mature form of the polypeptide. The polynucleotides can also encode for a proprotein which is the mature protein plus additional 5' amino acid residues. A mature protein having a prosequence is a proprotein and is an inactive form of the protein. Once the prosequence is cleaved an active mature protein remains. Thus, for example, the polynucleotide of the present invention can encode for a mature protein, or for a protein having a prosequence or for a protein having both a prosequence and presequence (leader sequence).

The polynucleotides of the present invention can also have the coding sequence fused in-frame to a marker sequence which allows for purification of the polypeptide of the present invention. The marker sequence can be a hexa-histidine tag supplied by a pQE-9 vector to provide for purification of the mature polypeptide fused to the marker in the case of a bacterial host, or, for example, the marker sequence can be a hemagglutinin (HA) tag when a mammalian host, e.g. COS-7 cells, is used. The HA tag corresponds to an epitope derived from the influenza hemagglutinin protein (Wilson, I., et al., Cell 37:767 (1984)).

Certain embodiments of the invention include isolated nucleic acid molecules comprising a polynucleotide having a nucleotide sequence at least 90% identical, 95% identical, and in some embodiments, at least 96%, 97%, 98% or 99% identical to a nucleotide that encodes the disclosed sequences.

The polynucleotide variants can contain alterations in the coding regions, non-coding regions, or both. In some embodiments the polynucleotide variants contain alterations which produce silent substitutions, additions, or deletions, but do not alter the properties or activities of the encoded polypeptide. In some embodiments, nucleotide variants are produced by silent substitutions due to the degeneracy of the genetic code. Polynucleotide variants can be produced for a variety of reasons, e.g., to optimize codon expression for a particular host (change codons in the human mRNA to those preferred by a bacterial host such as E. coli).

Soluble Receptor Polypeptides

The polypeptides of the present invention can be recombinant polypeptides, natural polypeptides, or synthetic polypeptides having the sequence of SEQ ID NOS. 1-9. It will be recognized in the art that some amino acid sequences of the invention can be varied without significant effect on the structure or function of the protein. If such differences in sequence are contemplated, it should be remembered that there will be critical areas on the protein which determine activity. Thus, the invention further includes variations of the polypeptides which show substantial activity or which include regions of FZD protein such as the protein portions discussed herein. Such mutants include deletions, insertions, inversions, repeats, and type substitutions. As indicated below, guidance concerning which amino acid changes are likely to be phenotypically silent can be found in Bowie, et al., Science 247: 1306-1310 (1990).

Thus, the fragments, derivatives, or analogs of the polypeptides of the invention can be: (i) one in which one or more of the amino acid residues are substituted with a conserved or non-conserved amino acid residue and such substituted amino acid residue can or can not be one encoded by the genetic code; or (ii) one in which one or more of the amino acid residues includes a substituted group; or (iii) one in which the mature polypeptide is fused with another compound, such as a compound to increase the half-life of the polypeptide (for example, polyethylene glycol); or (iv) one in which the additional amino acids are fused to the mature polypeptide, such as a leader or secretory sequence or a sequence which is employed for purification of the mature polypeptide or a proprotein sequence. Such fragments, derivatives, and analogs are deemed to be within the scope of those skilled in the art from the teachings herein.

Of particular interest are substitutions of charged amino acids with another charged amino acid and with neutral or negatively charged amino acids. The latter results in proteins with reduced positive charge to improve the characteristics of the soluble receptor protein. The prevention of aggregation is highly desirable, as aggregation of proteins not only results in a loss of activity but can also be problematic when preparing pharmaceutical formulations, because they can be immunogenic. (Pinckard et al., Clin. Exp. Immunol. 2:331-340 (1967); Robbins et al., Diabetes 36:838-845 (1987); Cleland et al. Crit. Rev. Therapeutic Drug Carrier Systems 10:307-377 (1993)).

As indicated, changes are typically of a minor nature, such as conservative amino acid substitutions that do not significantly affect the folding or activity of the protein (see Tables 1 and 2).

TABLE 1

| Conservative Amino Acid Substitutions | |
|---|---|
| Aromatic | Phenylalanine |
|  | Tryptophan |
|  | Tyrosine |
| Hydrophobic | Leucine |
|  | Isoleucine |
|  | Valine |
| Polar | Glutamine |
|  | Asparagine |
| Basic | Arginine |
|  | Lysine |
|  | Histidine |
| Acidic | Aspartic Acid |
|  | Glutamic Acid |
| Small | Alanine |
|  | Serine |
|  | Threonine |
|  | Methionine |
|  | Glycine |

TABLE 2

| Amino Acid Substitutions | | |
|---|---|---|
| Original Residue | Substitutions | Exemplary Substitutions |
| Ala (A) | Val | Val; Leu; Ile |
| Arg (R) | Lys | Lys; Gln; Asn |
| Asn (N) | Gln | Gln; His; Lys; Arg |
| Asp (D) | Glu | Glu |
| Cys (C) | Ser | Ser |
| Gln (Q) | Asn | Asn |

TABLE 2-continued

Amino Acid Substitutions

| Original Residue | Substitutions | Exemplary Substitutions |
|---|---|---|
| Glu (E) | Asp | Asp |
| Gly (G) | Pro | Pro |
| His (H) | Arg | Asn; Gln; Lys; Arg |
| Ile (I) | Leu | Leu; Val; Met; Ala; Phe; norleucine |
| Leu (L) | Ile | norleucine; Ile; Val; Met; Ala; Phe |
| Lys (K) | Arg | Arg; Gln; Asn |
| Met (M) | Leu | Leu; Phe; Ile |
| Phe (F) | Leu | Leu; Val; Ile; Ala |
| Pro (P) | Gly | Gly |
| Ser (S) | Thr | Thr |
| Thr (T) | Ser | Ser |
| Trp (W) | Tyr | Tyr |
| Tyr (Y) | Phe | Trp; Phe; Thr; Ser |
| Val (V) | Leu | Ile; Leu; Met; Phe; Ala; norleucine |

Of course, the number of amino acid substitutions a skilled artisan would make depends on many factors, including those described above. Generally speaking, the number of substitutions for any given soluble receptor polypeptide will not be more than 50, 40, 30, 25, 20, 15, 10, 5 or 3.

The polypeptides of the present invention include the polypeptides of SEQ ID NOS: 1-9 as well as polypeptides which have at certain times at least 90% similarity to the polypeptides of SEQ ID NOS: 1-9, and at certain times at least 95% similarity to the polypeptides of SEQ ID NOS: 1-9, and at certain times at least 96%, 97%, 98%, or 99% similarity to the polypeptides of SEQ ID NOS: 1-9. As known in the art "similarity" between two polypeptides is determined by comparing the amino acid sequence and its conserved amino acid substitutes of one polypeptide to the sequence of a second polypeptide.

Fragments or portions of the polypeptides of the present invention can be employed for producing the corresponding full-length polypeptide by peptide synthesis; therefore, the fragments can be employed as intermediates for producing the full-length polypeptides. Fragments or portions of the polynucleotides of the present invention can be used to synthesize full-length polynucleotides of the present invention.

A fragment of the proteins of this invention is a portion or all of a protein which is capable of binding to a cancer stem cell marker protein or cancer stem cell protein binding partner (e.g. a receptor, co-receptor, ligand, or co-ligand). This fragment has a high affinity for a cancer stem cell marker protein or cancer stem cell protein binding partner (e.g. a receptor, co-receptor, ligand, or co-ligand). Some fragments of fusion proteins are protein fragments comprising at least part of the extracellular portion of a cancer stem cell marker protein or cancer stem cell protein binding partner bound to at least part of a constant region of an immunoglobulin. The affinity can be in the range of about $10^{-11}$ to $10^{-12}$ M, although the affinity can vary considerably with fragments of different sizes, ranging from $10^{-7}$ to $10^{-13}$ M. In some embodiments, the fragment is about 10-255 amino acids in length and comprises the cancer stem cell marker protein ligand binding site linked to at least part of a constant region of an immunoglobulin.

The polypeptides and analogs can be further modified to contain additional chemical moieties not normally part of the protein. Those derivatized moieties can improve the solubility, the biological half life or absorption of the protein. The moieties can also reduce or eliminate any desirable side effects of the proteins and the like. An overview for those moieties can be found in *Remington's Pharmaceutical Sciences,* 20th ed., Mack Publishing Co., Easton, Pa. (2000).

The chemical moieties most suitable for derivatization include water soluble polymers. A water soluble polymer is desirable because the protein to which it is attached does not precipitate in an aqueous environment, such as a physiological environment. In some embodiments, the polymer will be pharmaceutically acceptable for the preparation of a therapeutic product or composition. One skilled in the art will be able to select the desired polymer based on such considerations as whether the polymer/protein conjugate will be used therapeutically, and if so, the desired dosage, circulation time, resistance to proteolysis, and other considerations. The effectiveness of the derivatization can be ascertained by administering the derivative, in the desired form (i.e., by osmotic pump, or by injection or infusion, or, further formulated for oral, pulmonary or other delivery routes), and determining its effectiveness. Suitable water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly 1,3 dioxolane, poly 1,3,6 trioxane, ethylene/maleic anhydride copolymer, polyaminoacids (either homopolymers or random copolymers), and dextran or poly(n-vinyl pyrrolidone) polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde can have advantages in manufacturing due to its stability in water.

The number of polymer molecules so attached can vary, and one skilled in the art will be able to ascertain the effect on function. One can mono-derivatize, or can provide for a di-, tri-, tetra- or some combination of derivatization, with the same or different chemical moieties (e.g., polymers, such as different weights of polyethylene glycols). The proportion of polymer molecules to protein (or peptide) molecules will vary, as will their concentrations in the reaction mixture. In general, the optimum ratio (in terms of efficiency of reaction in that there is no excess unreacted protein or polymer) will be determined by factors such as the desired degree of derivatization (e.g., mono-, di-, tri-, etc.), the molecular weight of the polymer selected, whether the polymer is branched or unbranched, and the reaction conditions.

The polyethylene glycol molecules (or other chemical moieties) should be attached to the protein with consideration of effects on functional or antigenic domains of the protein. There are a number of attachment methods available to those skilled in the art. See for example, EP 0 401 384, the disclosure of which is hereby incorporated by reference (coupling PEG to G-CSF), see also Malik et al., *Exp. Hematol* 20:1028-1035 (1992) (reporting pegylation of GM-CSF using tresyl chloride). For example, polyethylene glycol can be covalently bound through amino acid residues via a reactive group, such as, a free amino or carboxyl group. Reactive groups are those to which an activated polyethylene glycol molecule can be bound. The amino acid residues having a free amino group can include lysine residues and the N-terminal amino acid residue. Those having a free carboxyl group can include aspartic acid residues, glutamic acid residues, and the C terminal amino acid residue. Sulfhydryl groups can also be used as a reactive group for attaching the polyethylene glycol molecule(s). For therapeutic purposes, attachment at an amino group, such as attachment at the N-terminus or lysine group can be performed. Attachment at residues important for receptor binding should be avoided if receptor binding is desired.

One can specifically desire an amino-terminal chemically modified protein. Using polyethylene glycol as an illustration of the present compositions, one can select from a variety of polyethylene glycol molecules (by molecular weight, branching, etc.), the proportion of polyethylene glycol molecules to protein (or peptide) molecules in the reaction mix, the type of pegylation reaction to be performed, and the method of obtaining the selected N-terminally pegylated protein. The method of obtaining the N-terminally pegylated preparation (i.e., separating this moiety from other monopegylated moieties if necessary) can be by purification of the N-terminally pegylated material from a population of pegylated protein molecules. Selective N-terminal chemical modification can be accomplished by reductive alkylation which exploits differential reactivity of different types of primary amino groups (lysine versus the N-terminal) available for derivatization in a particular protein. Under the appropriate reaction conditions, substantially selective derivatization of the protein at the N-terminus with a carbonyl group containing polymer is achieved. For example, one can selectively N-terminally pegylate the protein by performing the reaction at a pH which allows one to take advantage of the pKa differences between the epsilon amino group of the lysine residues and that of the alpha amino group of the N terminal residue of the protein. By such selective derivatization, attachment of a water soluble polymer to a protein is controlled: the conjugation with the polymer takes place predominantly at the N-terminus of the protein and no significant modification of other reactive groups, such as the lysine side chain amino groups, occurs. Using reductive alkylation, the water soluble polymer can be of the type described above, and should have a single reactive aldehyde for coupling to the protein. Polyethylene glycol propionaldehyde, containing a single reactive aldehyde, can be used.

Pegylation can be carried out by any of the pegylation reactions known in the art. See, for example: Focus on Growth Factors, 3(2): 4-10 (1992); EP 0 154 316, the disclosure of which is hereby incorporated by reference; EP 0 401 384; and the other publications cited herein that relate to pegylation. The pegylation can be carried out via an acylation reaction or an alkylation reaction with a reactive polyethylene glycol molecule (or an analogous reactive water soluble polymer).

Thus, it is contemplated that soluble receptor polypeptides to be used in accordance with the present invention can include pegylated soluble receptor protein or variants, wherein the PEG group(s) is (are) attached via acyl or alkyl groups. Such products can be mono pegylated or poly pegylated (e.g., containing 2 6, and typically 2 5, PEG groups). The PEG groups are generally attached to the protein at the α or ε amino groups of amino acids, but it is also contemplated that the PEG groups could be attached to any amino group attached to the protein, which is sufficiently reactive to become attached to a PEG group under suitable reaction conditions.

The polymer molecules used in both the acylation and alkylation approaches can be selected from among water soluble polymers as described above. The polymer selected should be modified to have a single reactive group, such as an active ester for acylation or an aldehyde for alkylation, so that the degree of polymerization can be controlled as provided for in the present methods. An exemplary reactive PEG aldehyde is polyethylene glycol propionaldehyde, which is water stable, or mono C1-C10 alkoxy or aryloxy derivatives thereof (see, U.S. Pat. No. 5,252,714). The polymer can be branched or unbranched. For the acylation reactions, the polymer(s) selected should have a single reactive ester group. For the present reductive alkylation, the polymer(s) selected should have a single reactive aldehyde group. Generally, the water soluble polymer will not be selected from naturally occurring glycosyl residues since these are usually made more conveniently by mammalian recombinant expression systems. The polymer can be of any molecular weight, and can be branched or unbranched. One water soluble polymer for use herein is polyethylene glycol. As used herein, polyethylene glycol is meant to encompass any of the forms of PEG that have been used to derivatize other proteins, such as mono (C1-C10) alkoxy- or aryloxy-polyethylene glycol.

Other reaction parameters, such as solvent, reaction times, temperatures, etc., and means of purification of products, can be determined case by case based on the published information relating to derivatization of proteins with water soluble polymers (see the publications cited herein).

The isolated polypeptides described herein can be produced by any suitable method known in the art. Such methods range from direct protein synthetic methods to constructing a DNA sequence encoding isolated polypeptide sequences and expressing those sequences in a suitable transformed host. For example, cDNA can be obtained by screening a human cDNA library with a labeled DNA fragment encoding the polypeptide of SEQ ID NO: 1 and identifying positive clones by autoradiography. Further rounds of plaque purification and hybridization are performed using conventional methods.

In some embodiments of a recombinant method, a DNA sequence is constructed by isolating or synthesizing a DNA sequence encoding a wild-type protein of interest. Optionally, the sequence can be mutagenized by site-specific mutagenesis to provide functional analogs thereof. See, e.g. Zoeller et al., Proc. Natl. Acad. Sci, USA 81:5662-5066 (1984) and U.S. Pat. No. 4,588,585. Another method of constructing a DNA sequence encoding a polypeptide of interest would be by chemical synthesis using an oligonucleotide synthesizer. Such oligonucleotides can be designed based on the amino acid sequence of the desired polypeptide and selecting those codons that are favored in the host cell in which the recombinant polypeptide of interest will be produced.

Standard methods can be applied to synthesize an isolated polynucleotide sequence encoding an isolated polypeptide of interest. For example, a complete amino acid sequence can be used to construct a back-translated gene. Further, a DNA oligomer containing a nucleotide sequence coding for the particular isolated polypeptide can be synthesized. For example, several small oligonucleotides coding for portions of the desired polypeptide can be synthesized and then ligated. The individual oligonucleotides typically contain 5' or 3' overhangs for complementary assembly.

Once assembled (by synthesis, site-directed mutagenesis or another method), the mutant DNA sequences encoding a particular isolated polypeptide of interest will be inserted into an expression vector and operatively linked to an expression control sequence appropriate for expression of the protein in a desired host. Proper assembly can be confirmed by nucleotide sequencing, restriction mapping, and expression of a biologically active polypeptide in a suitable host. As is well known in the art, in order to obtain high expression levels of a transfected gene in a host, the gene must be operatively linked to transcriptional and translational expression control sequences that are functional in the chosen expression host.

Recombinant expression vectors can be used to amplify and express DNA encoding cancer stem cell marker polypeptide fusions. Recombinant expression vectors are replicable DNA constructs which have synthetic or cDNA-derived DNA fragments encoding a cancer stem cell marker polypeptide fusion or a bioequivalent analog operatively linked to suitable transcriptional or translational regulatory elements derived from mammalian, microbial, viral or insect genes. A transcriptional unit generally comprises an assembly of (1) a genetic element or elements having a regulatory role in gene expression, for example, transcriptional promoters or enhancers, (2) a structural or coding sequence which is transcribed into mRNA and translated into protein, and (3) appropriate transcription and translation initiation and termination sequences, as described in detail below. Such regulatory elements can include an operator sequence to control transcription. The ability to replicate in a host, usually conferred by an origin of replication, and a selection gene to facilitate recognition of transformants can additionally be incorporated. DNA regions are operatively linked when they are functionally related to each other. For example, DNA for a signal peptide (secretory leader) is operatively linked to DNA for a polypeptide if it is expressed as a precursor which participates in the secretion of the polypeptide; a promoter is operatively linked to a coding sequence if it controls the transcription of the sequence; or a ribosome binding site is operatively linked to a coding sequence if it is positioned so as to permit translation. Generally, operatively linked means contiguous and, in the case of secretory leaders, means contiguous and in reading frame. Structural elements intended for use in yeast expression systems can include a leader sequence enabling extracellular secretion of translated protein by a host cell. Alternatively, where recombinant protein is expressed without a leader or transport sequence, it can include an N-terminal methionine residue. This residue can optionally be subsequently cleaved from the expressed recombinant protein to provide a final product.

The choice of expression control sequence and expression vector will depend upon the choice of host. A wide variety of expression host/vector combinations can be employed. Useful expression vectors for eukaryotic hosts, include, for example, vectors comprising expression control sequences from SV40, bovine papilloma virus, adenovims and cytomegalovirus. Useful expression vectors for bacterial hosts include known bacterial plasmids, such as plasmids from *Esherichia coli*, including pCR 1, pBR322, pMB9 and their derivatives, wider host range plasmids, such as M13 and filamentous single-stranded DNA phages.

Suitable host cells for expression of a cancer stem cell marker protein include prokaryotes, yeast, insect or higher eukaryotic cells under the control of appropriate promoters. Prokaryotes include gram negative or gram positive organisms, for example *E. coli* or bacilli. Higher eukaryotic cells include established cell lines of mammalian origin as described below. Cell-free translation systems could also be employed. Appropriate cloning and expression vectors for use with bacterial, fungal, yeast, and mammalian cellular hosts are described by Pouwels et al., *Cloning Vectors: A Laboratory Manual*, Elsevier, N.Y. (1985), the relevant disclosure of which is hereby incorporated by reference.

Various mammalian or insect cell culture systems are also advantageously employed to express recombinant protein. Expression of recombinant proteins in mammalian cells can be performed because such proteins are generally correctly folded, appropriately modified and completely functional. Examples of suitable mammalian host cell lines include the COS-7 lines of monkey kidney cells, described by Gluzman, *Cell* 23:175 (1981), and other cell lines capable of expressing an appropriate vector including, for example, L cells, C127, 3T3, Chinese hamster ovary (CHO), HeLa and BHK cell lines. Mammalian expression vectors can comprise nontranscribed elements such as an origin of replication, a suitable promoter and enhancer linked to the gene to be expressed, and other 5' or 3' flanking nontranscribed sequences, and 5' or 3' nontranslated sequences, such as necessary ribosome binding sites, a polyadenylation site, splice donor and acceptor sites, and transcriptional termination sequences. Baculovirus systems for production of heterologous proteins in insect cells are reviewed by Luckow and Summers, *Bio/Technology* 6:47 (1988).

The proteins produced by a transformed host can be purified according to any suitable method. Such standard methods include chromatography (e.g., ion exchange, affinity and sizing column chromatography), centrifugation, differential solubility, or by any other standard technique for protein purification. Affinity tags such as hexahistidine, maltose binding domain, influenza coat sequence and glutathione-S-transferase can be attached to the protein to allow easy purification by passage over an appropriate affinity column. Isolated proteins can also be physically characterized using such techniques as proteolysis, nuclear magnetic resonance and x-ray crystallography.

For example, supernatants from systems which secrete recombinant protein into culture media can be first concentrated using a commercially available protein concentration filter, for example, an Amicon or Millipore Pellicon ultrafiltration unit. Following the concentration step, the concentrate can be applied to a suitable purification matrix. Alternatively, an anion exchange resin can be employed, for example, a matrix or substrate having pendant diethylaminoethyl (DEAE) groups. The matrices can be acrylamide, agarose, dextran, cellulose or other types commonly employed in protein purification. Alternatively, a cation exchange step can be employed. Suitable cation exchangers include various insoluble matrices comprising sulfopropyl or carboxymethyl groups. Finally, one or more reversed-phase high performance liquid chromatography (RP-HPLC) steps employing hydrophobic RP-HPLC media, e.g., silica gel having pendant methyl or other aliphatic groups, can be employed to further purify a cancer stem cell protein-Fc composition. Some or all of the foregoing purification steps, in various combinations, can also be employed to provide a homogeneous recombinant protein.

Recombinant protein produced in bacterial culture is usually isolated by initial extraction from cell pellets, followed by one or more concentration, salting-out, aqueous ion exchange or size exclusion chromatography steps. High performance liquid chromatography (HPLC) can be employed for final purification steps. Microbial cells employed in expression of a recombinant protein can be disrupted by any convenient method, including freeze-thaw cycling, sonication, mechanical disruption, or use of cell lysing agents.

Inhibiting Tumor Cell Growth

The present invention also provides methods for inhibiting the growth of tumorigenic cells expressing a cancer stem cell marker using the antagonists of a cancer stem cell marker described herein. In certain embodiments, the method of inhibiting the growth of tumorigenic cells expressing a cancer stem cell marker comprises contacting the cell with an antagonist against a cancer stem cell marker in vitro. For example, an immortalized cell line or a cancer cell line that expresses a cancer stem cell marker is cultured in medium to which is added an antagonist of the expressed cancer stem cell marker to inhibit cell growth. Alternatively tumor cells and/or tumor stem cells are isolated from a patient sample such as, for example, a tissue biopsy, pleural effusion, or blood sample and cultured in medium to which is added an antagonist of a cancer stem cell marker to inhibit cell growth. In certain embodiments, the antagonist is a cancer stem cell marker protein fusion that specifically binds to a cancer stem cell marker protein or cancer stem cell marker binding protein (e.g. receptor, co-receptor, ligand, or co-ligand). For example, a purified cancer stem cell marker protein fusion is added to the culture medium of isolated cancer stem cell to inhibit cell growth.

In certain embodiments, the method of inhibiting the growth of tumorigenic cells expressing a cancer stem cell marker comprises contacting the cell with an antagonist against a cancer stem cell marker in vivo. In certain embodiments, contacting a tumorigenic cell with an antagonist to a cancer stem cell marker is undertaken in an animal model. For example, xenografts expressing a cancer stem cell marker are grown in immunocompromised mice (e.g. NOD/SCID mice) that are administered an antagonist to a cancer stem cell marker to inhibit tumor growth. Alternatively, cancer stem cells that express a cancer stem cell marker are isolated from a patient sample such as, for example, a tissue biopsy, pleural effusion, or blood sample and injected into immunocompromised mice that are then administered an antagonist against the cancer stem cell marker to inhibit tumor cell growth. In some embodiments, the antagonist of a cancer stem cell marker is administered at the same time or shortly after introduction of tumorigenic cells into the animal to prevent tumor growth. In some embodiments, the antagonist of a cancer stem cell marker is administered as a therapeutic after the tumorigenic cells have grown to a specified size. In some embodiments, the antagonist is a cancer stem cell marker protein fusion that specifically binds to a cancer stem cell marker protein or cancer stem cell marker binding protein (e.g. receptor, co-receptor, ligand, or co-ligand). In certain embodiments, contacting a tumorigenic cell with an antagonist to a cancer stem cell is undertaken in a human patient diagnosed with cancer.

Pharmaceutical Compositions

The present invention further provides pharmaceutical compositions comprising antagonists (e.g. antibodies) that target a cancer stem cell marker. These pharmaceutical compositions find use in inhibiting tumor cell growth and treating cancer in human patients.

Formulations are prepared for storage and use by combining a purified antagonist (e.g. antibody) of the present invention with a pharmaceutically acceptable carrier, excipient, and/or stabilizer as a sterile lyophilized powder, aqueous solution, etc (Remington, *The Science and Practice of Pharmacy,* 20th Edition, Mack Publishing (2000)). Suitable carriers, excipients, or stabilizers comprise nontoxic buffers such as phosphate, citrate, and other organic acids; salts such as sodium chloride; antioxidants including ascorbic acid and methionine; preservatives (e.g. octadecyldimethylbenzyl ammonium chloride; hexamethonium chloride; benzalkonium chloride; benzethonium chloride; phenol, butyl or benzyl alcohol; alkyl parabens, such as methyl or propyl paraben; catechol; resorcinol; cyclohexanol; 3-pentanol; and m-cresol); low molecular weight polypeptides (such as less than about 10 amino acid residues); proteins such as serum albumin, gelatin, or immunoglobulins; hydrophilic polymers such as polyvinylpyrrolidone; amino acids such as glycine, glutamine, asparagine, histidine, arginine, or lysine; carbohydrates such as monosacchandes, disaccharides, glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN or polyethylene glycol (PEG).

The pharmaceutical composition of the present invention can be administered in any number of ways for either local or systemic treatment. Administration can be topical (such as to mucous membranes including vaginal and rectal delivery) such as transdermal patches, ointments, lotions, creams, gels, drops, suppositories, sprays, liquids and powders; pulmonary (e.g., by inhalation or insufflation of powders or aerosols, including by nebulizer; intratracheal, intranasal, epidermal and transdermal); oral; or parenteral including intravenous, intraarterial, subcutaneous, intraperitoneal or intramuscular injection or infusion; or intracranial (e.g., intrathecal or intraventricular) administration.

The therapeutic formulation can be in unit dosage form. Such formulations include tablets, pills, capsules, powders, granules, solutions or suspensions in water or non-aqueous media, or suppositories for oral, parenteral, or rectal administration or for administration by inhalation. In solid compositions such as tablets the principal active ingredient is mixed with a pharmaceutical carrier. Conventional tableting ingredients include corn starch, lactose, sucrose, sorbitol, talc, stearic acid, magnesium stearate, dicalcium phosphate or gums, and other diluents (e.g. water) to form a solid preformulation composition containing a homogeneous mixture of a compound of the present invention, or a non-toxic pharmaceutically acceptable salt thereof. The solid preformulation composition is then subdivided into unit dosage forms of the type described above. The tablets, pills, etc of the novel composition can be coated or otherwise compounded to provide a dosage form affording the advantage of prolonged action. For example, the tablet or pill can comprise an inner composition covered by an outer component. Furthermore, the two components can be separated by an enteric layer that serves to resist disintegration and permits the inner component to pass intact through the stomach or to be delayed in release. A variety of materials can be used for such enteric layers or coatings, such materials including a number of polymeric acids and mixtures of polymeric acids with such materials as shellac, cetyl alcohol and cellulose acetate.

Pharmaceutical formulations include antagonists of the present invention complexed with liposomes (Epstein, et al., *Proc. Natl. Acad. Sci. USA* 82:3688 (1985); Hwang, et al., *Proc. Natl. Acad. Sci. USA* 77:4030 (1980); and U.S. Pat. Nos. 4,485,045 and 4,544,545). Liposomes with enhanced circulation time are disclosed in U.S. Pat. No. 5,013,556. Liposomes can be generated by the reverse phase evaporation with a lipid composition comprising phosphatidylcholine, cholesterol, and PEG-derivatized phosphatidylethanolamine (PEG-PE). Liposomes are extruded through filters of defined pore size to yield liposomes with the desired diameter.

The antagonist can also be entrapped in microcapsules. Such microcapsules are prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions as described in Remington, *The Science and Practice of Pharmacy,* 20th Ed. Mack Publishing (2000).

In addition sustained-release preparations can be prepared. Suitable examples of sustained-release preparations include semipermeable matrices of solid hydrophobic polymers containing the antibody, which matrices are in the form of shaped articles (e.g. films, or microcapsules). Examples of sustained-release matrices include polyesters, hydrogels such as poly (2-hydroxyethyl-methacrylate) or poly(vinylalcohol), polylactides (U.S. Pat. No. 3,773,919), copolymers of L-glutamic acid and 7 ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), sucrose acetate isobutyrate, and poly-D-(–)-3-hydroxybutyric acid.

Treatment with Antagonists

It is envisioned that the antagonists of the present invention can be used to treat various conditions characterized by expression and/or increased responsiveness of cells to a cancer stem cell marker. Particularly it is envisioned that the antagonists (e.g. antibodies) against a cancer stem cell marker will be used to treat proliferative disorders including but not limited to benign and malignant tumors of the kidney, liver, bladder, breast, stomach, ovary, colon, rectum, prostate, lung, vulva, thyroid, head and neck, brain (glioblastoma, astrocytoma, medulloblastoma, etc), blood and lymph (leukemias and lymphomas).

The antagonists are administered as an appropriate pharmaceutical composition to a human patient according with known methods. Suitable method of administration include intravenous administration as a bolus or by continuous infusion over a period of time include, but are not limited to intramuscular, intraperitoneal, intravenuous, intracerobrospinal, subcutaneous, intra-articular, intrasynovial, intrathecal, oral, topical, or inhalation routes.

In certain embodiments, the treatment involves the combined administration of an antagonist of the present invention and a chemotherapeutic agent or cocktail of multiple different chemotherapeutic agents. Treatment with an antagonist can occur prior to, concurrently with, or subsequent to administration of chemotherapies. Chemotherapies contemplated by the invention include chemical substances or drugs which are known in the art and are commercially available, such as Doxorubicin, 5-Fluorouracil, Cytosine arabinoside ("Ara-C"), Cyclophosphamide, Thiotepa, Busulfan, Cytoxin, Taxol, Methotrexate, Cisplatin, Melphalan, Vinblastine and Carboplatin. Combined administration can include co-administration, either in a single pharmaceutical formulation or using separate formulations, or consecutive administration in either order but preferably within a time period such that all active agents can exert their biological activities simultaneously. Preparation and dosing schedules for such chemotherapeutic agents can be used according to manufacturers' instructions or as determined empirically by the skilled practitioner. Preparation and dosing schedules for such chemotherapy are also described in *Chemotherapy Service*, M. C. Perry, ed., Williams & Wilkins, Baltimore, Md. (1992).

In certain embodiments, the treatment involves the combined administration of an antagonist of the present invention and radiation therapy. Treatment with an antagonist can occur prior to, concurrently with, or subsequent to administration of radiation therapy. Any dosing schedules for such radiation therapy can be used as determined by the skilled practitioner.

In certain embodiments, the treatment can involve the combined administration of antagonists of the present invention with antibodies against additional tumor associated antigens including, but not limited to, antibodies that bind to EGFR, HER2, and VEGF. Furthermore, treatment can include administration of one or more cytokines, can be accompanied by surgical removal of cancer cells or any other therapy deemed necessary by a treating physician.

For the treatment of the disease, the appropriate dosage of an antagonist of the present invention depends on the type of disease to be treated, the severity and course of the disease, the responsiveness of the disease, whether the antagonist is administered for therapeutic or preventative purposes, previous therapy, patient's clinical history, and so on all at the discretion of the treating physician. The antagonist can be administered one time or over a series of treatments lasting from several days to several months, or until a cure is effected or a diminution of the disease state is achieved (e.g. reduction in tumor size). Optimal dosing schedules can be calculated from measurements of drug accumulation in the body of the patient and will vary depending on the relative potency of an individual antagonist. The administering physician can easily determine optimum dosages, dosing methodologies and repetition rates. In general, dosage is from 0.01 µg to 100 mg per kg of body weight, and can be given once or more daily, weekly, monthly or yearly. The treating physician can estimate repetition rates for dosing based on measured residence times and concentrations of the drug in bodily fluids or tissues.

Kits

In yet other embodiments, the present invention provides kits that can be used to perform the methods described herein. In certain embodiments, a kit comprises a purified cancer stem cell marker soluble receptor in one or more containers. In some embodiments, the kits contain all of the components necessary and/or sufficient to perform a detection assay, including all controls, directions for performing assays, and any necessary software for analysis and presentation of results. In certain embodiments, the present invention provides a compartment kit in which reagents are contained in separate containers. Such containers allow one to efficiently transfer reagents from one compartment to another compartment such that the samples and reagents are not cross-contaminated, and the agents or solutions of each container can be added in a quantitative fashion from one compartment to another. Such containers will include a container which will accept the test sample, a container which contains the soluble receptor used in the methods, containers which contain wash reagents (such as phosphate buffered saline, Tris-buffers, etc.), and containers which contain the reagents used to detect the hound antibody or probe. One skilled in the art will readily recognize that the disclosed polynucleotides, polypeptides and antibodies of the present invention can be readily incorporated into one of the established kit formats which are well known in the art.

EXAMPLES

Example 1

Production of FZD Fc Soluble Receptor Proteins and In Vivo Half-Life Determination Soluble versions of the N-terminal extracellular domain (ECD) of human FZD receptors bind Wnt ligands and act as antagonists of Wnt pathway signaling (He et al., (1997) Science 275:1652-54; Tanaka et al., (1998) Proc. Natl. Acad. Sci. 95:10164-69; Holmen et al., (2002) JBC 277:34727-35; Vincan et al., (2005) Differentiation 73:142-53). Soluble FZD receptors were generated by ligating 1) the ECD or 2) the Fri domain of FZD10, FZD7, FZD5, FZD4, or FZD8 in-frame to human IgG$_1$ Fc isolated from a human B-cell library (SEQ ID NO: 4) in a vector for expression in insect cells and HEK 293 cells. Standard recombinant DNA technology was used to isolate polynucleotides encoding FZD receptor ECDs including: amino acids from approximately 21 to 227 of FZD10 (FZD10 ECD.Fc); amino acids from approximately 32 to 255 of FZD7 (FZD7 ECD.Fc); amino acids from approximately 27 to 233 of FZD5 (FZD5 ECD.Fc); and amino acids from approximately 37 to 224 of FZD4 (FZD4 ECD.Fc) as well as FZD receptor Fri domains including: amino acids from approximately 21 to 154 of FZD10 (FZD10 Fri.Fc); amino acids from approximately 32 to 171 of FZD7 (FZD7 Fri.Fc);

amino acids from approximately 27 to 157 of FZD5 (FZD5 Fri.Fc); amino acids from approximately 37 to 170 of FZD4 (FZD4 Fri.Fc); and amino acids from approximately 28 to 158 of FZD8 (FZD8 Fri.Fc). The soluble receptor proteins were purified over a protein A column.

To determine the half-life of soluble FZD receptors, in vivo experiments were performed. Specifically, 200 ug of purified FZD4 Fri.Fc, FZD8 Fri.Fc, FZD5 Fri.Fc, and FZD5 ECD.Fc were administered i.p. to mice (n=3) and blood samples were obtained at indicated time points (FIG. 1). Serum proteins retained on Protein A agarose beads were separated on an SDS-PAGE gel, transferred to nitrocellulose membranes, and probed with HRP conjugated goat anti-human IgG Fc fragment to detect the hFc fusion proteins. FZD4 Fri.Fc, FZD5 Fri.Fc, and FZD8 Fri.Fc proteins are all present in blood serum 72 hours following injection, and FZD5 Fri.Fc and FZD8 Fri.Fc are present in blood serum 96 hours following injection (FIG. 1). In contrast, FZD5 ECD.Fc is undetectable after 24 hours (FIG. 1).

Example 2

In Vitro Assays to Evaluate FZD Fc Soluble Receptor Protein

This example describes methods for in vitro assays to test the activity of FZD Fc receptor on cell proliferation and pathway activation.

Proliferation Assay

The expression of a FZD receptor by different cancer cell lines is quantified using Taqman analysis. Cell lines identified as expressing a FZD receptor are plated at a density of $10^4$ cell per well in 96-well tissue culture microplates and allowed to spread for 24 hours. Subsequently cells are cultured for an additional 12 hours in fresh DMEM with 2% FCS at which point soluble FZD Fc receptor protein versus control protein is added to the culture medium in the presence of 10 umol/L BrdU. Following BrdU labeling, the culture media is removed, and the cells fixed at room temperature for 30 min in ethanol and reacted for 90 min with peroxidase-conjugated monoclonal anti-BrdU antibody (clone BMG 6H8, Fab fragments). The substrate is developed in a solution containing tetramethylbenzidine and stopped after 15 min with 25 ul of 1 mol/L $H_2SO_4$. The color reaction is measured with an automatic ELISA plate reader using a 450 nm filter (UV Microplate Reader; Bio-Rad Laboratories, Richmond, Calif.). All experiments are performed in triplicate. The ability of FZD Fc soluble receptor protein to inhibit cell proliferation compared is determined.

Pathway Activation Assay

The ability of soluble FZD Fc receptor protein to block activation of the Wnt signaling pathway is determined in vitro. In one embodiment, HEK 293 cells cultured in DMEM supplemented with antibiotics and 10% FCS are co-transfected with 1) Wnt7B and FZD10 expression vectors to activate the Wnt signaling pathway; 2) a TCF/Luc wild-type or mutant reporter vector containing three copies of the TCF-binding domain upstream of a firefly luciferase reporter gene to measure canonical Wnt signaling levels (Gazit et al., 1999, Oncogene 18:5959-66); and 3) a *Renilla* luciferase reporter (Promega; Madison, Wis.) as an internal control for transfection efficiency. FZD Fc protein is then added to the cell culture medium. Forty-eight hours following transfection, luciferase levels are measured using a dual luciferase assay kit (Promega; Madison, Wis.) with firefly luciferase activity normalized to *Renilla* luciferase activity. Three independent experiments are preformed in triplicate. The ability of soluble FZD10 Fc protein to inhibit Wnt pathway activation is thus determined.

In some embodiments, increasing amounts of FZD Fc fusion proteins were incubated with L cells in the presence or absence of Wnt3a ligand and the Wnt3a induced stabilization of β-catenin was determined by immunoblotting. Only in the presence of Wnt3a was β-catenin detectable, and this stabilization was blocked by increasing amounts of FZD5 ECD.Fc, FZD8 Fri.Fc and FZD4 Fri.Fc soluble receptor protein (FIG. 2) demonstrating that FZD Fc soluble receptor proteins antagonize Wnt pathway signaling activated by the Wnt3a ligand.

The ability of FZD:Fc fusion proteins to antagonize signaling by different Wnt ligands was then determined. HEK 293 cells stably transfected with 8×TCF-luciferase reporter were incubated with increasing amounts of FZD Fri.Fc soluble receptors in the presence of different Wnt ligands including Wnt1, Wnt2, Wnt3, Wnt3a and Wnt7b. FZD4 Fri.Fc, FZD5 Fri.Fc and FZD8 Fri.Fc fusion proteins inhibited Wnt signaling mediated by all five Wnt ligands (FIG. 3).

Example 3

In Vivo Prevention of Tumor Growth Using FZD Fc Soluble Receptor Protein

This example describes the use of a FZD Fc soluble receptor to prevent tumor growth in a xenograft model.

Tumor cells from a patient sample (solid tumor biopsy or pleural effusion) that have been passaged as a xenograft in mice were prepared for repassaging into experimental animals as described in detail above. Dissociated tumor cells (<10,000 cells per animal; n=10) were then injected subcutaneously into the mammary fat pads NOD/SCID mice to elicit tumor growth.

In certain embodiments, dissociated tumor cells are first sorted into tumorigenic and non-tumorigenic cells based on cell surface markers before injection into experimental animals. Specifically, tumor cells dissociated as described above are washed twice with Hepes buffered saline solution (HBSS) containing 2% heat-inactivated calf serum (HICS) and resuspended at $10^6$ cells per 100 ul. Antibodies are added and the cells incubated for 20 min on ice followed by two washes with HBSS/2% HICS. Antibodies include anti-ESA (Biomeda, Foster City, Calif.), anti-CD44, anti-CD24, and Lineage markers anti-CD2, -CD3, -CD10, -CD16, -CD18, -CD31, -CD64, and -CD140b (collectively referred to as Lin; PharMingen, San Jose, Calif.). Antibodies are directly conjugated to fluorochromes to positively or negatively select cells expressing these markers. Mouse cells are eliminated by selecting against H2Kd+ cells, and dead cells are eliminated by using the viability dye 7AAD. Flow cytometry is performed on a FACSVantage (Becton Dickinson, Franklin Lakes, N.J.). Side scatter and forward scatter profiles are used to eliminate cell clumps. Isolated ESA+, CD44+, CD24−/low, Lin-tumorigenic cells are then injected subcutaneously into the mammary fat pads for breast tumors or into the flank for non-breast tumors of NOD/SCID mice to elicit tumor growth.

In certain embodiments, two days after tumor cell injection, the animals were treated with FZD7 ECD.Fc soluble receptor, FZD10 ECD.Fc soluble receptor, or FZD5 ECD.Fc soluble receptor. Each test injected animal received 10 mg/kg FZD7 ECD.Fc, FZD5 ECD.Fc or FZD10 ECD.Fc protein intraperitoneal (i.p.) 2-3× per week for a total of 4 weeks. Control injected animals were injected 2× per week for a total of 4 weeks. Tumor size was assessed on days 21, 24, 28, and 30. Treatment with both soluble FZD10 ECD.Fc and FZD7 ECD.Fc reduced total tumor volume compared to control treated animals (FIG. 4). The reduction of tumor volume by FZD7 ECD.Fc was statistically significant on day 28 and day 30 (FIG. 4).

Next the effect of FZD Fc soluble receptor treatment on the presence of cancer stem cells in a tumor is assessed. Tumor samples from FZD Fc versus control treated mice are cut up into small pieces, minced completely using sterile blades, and single cell suspensions obtained by enzymatic digestion and mechanical disruption. Dissociated tumor cells are then analyzed by FACS analysis for the presence of tumorigenic cancer stem cells based on ESA+, CD44+, CD24−/low, Lin− surface cell marker expression as described in detail above.

The tumorigenicity of cells isolated based on ESA+, CD44+, CD24−/low, Lin-expression following FZD Fc treatment can then assessed. 5,000, 1,000, 500, and 100 isolated ESA+, CD44+, CD24−/low, Lin-cancer stem cells from FZD Fc treated versus control treated mice are re-injected subcutaneously into the mammary fat pads of NOD/SCID mice. The tumorigenicity of cancer stem cells based on the number of injected cells required for consistent tumor formation is thus determined.

In certain embodiments, female rag-2/γ chain double knockout mice were injected at age 5-7 weeks with 50,000 mouse mammary tumor virus (MMTV)-WNT1 tumor derived cells in the upper right mammary fat pad. Transgenic (MMTV)-Wnt-1 mice exhibit discrete steps of mammary tumorigenesis, including hyperplasia, invasive ductal carcinoma, and distant metastasis, and thus this mouse model of breast cancer provides a useful tool for analyzing the role of Wnts in tumor formation and growth (Nusse and Varmus (1982) Cell 31:99-109). Tumors from these mice were dissociated and these dissociated tumor cells used for tumor propagation purposes. Mice with tumor cells implanted in the mammary fat pad were treated 5× weekly with 200 ul PBS (n=10) or FZD8 Fri.Fc soluble receptor (10 mg/kg) diluted in PBS. Once tumors were palpable, tumor sizes were measured twice weekly. Treatment with soluble receptor FZD8 Fri.Fc dramatically reduced the growth of tumors compared to the control treatment with PBS (FIG. 5).

To again test the ability of FZD soluble receptors to inhibit tumor growth, NOD/SCID mice were injected with 50,000 PE13 breast tumor cells. One day following cell injection, 200 ul FZD8 Fri.Fc soluble receptor diluted in PBS was injected i.p. at 10 mg/kg or 200 ul PBS was injected and treatment was continued 5× weekly (n=10 per experimental group). Tumor growth was monitored weekly until growth was detected, then tumor growth was measured twice weekly. Treatment of animals with FZD8 Fri.Fc significantly reduced breast tumor cell growth compared to PBS injected controls (FIG. 6).

Example 4

In Vivo Treatment of Tumor Growth Using FZD Fc Soluble Receptor Protein

This example describes the use of a FZD Fc soluble receptor to treat tumors in a xenograft model.

In certain embodiments, 50,000 MMTV Wnt1 breast tumor derived cells in Matrigel were sub-cutaneously implanted into 5-7 week old female rag-2/γ chain double knockout mice. On day nineteen, mice with tumors were randomly assigned to groups with a mean tumor volume of 65 mm³, and on day twenty-six, treatment with FZD8 Fri.Fc or FZD5 Fri.Fc fusion proteins was initiated. Specifically, five times per week FZD8 Fri.Fc fusion protein was administered at increasing concentrations (5 mg/kg, 10 mg/kg, and 30 mg/kg), and FZD5 Fri.Fc was administered at 10 mg/kg. Control animals were treated with PBS.

A dose dependent anti-tumor activity of FZD8 Fri.Fc fusion protein was observed (FIG. 7). At the lowest dose-5 mg/kg-FZD8 Fri.Fc reduced the growth of tumors relative to mice treated with PBS, but the 10 mg/kg and 30 mg/kg FZD8 Fri.Fc treatment regimens were significantly more effective in reducing the size of the pre-established tumors. In contrast, FZD5 Fri.Fc did not display anti-tumor effects on established breast tumors that require wnt1 for growth.

Example 5

In Vivo Treatment of Tumors Using FZD Fc Soluble Receptor Protein

This example describes the use of a FZD Fc soluble receptor to treat cancer in a xenograft model.

Tumor cells from a patient sample (solid tumor biopsy or pleural effusion) that have been passaged as a xenograft in mice are prepared for repassaging into experimental animals. Tumor tissue is removed, cut up into small pieces, minced completely using sterile blades, and single cell suspensions obtained by enzymatic digestion and mechanical disruption. Dissociated tumor cells are then injected subcutaneously into the mammary fat pads for breast tumors or into the flank for non-breast tumors NOD/SCID mice to elicit tumor growth. Alternatively, ESA+, CD44+, CD24−/low, Lin-tumorigenic tumor cells are isolated as described in detail above and injected.

Following tumor cell injection, animals are monitored for tumor growth. Once tumors reach an average size of approximately 150 to 200 mm, FZD Fc protein treatment begins. Each animal receives 10 mg/kg FZD Fc or control protein i.p. two to five times per week for a total of 6 weeks. Tumor size is assessed twice a week during these 6 weeks. The ability of FZD Fc to prevent further tumor growth or to reduce tumor size compared to control antibodies is thus determined.

Example 6

Treatment of Human Cancer Using FZD Fc Soluble Receptor Protein

This example describes methods for treating cancer using a FZD Fc soluble receptor to target tumors comprising cancer stem cells and/or tumor cells in which FZD receptor expression has been detected.

The presence of cancer stem cell marker expression can first be determined from a tumor biopsy. Tumor cells from a biopsy from a patient diagnosed with cancer are removed under sterile conditions. In one embodiment the tissue biopsy is fresh-frozen in liquid nitrogen, embedded in O.C.T., and cut on a cryostat as 10 um sections onto glass slides. Alternatively the tissue biopsy is formalin-fixed, paraffin-embedded, and cut on a microtome as 10 um section onto glass slides. Sections are incubated with antibodies against a FZD receptor to detect protein expression. Additionally, the presence of cancer stem cells can be determined. Tissue biopsy samples are cut up into small pieces, minced completely using sterile blades, and cells subject to enzymatic digestion and mechanical disruption to obtain a single cell suspension. Dissociated tumor cells are then incubated with anti-ESA, -CD44, -CD24, -Lin, and -FZD antibodies to detect cancer stem cells, and the presence of ESA+, CD44+, CD24−/low, Lin−, FZD+ tumor stem cells is determined by flow cytometry as described in detail above.

Cancer patients whose tumors are diagnosed with cancer stem cells are treated with a FZD:Fc soluble receptor. Human FZD Fc fusion protein generated as described above is purified and formulated with a suitable pharmaceutical carrier in PBS for injection. Patients are treated with FZD Fc preferably once a week for at least 10 weeks, but more preferably once a week for at least about 14 weeks. Each administration of FZD Fc should be a pharmaceutically effective dose of about 2 to about 100 mg/ml or about 5 to about 40 mg/ml. FZD Fc can be administered prior to, concurrently with, or after standard radiotherapy regimens or chemotherapy regimens using one or more chemotherapeutic agent, such as oxaliplatin, fluorouracil, leucovorin, or streptozocin. Patients are monitored to determine whether such treatment has resulted in an antitumor response, for example, based on tumor regression, reduction in the incidences of new tumors, lower tumor antigen expression, decreased numbers of cancer stem cells, or other means of evaluating disease prognosis.

All publications and patents mentioned in the above specification are herein incorporated by reference. Various modifications and variations of the described method and system of the invention will be apparent to those skilled in the art without departing from the scope and spirit of the invention. Although the invention has been described in connection with specific embodiments, it should be understood that the invention as claimed should not be unduly limited to such specific embodiments. Indeed, various modifications of the described modes for carrying out the invention which are obvious to those skilled in the relevant fields are intended to be within the scope of the following claims.

```
FZD10 N-terminal extracellular domain
                                                 SEQ ID NO: 1
MQRPGPRLWLVLQVMGSCAAISSMDMERPGDGKCQPIEIPMCKDIGYNMT

RMPNLMGHENQREAAIQLHEFAPLVEYGCHGHLRFFLCSLYAPMCTEQVS

TPIPACRVMCEQARLKCSPIMEQFNFKWPDSLDCRKLPNKNDPNYLCMEA

PNNGSDEPTRGSGLFPPLFRPQRPHSAQEHPLKDGGPGRGGCDNPGKFHH

VEKSASCAPLCTPGVDVYWSREDKRFA

FZD7 N-terminal extracellular domain
                                                 SEQ ID NO: 2
MRDPGAAAPLSSLGLCALVLALLGALSAGAGAQPYHGEKGISVPDHGFCQ

PISIPLCTDIAYNQTILPNLLGHTNQEDAGLEVHQFYPLVKVQCSPELRF

FLCSMYAPVCTVLDQAIPPCRSLCERARQGCEALMNKFGFQWPERLRCEN

FPVHGAGEICVGQNTSDGSGGPGGGPTAYPTAPYLPDLPFTALPPGASDG

RGRPAFPFSCPRQLKVPPYLGYRFLGERDCGAPCEPGRANGLMYFKEEER

RFARL

FZD5 N-terminal extracellular domain
                                                 SEQ ID NO: 3
MARPDPSAPPSLLLLLLAQLVGRAAAASKAPVCQEITVPMCRGIGYNLTH

MPNQFNHDTQDEAGLEVHQFWPLVEIQCSPDLRFFLCSMYTPICLPDYHK

PLPPCRSVCERAKAGCSPLMRQYGFAWPERMSCDRLPVLGRDAEVLCMDY

NRSEATTAPPRPFPAKPTLGPPPGAPASGGECPAGGPFVCKCREPFVPIL
```

```
KESHPLYNKVRTGQVPNCAVPCYQPSFSADERT

Human IgG1 Fc
                                                 SEQ ID NO: 4
DKTHTCPPCPAPELLGGPSVFLFPPKPKDTLMISRTPEVTCVVVDVSHED

PEVKFNWYVDGVEVHNAKTKPREEQYNSTYRVVSVLTVLHQDWLNGKEYK

CKVSNKALPAPIEKTISKAKGQPREPQVYTLPPSRDELTKNQVSLTCLVK

GFYPSDIAVEWESNGQPENNYKTTPPVLDSDGSFFLYSKLTVDKSRWQQG

NVFSCSVMHEALHNHYTQKSLSLSPGK

FZD6 N-terminal extracellular domain
                                                 SEQ ID NO: 5
MEMFTFLLTCIFLPLLRGHSLFTCEPITVPRCMKMAYNMTFFPNLMGHYD

QSIAAVEMEHFLPLANLECSPNIETFLCKAFVPTCIEQIHVVPPCRKLCE

KVYSDCKKLIDTFGIRWPEELECDRLQYCDETVPVTFDPHTEFLGPQKKT

EQVQRDIGFWCPRHLKTSGGQGYKFLGIDQCAPPCPNMYFKSDELEFAKS

FIGTVSI

FZD N-terminal extracellular domain
                                                 SEQ ID NO: 6
MLAMAWRGAGPSVPGAPGGVGLSLGLLLQLLLLLGPARGFGDEEERRCDP

IRISMCQNLGYNVTKMPNLVGHELQTDAELQLTTFTPLIQYGCSSQLQFF

LCSVYVPMCTEKINIPIGPCGGMCLSVKRRCEPVLKEFGFAWPESLNCSK

FPPQNDHNHMCMEGPGDEEVPLPHKTPIQPGEECHSVGTNSDQYIWVKRS

LNCVLKCGYDAGLYSRSAKEFTDI

FZD8 Fri domain
                                                 SEQ ID NO: 7
MEWGYLLEVTSLLAALALLQRSSGAAAASAKELACQEITVPLCKGIGYNY

TYMPNQFNHDTQDEAGLEVHQFWPLVEIQCSPDLKFFLCSMYTPICLEDY

KKPLPPCRSVCERAKAGCAPLMRQYGFAWPDRMRCDRLPEQGNPDTLCMD

YNRTDLTT

FZD4 Fri domain
                                                 SEQ ID NO: 8
MLAMAWRGAGPSVPGAPGGVGLSLGLLLQLLLLLGPARGFGDEEERRCDP

IRISMCQNLGYNVTKMPNLVGHELQTDAELQLTTFTPLIQYGCSSQLQFF

LCSVYVPMCTEKINIPIGPCGGMCLSVKRRCEPVLKEFGFAWPESLNCSK

FPPQNDHNHMCMEGPGDEEV

FZD5 Fri domain
                                                 SEQ ID NO: 9
MARPDPSAPPSLLLLLLAQLVGRAAAASKAPVCQEITVPMCRGIGYNLTH

MPNQFNHDTQDEAGLEVHQFWPLVEIQCSPDLRFFLCSMYTPICLPDYHK

PLPPCRSVCERAKAGCSPLMRQYGFAWPERMSCDRLPVLGRDAEVLCMDY

NRSEATT
```

What is claimed is:

1. A method of inhibiting Wnt signaling in a tumor or tumor cell, comprising contacting the tumor or tumor cell with an effective amount of a soluble receptor, wherein the soluble receptor comprises a polypeptide consisting of:
   (a) a fragment of an extracellular domain of a human Frizzled receptor, wherein the fragment consists essentially of the Fri domain of the human FZD receptor, and the human FZD receptor is FZD4, FZD5, or FZD8; and
   (b) a non-FZD receptor protein sequence comprising:
       (i) a human Fc domain; or
       (ii) a polypeptide having the amino acid sequence of SEQ ID NO:4.

2. The method of claim 1, wherein the fragment comprises the amino acids from approximately 28 to 158 of SEQ NO:7, the amino acids from approximately 37 to 170 of SEQ ID NO:8, or the amino acids from approximately 27 to 157 of SEQ ID NO:9.

3. The method of claim 1, wherein the fragment consists of the amino acids 28 to 158 of SEQ ID NO:7, the amino acids 37 to 170 of SEQ ID NO:8, or the amino acids 27 to 157 of SEQ ID NO:9.

4. The method of claim 1, wherein the non-FZD receptor protein sequence comprises a human Fc domain.

5. The method of claim 1, wherein the non-FZD receptor protein sequence comprises a polypeptide having the amino acid sequence of SEQ ID NO:4.

6. The method of claim 1, wherein the fragment consists essentially of the Fri domain of human FZD8.

7. The method of claim 6, wherein the Fri domain of human FZD8 comprises the amino acids from approximately 28 to 158 of the amino acid sequence of SEQ ID NO:7.

8. The method of claim 1, wherein the fragment consists essentially of the Fri domain of human FZD4.

9. The method of claim 8, wherein the Fri domain of human FZD4 comprises the amino acids from approximately 37 to 170 of the amino acid sequence of SEQ ID NO:8.

10. The method of claim 1, wherein the fragment consists essentially of the Fri domain of human FZD5.

11. The method of claim 10, wherein the Fri domain of human FZD5 comprises the amino acids from approximately 27 to 157 of the amino acid sequence of SEQ ID NO:9.

12. The method of claim 1, wherein the tumor or tumor cells are from a breast tumor, colorectal tumor, lung tumor, pancreatic tumor, prostate tumor, or a head and neck tumor.

* * * * *